US010980756B1

(12) United States Patent
Glick

(10) Patent No.: US 10,980,756 B1
(45) **Date of Patent: *Apr. 20, 2021**

(54) METHODS OF TREATMENT

(71) Applicant: First Wave Bio, Inc., Ann Arbor, MI (US)

(72) Inventor: Gary Glick, Ann Arbor, MI (US)

(73) Assignee: First Wave Bio, Inc., Ann Arbor, MI (US)

(*) Notice: Subject to any disclaimer, the term of this patent is extended or adjusted under 35 U.S.C. 154(b) by 0 days.

This patent is subject to a terminal disclaimer.

(21) Appl. No.: 16/835,307

(22) Filed: Mar. 31, 2020

Related U.S. Application Data

(60) Provisional application No. 63/002,324, filed on Mar. 30, 2020, provisional application No. 62/993,688, filed on Mar. 23, 2020, provisional application No. 62/990,414, filed on Mar. 16, 2020.

(51) Int. Cl.

| | |
|---|---|
| ***A61K 31/167*** | (2006.01) |
| ***A61K 31/7052*** | (2006.01) |
| ***A61K 31/135*** | (2006.01) |
| ***A61K 31/4706*** | (2006.01) |
| ***A61K 31/685*** | (2006.01) |

(52) U.S. Cl.
CPC .......... *A61K 31/167* (2013.01); *A61K 31/135* (2013.01); *A61K 31/4706* (2013.01); *A61K 31/685* (2013.01); *A61K 31/7052* (2013.01)

(58) Field of Classification Search
CPC ... A61K 31/167; A61K 31/135; A61K 31/685
See application file for complete search history.

(56) References Cited

U.S. PATENT DOCUMENTS

| | | | |
|---|---|---|---|
| 3,079,297 | A | 2/1963 | Schraufstatter et al. |
| 4,496,086 | A | 1/1985 | Duchadeau |
| 5,280,784 | A | 1/1994 | Kohler |
| 5,309,900 | A | 5/1994 | Knoch et al. |
| 5,312,046 | A | 5/1994 | Knoch et al. |
| 5,458,136 | A | 10/1995 | Jaser et al. |
| 5,461,695 | A | 10/1995 | Knoch |
| 5,549,102 | A | 8/1996 | Lintl et al. |
| 5,663,155 | A | 9/1997 | McCaffrey |
| 5,740,966 | A | 4/1998 | Blaha-Schnabel |
| 5,905,090 | A | 5/1999 | Bertolini |
| 5,914,132 | A | 6/1999 | Kelm et al. |
| 5,957,389 | A | 9/1999 | Wunderlich et al. |
| 6,000,394 | A | 12/1999 | Blaha-Schnabel et al. |
| 6,085,741 | A | 7/2000 | Becker |
| 6,176,237 | B1 | 1/2001 | Wunderlich et al. |
| 6,224,910 | B1 | 5/2001 | Ullah et al. |
| 6,228,396 | B1 | 5/2001 | Watts |
| 6,513,519 | B2 | 2/2003 | Gallern |
| 6,513,727 | B1 | 2/2003 | Jaser et al. |
| 6,862,890 | B2 | 3/2005 | Williams, III et al. |
| 7,132,546 | B2 | 11/2006 | Kato et al. |
| 7,544,712 | B1 | 6/2009 | Hsu et al. |
| 7,635,722 | B1 | 12/2009 | Bachynsky et al. |
| 7,691,578 | B2 | 4/2010 | Spiegelman |
| 7,927,613 | B2 | 4/2011 | Almarsson et al. |
| 7,989,498 | B2 | 8/2011 | Saunders |
| 8,097,759 | B2 | 1/2012 | Muto et al. |
| 8,148,328 | B2 | 4/2012 | Fogelman |
| 8,262,657 | B2 | 9/2012 | Muto et al. |
| 8,968,786 | B2 | 3/2015 | Johnston et al. |
| 9,023,368 | B2 | 5/2015 | Basit et al. |
| 9,044,391 | B2 | 6/2015 | Willaims et al. |
| 9,061,027 | B2 | 6/2015 | Hitt et al. |

(Continued)

FOREIGN PATENT DOCUMENTS

| | | |
|---|---|---|
| CN | 101601670 | 12/2009 |
| CN | 102861014 | 1/2013 |

(Continued)

OTHER PUBLICATIONS

Xu (ACS Infectious Diseases; 2020, 6, 909-915; published on Mar. 3, 2020).*

Richardson (The Clinical Biochemist Reviews; vol. 25, 2004, 133-141).*

Mayo Clinic (Niclosamide (Oral Route) Proper Use-Mayo Clinic; published Feb. 2, 2020).*

Wu (Antimicrobial Agents and Chemotherapy; 2004, vol. 48 (7), 2693-2696).*

Kahler et al., "Treatment and side effect management of CTLA-4 antibody therapy in metastatic melanoma," JDDG, 2011, 9:277-285.

nytimes.com [online], "South Korea's Daewoong Pharmaceutical Says Anti-Parasitic Drug Effective Against Coronavirus in Animal Tests," Jun. 2020, [retrieved on Jun. 10, 2020] retrieved from: URL <https://www.nytimes.com/reuters/2020/06/09/world/asia/09reuters-health-coronavirus-pharmaceuticals.html>, 2 pages.

(Continued)

*Primary Examiner* — Pancham Bakshi

(74) *Attorney, Agent, or Firm* — Fish & Richardson P.C.

(57) ABSTRACT

This disclosure features compounds and compositions that are useful in methods of treating coronavirus infections (e.g., useful in methods of treating COVID-19) in a subject in need thereof. The methods include administering to the subject niclosamide compounds (or pharmaceutically acceptable salts and/or co-crystals thereof, e.g., niclosamide). In some embodiments, the niclosamide compounds have one or more properties that include, but are not limited to: a particular purity (e.g., a chemical purity of greater than about 99.0%) or a particular particle size (e.g., a particular particle size distribution and/or a particular particle size range and/or a specific surface area range). In an aspect, the niclosamide compounds described herein (e.g., niclosamide) can form part of compositions, dosage forms (e.g., unit dosage forms), and the like, which are suitable for respiratory administration (e.g., via inhalation and/or intranasally). In another aspect, the niclosamide compounds described herein (e.g., niclosamide) can form part of compositions, dosage forms (e.g., unit dosage forms), and the like, which are suitable for administration to the GI tract (e.g., orally or rectally such as via enema)).

26 Claims, No Drawings

(56) References Cited

U.S. PATENT DOCUMENTS

| | | | |
|---|---|---|---|
| 9,175,906 | B2 | 11/2015 | Scherzer et al. |
| 9,192,583 | B2 | 11/2015 | Shah et al. |
| 9,237,760 | B2 | 1/2016 | Ravishankar et al. |
| 9,308,213 | B2 | 4/2016 | Bannister et al. |
| 9,546,211 | B2 | 1/2017 | Singh |
| 9,566,399 | B1 | 2/2017 | Bono et al. |
| 9,598,422 | B2 | 3/2017 | Beck et al. |
| 9,622,974 | B2 | 4/2017 | Johnston et al. |
| 9,669,036 | B2 | 6/2017 | Roizmann et al. |
| 9,724,344 | B2 | 8/2017 | Hitt et al. |
| 10,092,512 | B2 | 10/2018 | Johnston et al. |
| 10,189,797 | B2 | 1/2019 | Chen et al. |
| 10,231,955 | B2 | 3/2019 | Williams, III et al. |
| 10,285,945 | B2 | 5/2019 | Johnston et al. |
| 10,292,951 | B2 | 5/2019 | Glick et al. |
| 10,434,062 | B2 | 10/2019 | Johnston et al. |
| 10,463,680 | B2 | 11/2019 | Sommer et al. |
| 10,562,864 | B2 | 2/2020 | Chen et al. |
| 10,588,864 | B2 | 3/2020 | Linanli |
| 10,744,103 | B2 | 8/2020 | Glick et al. |
| 10,772,854 | B2 | 9/2020 | Glick et al. |
| 2002/0035061 | A1 | 3/2002 | Krieger et al. |
| 2004/0022861 | A1 | 2/2004 | Willaims, III et al. |
| 2004/0071757 | A1 | 4/2004 | Rolf et al. |
| 2004/0091523 | A1 | 5/2004 | Weibel |
| 2005/0123571 | A1 | 6/2005 | Rossini et al. |
| 2009/0062396 | A1 | 3/2009 | Olesen et al. |
| 2009/0163408 | A1 | 6/2009 | Fogelman et al. |
| 2009/0208582 | A1 | 8/2009 | Johnston et al. |
| 2012/0035106 | A1 | 2/2012 | Betancourt et al. |
| 2013/0078226 | A1 | 3/2013 | Nakauchi et al. |
| 2013/0231312 | A1 | 9/2013 | Jin |
| 2013/0243886 | A1 | 9/2013 | Hu et al. |
| 2014/0256661 | A1 | 9/2014 | Armstrong |
| 2015/0056160 | A1 | 2/2015 | Bachynsky et al. |
| 2015/0133405 | A1 | 5/2015 | Pelletier et al. |
| 2016/0074328 | A1 | 3/2016 | Scherzer et al. |
| 2016/0228415 | A1 | 8/2016 | Rossignol et al. |
| 2016/0243117 | A1 | 8/2016 | Menon et al. |
| 2017/0056347 | A1 | 3/2017 | Glick et al. |
| 2017/0165238 | A1 | 6/2017 | Williams, III et al. |
| 2018/0015153 | A1 | 1/2018 | Tang et al. |
| 2018/0147161 | A1 | 5/2018 | Williams, III et al. |
| 2018/0243333 | A1 | 8/2018 | Brown et al. |
| 2019/0060289 | A1 | 2/2019 | Deretic et al. |
| 2019/0160028 | A1 | 5/2019 | Li et al. |
| 2019/0269661 | A1 | 9/2019 | Williams, III et al. |
| 2019/0298670 | A1 | 10/2019 | Glick et al. |
| 2019/0343783 | A1 | 11/2019 | Yook et al. |
| 2019/0274958 | A1 | 12/2019 | Johnston et al. |
| 2020/0022931 | A1 | 1/2020 | Deshpande et al. |
| 2020/0046659 | A1 | 2/2020 | Melnyk et al. |
| 2020/0069572 | A1 | 3/2020 | Johnston et al. |
| 2020/0147012 | A1 | 5/2020 | Glick et al. |
| 2020/0147013 | A1 | 5/2020 | Glick et al. |
| 2020/0268694 | A1 | 8/2020 | Glick et al. |
| 2020/0276140 | A1 | 9/2020 | Glick et al. |

FOREIGN PATENT DOCUMENTS

| | | | |
|---|---|---|---|
| CN | 105063018 | A | 11/2015 |
| EP | 0938338 | B1 | 9/2009 |
| EP | 3168211 | | 5/2017 |
| WO | WO 1991/13281 | | 9/1991 |
| WO | WO 2002/060411 | | 8/2002 |
| WO | WO 2004/006906 | | 1/2004 |
| WO | WO 2004/064808 | | 8/2004 |
| WO | WO 2006/026502 | | 3/2006 |
| WO | WO 2006/120178 | | 11/2006 |
| WO | WO 2008/127746 | | 10/2008 |
| WO | WO 2009/002874 | | 12/2008 |
| WO | WO 2009/103035 | | 8/2009 |
| WO | WO 2010/048114 | | 4/2010 |
| WO | WO 2011/035321 | | 3/2011 |
| WO | WO 2012/068274 | | 5/2012 |
| WO | WO 2012/143377 | | 10/2012 |
| WO | WO 2012/154944 | | 11/2012 |
| WO | WO 2014/108571 | | 7/2014 |
| WO | WO 2014/185973 | | 11/2014 |
| WO | WO 2005/017755 | | 2/2015 |
| WO | WO 2014/023329 | | 2/2015 |
| WO | WO 2015/017755 | | 5/2015 |
| WO | WO 2015/106150 | | 7/2015 |
| WO | WO 2016/178704 | | 11/2016 |
| WO | WO 2016/193136 | | 12/2016 |
| WO | WO 2017/040864 | | 3/2017 |
| WO | WO 2017/223491 | | 12/2017 |
| WO | WO 2018/017426 | | 1/2018 |
| WO | WO 2018/136559 | | 7/2018 |
| WO | WO 2018/141063 | | 8/2018 |
| WO | WO 2018/173069 | | 9/2018 |
| WO | WO 2018/191776 | | 10/2018 |
| WO | WO 2018/205016 | | 11/2018 |
| WO | WO 2018/213834 | | 11/2018 |
| WO | WO 2018/128515 | | 12/2018 |
| WO | WO 2019/051437 | | 3/2019 |
| WO | WO 2019/051440 | | 3/2019 |
| WO | WO 2019/126283 | | 6/2019 |
| WO | WO 2019/147626 | | 8/2019 |
| WO | WO 2019/217164 | | 11/2019 |

OTHER PUBLICATIONS

Thejakartapost.com [online] "Daewoong Pharmaceutical says anti-parasitic drug effective against coronavirus in animal tests," Jun. 2020, [retrieved on Jun. 10, 2020], retrieved from: URL<https://www.thejakartapost.com/news/2020/06/09/s-koreas-daewoong-pharmaceutical-says-anti-parasitic-drug-effective-against-coronavirus-.html, 4 pages.

Amidon et al., "Colon-Targeted Oral Drug Delivery Systems: Design Trends and Approaches," AAPS PharmSciTech, 2015, 16(4):731-741.

Anatherapeutics.com [online], "Niclosamide & COVID-19: Let's Keep This Simple," available on or before Apr. 2020, [retrieved on May 19, 2020], retrieved from: URL<https://anatherapeutics.com/home/niclosamine-and-covid19-keep-it-simple>, 4 pages.

Anatherapeutics.com [online], "Our Plan," available on or before Apr. 2020, [retrieved on May 19, 2020], retrieved from: URL<https://anathempeutics.com/home/our-plan>, 5 pages.

Anonymous, "New Delivery Method Could Make Niclosamide an Effective Antiviral to Treat COVID-19," UTexas PressRelease, Apr. 6, 2020, [retrieved on May 19, 2020], retrieved from URL<https://news.utexas.edu/2020/04/06/new-delivery-method-could-make-niclosamide-an-effective-antiviral-to-treat-covid-19/> 6 pages.

Auriemma et al., "Prilling for the development of multi-particulate colon drug delivery systems: Pectin vs. pectin-alginate beads," Carbohydrate Polymers, 2013, 92(1):367-373.

Bewtra et al., "Update on the risk of lymphoma following immunosuppressive therapy for inflammatory bowel disease," Expert Rev Clin Immunol., 2010,6(4): 559-566.

Bouman-Boyer et al., "An International Guideline for the Preparation, Care and Use of Medicinal Products," Practical Pharmaceutics, Aug. 24, 2015, 11.9.5.2 p. 220.

Casadevall et al., "The convalescent sera option for containing COVID-19." The Journal of Clinical Investigation, 2020 130(4):1545-1548.

Cen.acs.org [online], "Can old drugs take down a new coronavirus?," Mar. 20, 2020, [retrieved on May 19, 2020], retrieved from: URL<https://cen.acs.org/sections/coronavirus/biological-chemistry/infectious-disease/coronavirus-drug-repurposing.html>, 4 pages.

Chang et al. "Potential therapeutic agents for COVID-19 based on the analysis of protease and RNA polymerase docking." Preprints 2020, 11 pages.

Chang et al., "Pharmacokinetics of Anti-SARS-CoV Agent Niclosamide and Its Analogs in Rats," Journal of Food and Drug Analysis, 2006, 14(4):329-333.

Cho et al., [kxan.com] "Can an existing drug be re-purposed to treat COVID-19 patients? UT researchers working to find out," Apr. 6, 2020, [retrieved on May 19, 2020, retrieved from URL<https://

(56) References Cited

OTHER PUBLICATIONS www.kxan.com/news/coronavirus/can-an-existing-drug-be-re-purposed-to-treat-covid-19-patients-ut-researchers-working-to-find-out/>.

Corman et al. "Detection of 2019 Novel Coronavirus (2019-nCoV) by Real-Time RT-PCR," Eurosurveillance, 25(3):2000045, 8 pages.

Costabile et al. "Toward Repositioning Niclosamide for Antivirulence Therapy of Pseudomonas aeruginosa Lung Infections: Development of Inhalable Formulations through Nanosuspension Technology," Mol Pharm., 2015, 12(8):2604-2617.

CureZone.org, dated Feb. 2, 2014, retrieved on May 15, 2017, retrieved from http://www.curezone.org/forums/fm.asp?i=2146880#i, 2 pages.

Defendants Answer to Complaint, Counterclaim ("the Counterclaim"), filed on Jun. 16, 2017., Case *IFM Therapeutics, First Wave Bio, Inc., Gary D. Glick, and Luigi Franchi* v. *Lycera Corporation* (17-cv-608) (D. Del.).

Dhama et al., "Coronavirus Disease 2019-COVID-19," Preprint 2020, 2020030001.

Dubald et al. "Ophthalmic Drug Delivery Systems for Antibiotherapy—A Review," Pharmaceutics., 2018; 10(1):10, 31 pages.

Filipski et al., "Intestinal targeting of drugs: rational design approaches and challenges," *Current Topics in Medicinal Chemistry.*, 13(7):776-802, 2013.

Frizelle et al., "Hyponatremia and Seizures After Bowel Preparation: Report of Three Cases," Dis Colon Rectum, 2005, 48(2):393-396.

Gautret et al., "Hydroxychloroquine and azithromycin as a treatment of COVID-19: results of an openlabel non-randomized clinical trial," International Journal of Antimicrobial Agents, 2020, 24 pages.

Gautret et al., "Clinical and microbiological effect of a combination of hydroxychloroquine and azithromycin in 80 COVID-19 patients with at least a six-day follow up: A pilot observational study," Travel Medicine and Infectious Disease, 2020, 34:101663.

Gassen et al., "Analysis of SARS-CoV-2-controlled autophagy reveals spermidine, MK-2206, and niclosamide as 1 putative antiviral therapeutics," bioRxiv, 2020, 13 pages.

Grifasi et al., "Using Salt Cosrystals to Improve the Solubility of Niclosamide," Cryst. Growth Des. 2015, 15:1939-1948.

Imramovsky et al., "Crystal Structure of the 5-Chloro Salicylamides: Three Different Types of the H-bonding Influenced Linear Chain Formation in the Solid State," *Crystals.*, 2012, 2:349-361.

International Search Report and Written Opinion in International Application No. PCT/US2016/050012, dated Jan. 23, 2017, 22 pages.

Ir.tffpharma.com [online], "TFF Pharmaceuticals' Inventor Dr. Robert O. Williams III Presents Session on Repurposing Niclosamide for COVID-19 Treatment at AAPS Meeting," Apr. 30, 2020 [retrieved on May 19, 2020], retrieved from URL<https://ir.tffpharma.com/news-releases/news-release-details/tff-pharmaceuticals-inventor-dr-robert-o-williams-iii-presents>, 2 pages.

Jeon et al., "Identification of antiviral drug candidates against SARS-CoV-2 from FDA-approved drugs," bioRxiv, 2020, 20 pages.

Jeon et al., "Identification of antiviral drug candidates against SARS-CoV-2 from FDA-approved drugs," bioRxiv, 2020, 21 pages.

Jin et al., "Epidemiological, clinical and virological characteristics of 74 cases of coronavirus-infected disease 2019 (COVID-19) with gastrointestinal symptoms," Gut 2020, 1-8.

Ko et al., "Arguments in favor of remdesivir for treating SARS-CoV-2 infections," Int J Antimicrob Agents, 2020,105933, 15 pages.

Koreabiomed.com [online], "Pasteur, Daewoong to co-develop COVID-19 drug from parasiticide," Apr. 14, 2020, [retrieved on May 19, 2020], retrieved from: URL<http://www.koreabiomed.com/news/articleView.html?idxno=8003>, 4 pages.

Koreabiomed.com [online], "Parasiticide showed antiviral effect as potential COVID-19 drug," Apr. 24, 2020, [retrieved on May 19, 2020], retrieved from: URL<http://www.koreabiomed.com/news/articleView.html?idxno=8078>, 7 pages.

Kratky et al., "Antiviral Activity of Substituted Salicylanilides—A Review," Mini-Review in Medicinal Chemistry, 2011, 11:956-967.

Labiris et al., "Pulmonary drug delivery. Part II: The role of inhalant deliverydevices and drug formulations in therapeutic effectiveness of aerosolized medications," Br J Clin Pharmacol., 2003, 56(6): 600-612.

Lai et al., "Severe acute respiratory syndrome coronavirus 2 (SARS-CoV-2) and corona virus disease-2019 (COVID-19): the epidemic and the challenges." International journal of antimicrobial agents, 2020, 55(3):105924.

Latimes.com [online], "Drugs for heartburn, gout and depression now being tested as coronavirus treatments," May 2, 2020, [retrieved on May 19, 2020], retrived from: URL<https://www.latimes.com/science/story/2020-05-02/researchers-testing-pepcid-as-coronavirus-treatment>, 7 pages.

Lawrance et al., "A murine model of chronic inflammation-induced intestinal fibrosis down-regulated by antisense NF-kappa B," *Gastroenterology.*, 125(6): 1750-1761, Dec. 2003.

Li et al., "Multi-targeted therapy of cancer by niclosamide: A new application for an old drug," Cancer Letters, 2014, 349:8-14.

Liu et al., "Research and development on therapeutic agents and vaccines for COVID-19 and related human coronavirus diseases," ACS Central Science, Mar. 9, 2020, 17 pages.

Liu et al., "Viral dynamics in mild and severe cases of COVID-19," The Lancet Infectious Diseases, Mar. 19, 2020, 2 pages.

Liu et al., "Viral dynamics in mild and severe cases of COVID-19," The Lancet, 2020,1-4 pages.

Luedeker et al., "Crystal Engineering of Pharameutical Co-crystals: "NMR Crystallography" of Niclosamide Co-crystals," Cryst. Growth Des. 2016 16:3087-3100.

Medscape.com [Online], "Role of Fecal Excretion in Spread of SARS-CoV-2 'Cannot Be Ignored'," May 1, 2020, [retrived on May 19, 2020], retrived from: URL<https://www.medscape.com/viewarticle/929731?nlid=135353_5402&src=wnl_dne_200504_mscpedit&uac=155533FK&impID=2369009&faf=1>, 9 pages.

Memorandum Opionion, *IFM Therapeutics, Inc., First Wave Bio, Inc., Gary D. Glick, and Luigi Franchi*, Plantiff, v., *Lycera Corporation*, Defendant, C.A. No. 17-608-LPS, Aug. 31, 2018, 25 pages.

Memorandum Order signed by the Honorable Leonard P. Stark on Jun. 12, 2017 ("the Order") Case *IFM Therapeutics, First Wave Bio, Inc., Gary D. Glick, and Luigi Franchi* v. *Lycera Corporation* (17-cv-608) (D. Del.).

Milojevic et al., "Amylose as a coating for drug delivery to the colon: Preparation and in vitro evaluation using 5-aminosalicylic acid pellets." Journal of controlled release, 1996, 38:75-84.

Milojevic et al., "Amylose as a coating for drug delivery to the colon: Preparation and in vitro evaluation using glucose pellets." Journal of controlled release, 1996, 38:85-94.

Mook et al., "Structure-activity studies of Wnt/β-catenin inhibition in the Niclosamide chemotype: Identification of derivatives with improved drug exposure," Bioorg. Med Chem, 2015, 23,(17): 5829-5838.

Morin et al., "Niclosamide Prevents Systemic Sclerosis in a Reactive Oxygen Species-Induced Mouse Model," J Immunol, 2016, 197:3018-3028.

Nelson et al., "Azithromycin has anti-viral properties that are critical to consider in the treatment regimen for COVID-19," MindImmune, 2017, 6 pages.

Newswire.com [online], "UNION therapeutics Launches COVID-19 Program in Collaboration With Institut Pasteur Korea," Apr. 14, 2020, [retrieved on May 19, 2020], retrieved from: URL<https://www.newswire.com/news/union-therapeutics-launches-covid-19-program-in-collaboration-with-21127619>, 7 pages.

Newton et al., "Pectin-HPMC E15LV Vs pH sensitive polymer coating films for delayed drug delivery to colon: a comparison of two dissolution models to assess colonic targeting performance in-vitro," International Journal of Applied Research in Natural Products, 2012;5(3), 16 pages.

Pan et al., "Clinical characteristics of COVID-19 patients with digestive symptoms in Hubei, China: a descriptive, cross-sectional, multicenter study," American Journal of Gastroenterol, 2020, 25 pages.

(56) References Cited

OTHER PUBLICATIONS

Patel et al., "Ocular drug delivery systems: an overview," World Journal of Pharmacology, Jun. 9, 2013, 2(2), 35 pages.

Postow et al., "Immune Checkpoint Blockade in Cancer Therapy," J Clin Oncol., 2015, 33(17):1974-1982.

Raoult et al., "Clinical and microbiological effect of a combination of hydroxychloroquine and azithromycin in 80 COVID-19 patients with at least a six-day follow up: an observational study," 2020, 28 pages.

Sanphui et al., "Pharmaceutical Cocrystals of Niclosamide," *Cryst. Growth Des*. Jul. 24, 2012, 12(9):4588-4599.

Scheiffele et al., "Induction of TNBS Colitis in Mice," Current Protocols in Immunology, 2001, 49(1):15.19.1-15.19.14.

Shanmugaraj et al., "Perspectives on monoclonal antibody therapy as potential therapeutic intervention for Coronavirus disease-19 (COVID-19)," Asian Pacific Journal of Allergy and Immunology, Mar. 1, 2020, 38(1):10-8, 9 pages.

Stebbing et al., "COVID-19: combining antiviral and anti-inflammatory treatments," The Lancet Infectious Diseases, Feb. 27, 2020.

Transcript of telephone conference with Honorable Leonard P. Stark, Jun. 9, 2017, ("the TRO transcript") Case *IFM Therapeutics, First Wave Bio, Inc., Gary D. Glick, and Luigi Franchi* v. *Lycera Corporation* (17-cv-608) (D. Del.).

TFF Pharmaceuticals, "Advanced Technology for Better Drug Delivery Options," Present at Proceeding of the May 2020 Corporate Investor Presentation, Power Point, TFF Pharmaceuticals, May 2020, Retrieved from URL<(https://ir.tffpharma.com/static-files/065981d2-3d22-4348-a4be-e3df1e4f96d6)>, 29 pages.

Uniontherapeutics.com [online], "UNION therapeutics launches COVID-19 program in collaboration with Institut Pasteur Korea," Apr. 2, 2020, [retrieved on May 19, 2020], retrieved from: URL<https://www.uniontherapeutics.com/news-events/news/union-therapeutics-launches-covid-19-program-in-collaboration-with-institut-pasteur-korea>, 5 pages.

U.S. Food and Drug Administration, "Emergency Use Authorizations," retrived from <https://www.fda.gov/medical-devices/emergency-situations-medical-devices/emergency-use-authorizations#covid19ivd>, Retrived on Apr. 3, 2020, 12 pages.

World Health Organization, "Protocol: Real-time RT-PCR assays for the detection of SARS-CoV-2," Institut Pasteur, Paris, retreived from <https://www.who.int/docs/default-source/coronaviruse/real-time-rt-pcr-assays-for-the-detection-of-sars-cov-2-institut-pasteur-paris.pdf>, 3 pages.

Wu et al., "Inhibition of Severe Acute Respiratory Syndrome Coronavirus Replication by Niclosamide," Mini-Reviews in Medicinal Chemistry, 2011, 11:956-967.

Xu et al., "Broad Spectrum Antiviral Agent Niclosamide and Its Therapeutic Potential," ACS Infectious Diseases, Mar. 3, 2020, 25 pages.

Yang et al., "Targeting the Endocytic Pathway and Autophagy Process as a Novel Therapeutic Strategy in COVID-19," International Journal of Biological Sciences, Mar. 15, 2020, 16(10):1724-31.

U.S. Appl. No. 15/255,102 (now U.S. Pat. No. 10,292,951, filed Sep. 1, 2016.

U.S. Appl. No. 16/173,667, filed Oct. 29, 2018.

U.S. Appl. No. 16/738,618, filed Jan. 9, 2020.

U.S. Appl. No. 16/738,695, filed Jan. 9, 2020.

U.S. Appl. No. 16/805,245, filed Feb. 28, 2020.

U.S. Appl. No. 16/805,393, filed Feb. 28, 2020.

U.S. Appl. No. 16/871,717, filed May 11, 2020.

U.S. Appl. No. 15/931,320, filed May 13, 2020.

U.S. Appl. No. 16/842,695, filed Apr. 7, 2020.

First Wave Bio, Inc. (First Posted Jun. 18, 2020). Niclosamide In Moderate COVID-19 (Clinicaltrials.gov Identifier NCT04436458). Retrieved from https://clinicaltrials.gov/ct2/show/NCT04436458?term=niclosamide&cond=Covid19&draw=2&rank=2.

First Wave Bio, Inc. (First Posted Sep. 9, 2020). Niclosamide In Moderate COVID-19 (Clinicaltrials.gov Identifier NCT04542434). Retrieved from https://clinicaltrials.gov/ct2/show/NCT04542434?term=niclosamide&cond=Covid19&draw=2&rank=2.

Mayoclinic.org [online],"Niclosamide (Oral Route) Proper Use-Mayo Clinic," published Feb. 2, 2020, [retrieved on Jun. 22, 2020] URL<https://www.mayoclinic.org/drugs-supplements/niclosamide-oral-route/proper-use/drg-20065068>, 3 pages.

Richardson et al.,"The Laboratory Diagnosis of Severe Acute Respiratory Syndrome: Emerging Laboratory Tests for an Emerging Pathogen," The Clinical Biochemist Reviews; 2004, 25:133-141.

* cited by examiner

METHODS OF TREATMENT

CROSS REFERENCE TO RELATED APPLICATIONS

This application claims the benefit of U.S. Provisional Application No. 62/990,414 filed on Mar. 16, 2020; U.S. Provisional Application No. 62/993,688 filed on Mar. 23, 2020; and U.S. Provisional Application No. 63/002,324, filed on Mar. 30, 2020, each of which is incorporated herein by reference in its entirety.

TECHNICAL FIELD

This disclosure features compounds and compositions that are useful in methods of treating coronavirus infections (e.g., useful in methods of treating COVID-19) in a subject in need thereof. The methods include administering to the subject niclosamide compounds (or pharmaceutically acceptable salts and/or co-crystals thereof, e.g., niclosamide). In some embodiments, the niclosamide compounds have one or more properties that include, but are not limited to: a particular purity (e.g., a chemical purity of greater than about 99.0%) or a particular particle size (e.g., a particular particle size distribution and/or a particular particle size range and/or a specific surface area range). In an aspect, the niclosamide compounds described herein (e.g., niclosamide) can form part of compositions, dosage forms (e.g., unit dosage forms), and the like, which are suitable for respiratory administration (e.g., via inhalation and/or intranasally). In another aspect, the niclosamide compounds described herein (e.g., niclosamide) can form part of compositions, dosage forms (e.g., unit dosage forms), and the like, which are suitable for administration to the GI tract (e.g., orally or rectally such as via enema)).

BACKGROUND

Coronaviruses are a group of positive-sense single-strand RNA viruses in the family Coronaviridae in the order Nidovirales. Coronaviruses can be further classified by genera: alphacoronavirus, betacoronavirus, gammacoronavirus, and deltacoronavirus.

Coronaviruses can cause a wide range of disease in both humans and animals, including the common cold. In some cases, coronavirus infection can be more severe. Examples of coronaviruses include SARS-CoV (causing Severe Acute Respiratory Syndrome (SARS)), MERS-CoV (Middle East Respiratory Syndrome (MERS), also sometimes called camel flu). In late 2019, human infection by the coronavirus SARS-CoV-2 (sometimes also called 2019-nCoV) was first recorded in Wuhan, China and quickly spread throughout the globe. The corresponding outbreak of disease is often called COVID-19 (coronavirus disease 2019, sometimes also called Wuhan coronavirus).

Cases of COVID-19 can sometimes be asymptomatic, or sometimes present with flu-like symptoms such as fever, cough, fatigue, shortness of breath, muscle and/or joint pain, sore throat, headache, and/or chills. COVID-19 can have a long incubation period before symptoms appear; the incubation period typically ranges between 1 and 14 days, but has been reported to be up to 27 days. The reported basic reproduction number, the average number of people an infected person is likely to infect, ranges from about 2 to about 5. The fatality rate of COVID-19 varies by location and age of the subject, but on average, it has been reported to be about 2% to about 3%, with more fatalities occurring in older age groups. There are no approved specific therapies for COVID-19.

SUMMARY

This disclosure features compounds and compositions that are useful in methods of treating coronavirus infections (e.g., useful in methods of treating COVID-19) in a subject in need thereof. The methods include administering to the subject niclosamide compounds (or pharmaceutically acceptable salts and/or co-crystals thereof, e.g., niclosamide). In some embodiments, the niclosamide compounds have one or more properties that include, but are not limited to: a particular purity (e.g., a chemical purity of greater than about 99.0%) or a particular particle size (e.g., a particular particle size distribution and/or a particular particle size range and/or a specific surface area range). In an aspect, the niclosamide compounds described herein (e.g., niclosamide) can form part of compositions, dosage forms (e.g., unit dosage forms), and the like, which are suitable for respiratory administration (e.g., via inhalation and/or intranasally). In another aspect, the niclosamide compounds described herein (e.g., niclosamide) can form part of compositions, dosage forms (e.g., unit dosage forms), and the like, which are suitable for administration to the GI tract (e.g., orally or rectally such as via enema)).

In one aspect, this disclosure features a method for treating COVID-19 in a subject in need thereof, the method comprising administering an effective amount of a niclosamide compound, or a pharmaceutically acceptable salt thereof, to the subject.

In another aspect, this disclosure features methods useful for preventing the progression of COVID-19 in a subject (e.g., methods for reducing the likelihood of a subject's developing COVID-19 as well as methods for reducing or slowing the progression of COVID-19 in a subject, e.g., reducing the likelihood that a subject will experience one or more severe or life-threating COVID-19 symptoms). In an aspect, this disclosure features methods of reducing the risk of developing COVID-19 in a subject at risk thereof, the method comprising administering an effective amount (e.g., a prophylactically effective amount) of a niclosamide compound, or a pharmaceutically acceptable salt thereof, to the subject. In a further aspect, this disclosure features methods of preventing COVID-19 in a subject at risk thereof, the method comprising administering an effective amount (e.g., a prophylactically effective amount) of a niclosamide compound, or a pharmaceutically acceptable salt thereof, to the subject. In some of the foregoing embodiments, the niclosamide compound is niclosamide.

In another aspect, this disclosure features a method useful for treating COVID-19 in a subject in need thereof, the method comprising administering an effective amount of a niclosamide compound, or a pharmaceutically acceptable salt thereof, to the GI tract of the subject. In certain embodiments, the method comprises locally (e.g., topically (e.g., by rectal administration such as via enema rectal gel, rectal foam, rectal aerosol, or suppository (e.g., by enema)) administering an effective amount of a niclosamide compound, or a pharmaceutically acceptable salt thereof, to the GI tract of the subject. In certain embodiments, the method comprises orally administering an effective amount of a niclosamide compound, or a pharmaceutically acceptable salt thereof, to the GI tract of the subject (e.g., in a suspension, table, or pill (e.g., in a pill)).

In another aspect, this disclosure features a method for treating mild COVID-19 in a subject in need thereof, the method comprising administering an effective amount of a niclosamide compound, or a pharmaceutically acceptable salt thereof, to the subject. In certain embodiments, the niclosamide compound is administered to the nasal cavity of the subject.

In another aspect, this disclosure features a method for treating severe COVID-19 in a subject in need thereof, the method comprising administering an effective amount of a niclosamide compound, or a pharmaceutically acceptable salt thereof, to the subject. In certain embodiments, the niclosamide compound is administered to the lungs of the subject.

In another aspect, this disclosure features a method for treating COVID-19 in a subject in need thereof, the method comprising orally administering an effective amount of niclosamide:

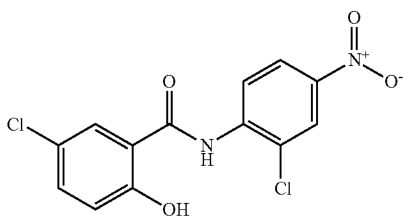 [SMILES: O=C(Nc1ccc([N+](=O)[O-])cc1Cl)c1cc(Cl)ccc1O]

or a pharmaceutically acceptable salt thereof, to the subject.

In another aspect, the disclosure features a method of reducing the risk of developing (e.g., preventing) COVID-19 in a subject at risk thereof, the method comprising administering (e.g., orally administering) an effective amount of niclosamide:

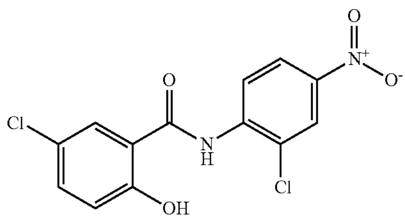 [SMILES: O=C(Nc1ccc([N+](=O)[O-])cc1Cl)c1cc(Cl)ccc1O]

or a pharmaceutically acceptable salt thereof, to the subject.

In another aspect, this disclosure features a method for clearing persistent infection in an asymptomatic (COVID-19 asymptomatic) individual who may or may not have previous COVID-19 illness caused by SARS-COV2, the method comprising orally administering an effective amount of niclosamide:

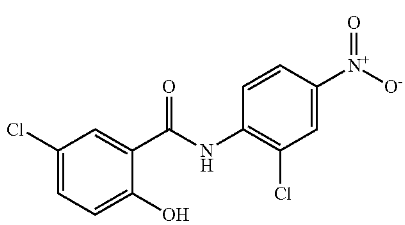 [SMILES: O=C(Nc1ccc([N+](=O)[O-])cc1Cl)c1cc(Cl)ccc1O]

or a pharmaceutically acceptable salt thereof, to the subject.

In another aspect, this disclosure features a method of treating a subject having COVID-19, the method comprising: identifying a subject that has: (i) a respiratory rate of <30 breaths per min; (ii) an oxygen saturation at rest of >93%; and (iii) a ratio of partial pressure of arterial oxygen to fractional concentration of oxygen inspired air of >300 mm Hg; and administering to the nasal cavity of the identified subject a treatment that includes a niclosamide compound, or a pharmaceutically acceptable salt thereof. In certain embodiments, the niclosamide compound, or a pharmaceutically acceptable salt thereof, is formulated for delivery by inhalation.

In another aspect, this disclosure features a method of treating a subject having COVID-19, the method comprising: identifying a subject that has at least one of (i) respiratory distress (i.e., ≥30 breaths per min); (ii) an oxygen saturation at rest of ≤93%; (iii) a ratio of partial pressure of arterial oxygen to fractional concentration of oxygen inspired air of ≤300 mm Hg; and (iv) a severe disease complication; and administering to the lungs of the identified subject a treatment that includes a niclosamide compound, or a pharmaceutically acceptable salt thereof. In certain embodiments, the niclosamide compound, or a pharmaceutically acceptable salt thereof, is formulated for delivery by inhalation.

In another aspect, this disclosure features a method for treating severe COVID-19 in a subject in need thereof, the method comprising administering an effective amount of a niclosamide compound, or a pharmaceutically acceptable salt thereof, to the GI tract of the subject (e.g., by oral delivery).

In another aspect, this disclosure features a method of treating a subject having COVID-19, the method comprising: (a) identifying a subject having (i) a respiratory rate of <30 breaths per min; (ii) an oxygen saturation at rest of >93%; and (iii) a ratio of partial pressure of arterial oxygen to fractional concentration of oxygen inspired air of >300 mm Hg; (b) administering one or more doses of a niclosamide compound, or a pharmaceutically acceptable salt thereof, to the nasal cavity of the subject; (c) after (a) and (b), identifying whether the subject has at least one of: (i) respiratory distress (i.e., ≥30 breaths per min); (ii) an oxygen saturation at rest of ≤93%; (iii) a ratio of partial pressure of arterial oxygen to fractional concentration of oxygen inspired air of ≤300 mm Hg; and (iv) a severe disease complication, e.g., a severe disease complication as described herein; and (d) administering one or more doses of a niclosamide compound, or a pharmaceutically acceptable salt thereof, to the lungs of the subject in which the subject has at least one of: (i) respiratory distress (i.e., ≥30 breaths per min); (ii) an oxygen saturation at rest of ≤93%; (iii) a ratio of partial pressure of arterial oxygen to fractional concentration of oxygen inspired air of ≤300 mm Hg; and (iv) a severe disease complication; or (e) administering additional doses of the niclosamide compound, or a pharmaceutically acceptable salt thereof, to the nasal cavity of the subject in which (i) a respiratory rate of <30 breaths per min; (ii) an oxygen saturation at rest of >93%; and (iii) a ratio of partial pressure of arterial oxygen to fractional concentration of oxygen inspired air of >300 mm Hg.

In another aspect, this disclosure features a method of treating a subject having COVID-19, the method comprising: (a) identifying a subject having (i) a respiratory rate of <30 breaths per min; (ii) an oxygen saturation at rest of >93%; and (iii) a ratio of partial pressure of arterial oxygen to fractional concentration of oxygen inspired air of >300 mm Hg; (b) administering one or more doses of a niclosamide compound, or a pharmaceutically acceptable salt thereof, to the nasal cavity of the subject; (c) after (a) and (b), identifying whether the subject has at least one of: (i) respiratory distress (i.e., ≥30 breaths per min); (ii) an oxygen saturation at rest of ≤93%; (iii) a ratio of partial pressure of arterial oxygen to fractional concentration of oxygen inspired air of ≤300 mm Hg; and (iv) a severe disease complication; and (d) administering one or more doses of a niclosamide compound, or a pharmaceutically acceptable salt thereof, to the GI tract of the subject in which the subject has at least one of: (i) respiratory distress (i.e., ≥30 breaths per min); (ii) an oxygen saturation at rest of ≤93%; (iii) a ratio of partial pressure of arterial oxygen to fractional concentration of oxygen inspired air of ≤300 mm Hg; and (iv) a severe disease complication, e.g., a severe disease complication as described herein; or (e) administering additional doses of the niclosamide compound, or a pharmaceutically acceptable salt thereof, to the nasal cavity of the subject in which (i) a respiratory rate of <30 breaths per min; (ii) an oxygen saturation at rest of >93%; and (iii) a ratio of partial pressure of arterial oxygen to fractional concentration of oxygen inspired air of >300 mm Hg.

In another aspect, this disclosure features a method of treating a subject having COVID-19, the method comprising: (a) identifying a subject having (i) a respiratory rate of <30 breaths per min; (ii) an oxygen saturation at rest of >93%; and (iii) a ratio of partial pressure of arterial oxygen to fractional concentration of oxygen inspired air of >300 mm Hg; (b) administering one or more doses of a niclosamide compound, or a pharmaceutically acceptable salt thereof, to the nasal cavity of the subject; (c) after (a) and (b), identifying whether the subject has at least one of: (i) respiratory distress (i.e., ≥30 breaths per min); (ii) an oxygen saturation at rest of ≤93%; (iii) a ratio of partial pressure of arterial oxygen to fractional concentration of oxygen inspired air of ≤300 mm Hg; and (iv) a severe disease complication; and (d) administering one or more doses of a niclosamide compound, or a pharmaceutically acceptable salt thereof, to the GI tract of the subject and administering one or more doses of a niclosamide compound, or a pharmaceutically acceptable salt thereof, to the lungs of the subject in which the subject has at least one of: (i) respiratory distress (i.e., ≥30 breaths per min); (ii) an oxygen saturation at rest of ≤93%; (iii) a ratio of partial pressure of arterial oxygen to fractional concentration of oxygen inspired air of ≤300 mm Hg; and (iv) a severe disease complication, e.g., a severe disease complication as described herein; or (e) administering additional doses of the niclosamide compound, or a pharmaceutically acceptable salt thereof, to the nasal cavity of the subject in which (i) a respiratory rate of <30 breaths per min; (ii) an oxygen saturation at rest of >93%; and (iii) a ratio of partial pressure of arterial oxygen to fractional concentration of oxygen inspired air of >300 mm Hg.

In another aspect, this disclosure features a method of treating a subject having COVID-19, the method comprising: (a) identifying a subject having at least one of (i) respiratory distress (i.e., ≥30 breaths per min); (ii) an oxygen saturation at rest of ≤93%; (iii) a ratio of partial pressure of arterial oxygen to fractional concentration of oxygen inspired air of ≤300 mm Hg; and (iv) a severe disease complication; (b) administering one or more doses of a niclosamide compound, or a pharmaceutically acceptable salt thereof, to the lungs of the subject; (c) after (a) and (b), identifying whether the subject has (i) a respiratory rate of <30 breaths per min; (ii) an oxygen saturation at rest of >93%; and (iii) a ratio of partial pressure of arterial oxygen to fractional concentration of oxygen inspired air of >300 mm Hg; and (d) administering one or more doses of a niclosamide compound, or a pharmaceutically acceptable salt thereof, to the nasal cavity of the subject in which the subject has (i) a respiratory rate of <30 breaths per min; (ii) an oxygen saturation at rest of >93%; and (iii) a ratio of partial pressure of arterial oxygen to fractional concentration of oxygen inspired air of >300 mm Hg; or (e) administering additional doses of the niclosamide compound, or a pharmaceutically acceptable salt thereof, to the lungs of the subject in which i(i) respiratory distress (i.e., ≥30 breaths per min); (ii) an oxygen saturation at rest of ≤93%; (iii) a ratio of partial pressure of arterial oxygen to fractional concentration of oxygen inspired air of ≤300 mm Hg; and (iv) a severe disease complication.

In another aspect, this disclosure features methods that include administering a co-crystal that includes a niclosamide compound (e.g., niclosamide having any one or more or the properties described herein), or a pharmaceutically acceptable salt thereof and a pharmaceutically acceptable coformer. In some embodiments, the cocrystal has a reduced particle size as described anywhere herein (e.g., the cocrystal itself can be reduced to have the reduced particle size range, and/or the reduced particle size distribution described herein for niclosamide compounds).

In some embodiments, niclosamide compounds (e.g., niclosamide) described herein having a reduced particle size can be readily and efficiently administered, such that the resultant local bioavailability of the administered niclosamide compounds (e.g., niclosamide) in the respiratory tract is relatively high (e.g., as compared with resultant systemic bioavailability of the administered niclosamide compounds (e.g., niclosamide)). Local (non-systemic) administration of the niclosamide compounds (e.g., niclosamide) at a desired area of treatment (e.g., respiratory tract, e.g., upper respiratory tract or lower respiratory tract, e.g., lungs) significantly reduces the likelihood that a patient will experience systemic toxicities associated with some current standards of care.

In another aspect, provided herein is a method for clearing persistent infection in an asymptomatic individual who may or may not have previous COVID-19 illness caused by SARS-COV2, the method comprising administering an effective amount of niclosamide:

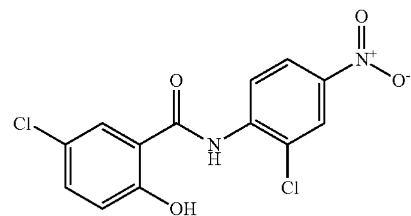 [SMILES: O=C(Nc1ccc([N+](=O)[O-])cc1Cl)c1cc(Cl)ccc1O]

or a pharmaceutically acceptable salt thereof, to the subject.

Accordingly, in some embodiments, the niclosamide compounds (e.g., niclosamide) described herein (e.g., reduced particle size niclosamide compounds (e.g., niclosamide)) can provide targeted delivery of the niclosamide compound (e.g., niclosamide) to certain regions of the respiratory tract (e.g., upper respiratory tract or lower respiratory tract (e.g., lungs)). In some embodiments, administration (e.g., respiratory administration (e.g., via inhalation)) of a niclosamide compound (e.g., niclosamide) described herein to a subject more efficiently produces a local concentration of the niclosamide compound (e.g., niclosamide)

at a site where treatment is needed (e.g., respiratory tract, lower respiratory tract e.g., lungs) of a respiratory infection associated with COVID-19. Moreover, the foregoing can potentially be achieved using a lower dosage with the reduced particle size niclosamide compounds (e.g., niclosamide) described herein.

In some embodiments, the methods and compositions described herein are suitable for use in combination therapy with various other therapeutic regimens.

Embodiments can include one or more of the following features.

The niclosamide compound can have the following formula:

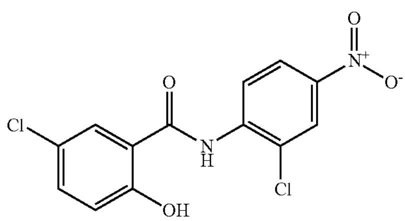 [SMILES: O=C(Nc1ccc([N+](=O)[O-])cc1Cl)c1cc(Cl)ccc1O]

(niclosamide).

The methods as described herein can comprise administering the effective amount of the niclosamide compound, or a pharmaceutically acceptable salt thereof, to the respiratory system of the subject. For example, the methods can comprise locally and/or topically (e.g., locally and topically) administering an effective amount of the niclosamide compound, or a pharmaceutically acceptable salt thereof, to the respiratory system of the subject.

The methods as described herein can comprise administering the effective amount of the niclosamide compound, or a pharmaceutically acceptable salt thereof, to the lungs of the subject. For example, the methods as described herein can comprise locally and/or topically (e.g., locally and topically) administering an effective amount of the niclosamide compound, or a pharmaceutically acceptable salt thereof, to the lungs of the subject.

The methods as described herein can comprise administering a prophylactically effective amount of a niclosamide compound, or a pharmaceutically acceptable salt thereof, to the subject (e.g., locally and/or topically (e.g., to the lungs of the subject)).

The subject can be unresponsive to treatment with remdesivir.

The niclosamide compound, or a pharmaceutically acceptable salt thereof, can be administered by inhalation.

The method can comprise administering (e.g., orally administering) niclosamide.

The niclosamide, or a pharmaceutically acceptable salt thereof (e.g., niclosamide), can be administered by tablet or pill.

The method can comprise orally administering the niclosamide, or a pharmaceutically acceptable salt thereof, as a pharmaceutical composition, wherein the pharmaceutical composition is capable of local delivery to the small intestine.

The method can comprise orally administering the niclosamide, or a pharmaceutically acceptable salt thereof, as a pharmaceutical composition, wherein the pharmaceutical composition is capable of local delivery to the GI tract (e.g., lower GI tract).

The subject can be asymptomatic; or the subject can exhibit one or more symptoms selected from the group consisting of fever, cough, fatigue, shortness of breath, muscle and/or joint pain, sore throat, headache, and/or chills (e.g., fever, cough, and shortness of breath). For example, the one or more symptoms can appear from 2-14 days after the subject's exposure to coronavirus.

The subject can be a human. For example, the subject can be 60 years of age or older; and/or subject can suffer from one or more preexisting medical conditions selected from the group consisting of lung disease, cardiovascular disease, and diabetes. The subject can be an individual that has travelled to an area having confirmed cases of COVID-19 or has been in relatively close contact (e.g., less than 6 feet apart) from such an individual (e.g., a family member or co-worker, commuter, business patron).

The subject can be a subject at risk of developing COVID-19.

The subject at risk of developing COVID-19 can be a healthcare worker (e.g., emergency room physician or nurse, first responder). The subject (e.g., male or female) at risk of developing COVID-19 can be 60 years of age or older (e.g., 65, 70, 75, 80, 85, 90 years of age or older). The subject at risk of developing COVID-19 can suffer from one or more preexisting medical conditions selected from the group consisting of lung disease, cardiovascular disease, and diabetes. The subject at risk of developing COVID-19 can be a resident of an assisted living facility or nursing home, a patient in a hospital for an unrelated treatment (i.e., not related to treatment for COVID-19), or a person incarcerated or working in a prison or jail setting. The subject at risk of developing COVID-19 can be unresponsive to treatment with remdesivir. The subject at risk of developing COVID-19 may have been exposed to the virus or presumed to have been exposed to the virus. The subject can be an individual that has travelled or plans to travel to an area having confirmed cases of COVID-19 or has been or plans to be in relatively close contact (e.g., less than 6 feet apart) from such an individual (e.g., a family member or co-worker, commuter, business patron).

The subject can be 60 years of age or older.

The subject can suffer from one or more preexisting medical conditions selected from the group consisting of lung disease, cardiovascular disease, cancer, colitis, hypertension, and an endocrine disease.

The compound can be administered prior to exposure to the coronavirus or immediately after exposure or presumed exposure to the coronavirus.

The method can further comprise one or more of the following: quarantine, self-quarantine, social distancing, frequent hand washing, and frequent environmental sanitization.

The subject can exhibit a digestive symptom. For example, the subject can exhibit a symptom selected from the group consisting of a lack or loss of appetite, diarrhea, vomiting, abdominal pain, a digestive disease, and combinations thereof. For example, the subject can exhibit a symptom selected from the group consisting of lack or loss of appetite, diarrhea, vomiting, abdominal pain, and combinations thereof. As a non-limiting example, the subject can exhibit a symptom selected from the group consisting of diarrhea.

The subject exhibits no accompanying respiratory symptom.

The subject can exhibit an accompanying respiratory symptom.

The subject can suffer from one or more preexisting medical conditions selected from the group consisting of lung disease, cardiovascular disease, cancer, hypertension, and an endocrine disease. For example, the subject can suffer from, or can be predisposed to suffer from colitis (e.g., an autoimmune colitis; an inflammatory bowel disease; Crohn's disease; iatrogenic autoimmune colitis; or a condition selected from the group consisting of colitis induced by treatment with adoptive cell therapy, colitis associated by one or more alloimmune diseases, collagenous colitis, lymphocytic colitis, c. *difficile* colitis, and microscopic colitis).

The digestive symptom can appears from 2-14 days after the subject's exposure to coronavirus.

The subject can have mild COVID-19. For example, the subject can have: (i) a respiratory rate of ≤30 breaths per min (e.g., <30); (ii) an oxygen saturation at rest of ≥93% (e.g., >93%); and (iii) a ratio of partial pressure of arterial oxygen to fractional concentration of oxygen inspired air of ≥300 mm Hg (e.g., >300). For example, the subject having mild COVID-19 does not have a severe disease complication. The subject can have a low viral load (e.g., a sample (e.g., a nasopharyngeal swab sample, an oropharyngeal swab sample, a sputum sample, a bronchoalveolar lavage sample, a nasopharyngeal aspirate, a nasopharyngeal wash, a nasal aspirate, a nasal wash, or a lower respiratory tract aspirate) from the subject can have a ΔCt of about 3 to about 15).

The subject can have severe COVID-19. For example, the subject can have: at least one of: (i) respiratory distress (i.e., ≥30 breaths per min); (ii) an oxygen saturation at rest of ≤93%; (iii) a ratio of partial pressure of arterial oxygen to fractional concentration of oxygen inspired air of ≤300 mm Hg; and (iv) a severe disease complication. For example, the subject can have high viral load (e.g., a sample (e.g., a nasopharyngeal swab sample, an oropharyngeal swab sample, a sputum sample, a bronchoalveolar lavage sample, a nasopharyngeal aspirate, a nasopharyngeal wash, a nasal aspirate, a nasal wash, or a lower respiratory tract aspirate) from the subject has a ΔCt of about 2 to about −10.

The compound can be administered to the subject at risk of developing COVID-19 prior to exposure to the virus or prior to presumed exposure to the virus (e.g., prior to contact with one or more individuals having or presumed to have COVID-19 and/or prior to contact with one or more articles contaminated with the virus). The compound can be administered immediately after or shortly after exposure or presumed exposure to the virus.

The methods described herein can further comprise one or more of the following: quarantine, self-quarantine, social distancing, frequent hand washing, and frequent environmental sanitization.

The methods herein can further comprises administering a second therapeutic agent. The second therapeutic agent can be an antiviral agent. The second therapeutic agent can be selected from the group consisting of azithromycin, remdesivir, colchicine, hydroxychloroquine, colchicine, and chloroquine.

The niclosamide compound can have a chemical purity of greater than about 99.0%.

The compound can have a reduced particle size range. For example, the compound can have a particle size range of from about 0.1 μm to about 30 μm, such as a particle size range of from about 0.1 μm to about 20 μm (e.g., a particle size range of from about 0.1 μm to about 10 μm).

The compound can have a particle size distribution D(0.9) of from about 1.0 μm to about 15.0 μm, such as a particle size distribution D(0.9) of from about 1.0 μm to about 10.0 μm (e.g., a particle size distribution D(0.9) of from about 6.0 μm to about 8.0 μm; or a particle size distribution D(0.9) of from about 2.2 μm to about 3.2 μm).

The compound can have a particle size distribution D(0.1) of from about 0.1 μm to about 1.5 μm, such as a particle size distribution D(0.1) of from about 0.1 μm to about 1.0 μm (e.g., a particle size distribution D(0.1) of from about 0.3 μm to about 0.9 μm).

The compound can have a particle size distribution D(0.5) of from about 0.5 μm to about 6.0 μm, such as a particle size distribution D(0.5) of from about 1.0 μm to about 4.0 μm (e.g., a particle size distribution D(0.5) of from about 1.0 μm to about 2.0 μm; or a particle size distribution D(0.5) of from about 2.5 μm to about 3.5 μm).

The compound can have a particle size distribution D(0.9) of from about 1.0 μm to about 10.0 μm, a particle size distribution D(0.5) of from about 1.0 μm to about 4.0 μm, and a particle size distribution D(0.1) of from about 0.1 μm to about 1.0 μm.

The compound can have a particle size distribution D(0.9) of from about 6.0 μm to about 8.0 μm, a particle size distribution D(0.5) of from about 1.0 μm to about 4.0 μm, and a particle size distribution D(0.1) of from about 0.3 μm to about 0.9 μm.

The compound can have a particle size distribution D(0.9) of from about 2.2 μm to about 3.2 μm, a particle size distribution D(0.5) of from about 1.0 μm to about 4.0 μm, and a particle size distribution D(0.1) of from about 0.3 μm to about 0.9 μm.

The compound can have a chemical purity of greater than about 99.0%, a particle size distribution D(0.9) of from about 1.0 μm to about 10.0 μm, a particle size distribution D(0.5) of from about 1.0 μm to about 4.0 μm, and a particle size distribution D(0.1) of from about 0.1 μm to about 1.0 μm.

The compound can have a chemical purity of greater than about 99.0%, a particle size distribution D(0.9) of from about 6.0 μm to about 8.0 μm, a particle size distribution D(0.5) of from about 1.0 μm to about 4.0 μm, and a particle size distribution D(0.1) of from about 0.3 μm to about 0.9 μm.

The compound can have a chemical purity of greater than about 99.0%, a particle size distribution D(0.9) of from about 2.2 μm to about 3.2 μm, a particle size distribution D(0.5) of from about 1.0 μm to about 4.0 μm, and a particle size distribution D(0.1) of from about 0.3 μm to about 0.9 μm.

The compound can have a specific surface area of from about 5 $m^2/g$ to about 10 $m^2/g$.

[A1] The compound can have a chemical purity of greater than about 99.0%, a particle size range of from about 0.1 μm to about 30 μm, a particle size distribution D(0.9) of from about 1.0 μm to about 10.0 μm, a particle size distribution D(0.5) of from about 1.0 μm to about 4.0 μm, and a particle size distribution D(0.1) of from about 0.1 μm to about 1.0 μm.

[B1] The compound can have a chemical purity of greater than about 99.0%, a particle size range of from about 0.1 μm to about 30 μm, a particle size distribution D(0.9) of from about 6.0 μm to about 8.0 μm, a particle size distribution D(0.5) of from about 1.0 μm to about 4.0 μm, and a particle size distribution D(0.1) of from about 0.3 μm to about 0.9 μm.

[C1] The compound can have a chemical purity of greater than about 99.0%, a particle size range of from about 0.1 μm to about 30 μm, a particle size distribution D(0.9) of from about 2.2 μm to about 3.2 μm, a particle size distribution D(0.5) of from about 1.0 μm to about 4.0 μm, and a particle size distribution D(0.1) of from about 0.3 μm to about 0.9 μm.

In certain embodiments of [A1], [B1], and/or [C1] supra, the compound has a particle size distribution D(0.5) of from about 2.5 μm to about 3.5 μm.

In certain embodiments of [A1], [B1], and/or [C1] supra, the compound has a particle size distribution D(0.5) of from about 1.0 μm to about 2.0 μm.

In certain embodiments of [A1], [B1], and/or [C1] supra, the compound has a chemical purity of greater than about 99.5%; or a chemical purity of greater than about 99.7%; or a chemical purity of greater than about 99.8%.

In certain embodiments of [A], [B], and/or [C] supra, the compound has a specific surface area of from about 5 $m^2/g$ to about 10 $m^2/g$.

The niclosamide compound can be administered (via respiratory administration) as a pharmaceutical composition, wherein the pharmaceutical composition is capable of local delivery to the respiratory tract. For example, the pharmaceutical composition can comprises one or more pharmaceutically acceptable excipients that chemically and/or structurally predispose the composition for delivery of the niclosamide compound, or a pharmaceutically acceptable salt thereof, to the upper respiratory tract (e.g., nose and nasal passages); and or lower respiratory tract (e.g., the lungs).

For example, the niclosamide compound, or a pharmaceutically acceptable salt thereof can be administered to the nasal cavity of the subject, wherein the niclosamide compound, or a pharmaceutically acceptable salt thereof, is formulated as an intranasal spray, ointment, or gel. As another non-limiting example, the niclosamide compound, or a pharmaceutically acceptable salt thereof can be administered to the lungs of the subject, wherein the niclosamide compound, or a pharmaceutically acceptable salt thereof, is formulated for delivery by inhalation.

The niclosamide compound can be administered (orally or rectally) as a pharmaceutical composition, wherein the pharmaceutical composition is capable of local delivery to the digestive or GI tract. For example, the pharmaceutical composition can comprises one or more pharmaceutically acceptable excipients that chemically and/or structurally predispose the composition for delivery of the niclosamide compound, or a pharmaceutically acceptable salt thereof, to e.g., the lower GI tract or the colon (e.g., ascending colon and/or transverse colon and/or distal colon and/or small intestine (e.g., ileum)).

For example, the niclosamide compound, or a pharmaceutically acceptable salt thereof can be administered to the GI tract of the subject, wherein the niclosamide compound, or a pharmaceutically acceptable salt thereof, is formulated as an oral composition In one aspect, a cocrystal is provided, which includes: (i) niclosamide compound, such as niclosamide or a pharmaceutically acceptable salt and/or hydrate thereof, and (ii) one or more pharmaceutically acceptable coformers. In some embodiments, the cocrystal has a reduced particle size as described anywhere herein. In embodiments, the cocrystal coformers can include any coformers described herein, including second therapeutic agents as described above and anywhere herein.

Definitions

To facilitate understanding of the disclosure set forth herein, a number of terms are defined below. Generally, the nomenclature used herein and the laboratory procedures in organic chemistry, medicinal chemistry, and pharmacology described herein are those well-known and commonly employed in the art. Unless defined otherwise, all technical and scientific terms used herein generally have the same meaning as commonly understood by one of ordinary skill in the art to which this disclosure belongs. Each of the patents, applications, published applications, and other publications that are mentioned throughout the specification and the attached appendices are incorporated herein by reference in their entireties.

The term "niclosamide compound" or "niclosamide compounds" include niclosamide as well as niclosamide analogs described in WO 2017/040864, which is incorporated herein by reference in its entirety. In some embodiments, the niclosamide compound is niclosamide.

"Niclosamide" refers to a compound having the following chemical structure:

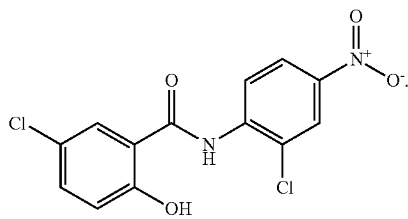

Niclosamide is known by the IUPAC designation: 2'5-dichloro-4'-nitrosalicylanilide and by the CAS designation: CAS: 5-chloro-N-(2-chloro-4-nitrophenyl)-2-hydroxybenzamide Niclosamide has a relatively low water solubility at about from 5-8 mg/L at 20° C., is sparingly soluble in ether, ethanol and chloroform, and is soluble in acetone. The ethanolamine salt dissolves in distilled water 180-280 mg/L at 20° C.

Niclosamide (5-chloro-N-(2-chloro-4-nitrophenyl)-2-hydrobenzamide) is a halogenated salicylanilide that belongs to a group of medicines known as anthelmintics. Anthelmintics are medicines used in the treatment of worm infections. Niclosamide, which has low systemic bioavailabilty and an excellent safety profile, is used to treat broad or fish tapeworm, dwarf tapeworm, and beef tapeworm infections. It is believed that niclosamide inhibits oxidative phosphorylation and stimulates adenosine triphosphatase activity in the mitochondria of cestodes (e.g., tapeworm), killing the scolex and proximal segments of the tapeworm both in vitro and in vivo (see, Li, Y., et al., *Cancer Lett.* 2014 349, 8-14.).

Niclosamide is available in a various salt or solvated forms. These include, but are not limited to, the ethanolamine salt known by the IUPAC designation 5-chloro-salicyl-2-chloro-4-nitro) anilide 2-aminoethanol salt or the CAS designation 5-chloro-N-(2-chloro-4-nitrophenyl)-2-hydroxybenzamide with 2-aminoethanol (1:1)—see, e.g., US 2013/0231312; the piperazine salt known by the IUPAC designation 5-chloro-salicyl-(2-chloro-4-nitro) anilide piperazine salt or the CAS designation 5-chloro-N-choro-(2-chloro-4-nitrophenyl)-2-hydroxybenzamide with piperazine (2:1); and niclosamide monohydrate known by the IUPAC designation 5-chlorosalicyl-(4-chloro-4-nitro) anilide monohydrate or the CAS designation 5-choro-N-(2-choro-4-nitrophenyl)-2-hydroxybenzamide with monohydrate (1:1).

Niclosamide is commercially available in a variety of formulations including, but not limited to BAYER 73®, BAYER 2353, BAYER 25 648®, BAYILUSCID®, BAY- LUSCIDE®, CESTOCID®, CLONITRALID, DICHLOSALE®, FENASAL®, HL 2447®, IOMESAN®, IOMEZAN®, LINTEX®, MANOSIL®, NASEMO®, NICLOSAMID®, PHENASAL®, TREDEMINE®, SULQUI®, VERMIIID®, VERMITIN®, YOMESAN®, and the like.

The terms "respiratory tract" and "respiratory system" refer to the organs that are involved in breathing: nose, throat, larynx, trachea, bronchi, and lungs.

The term "lower respiratory tract" refers to the part of the respiratory system including the portion of the larynx below the vocal folds, trachea, bronchi, and lungs.

The term "upper respiratory tract" refers to the part of the respiratory system including the nose and nasal passages, paranasal sinuses, the pharynx, and the portion of the larynx above the vocal folds (cords).

The term "acceptable" with respect to a formulation, composition or ingredient, as used herein, means having no persistent detrimental effect on the general health of the subject being treated.

"API" refers to an active pharmaceutical ingredient (e.g., niclosamide compound, e.g., niclosamide).

The terms "effective amount" or "therapeutically effective amount," as used herein, refer to a sufficient amount of a chemical entity (e.g., a compound exhibiting activity as a mitochondrial uncoupling agent or a pharmaceutically acceptable salt and/or hydrate and/or cocrystal thereof; e.g., a compound, such as niclosamide or a pharmaceutically acceptable salt and/or hydrate and/or cocrystal thereof, e.g., a compound, such as a niclosamide analog, or a pharmaceutically acceptable salt and/or hydrate and/or cocrystal thereof) being administered which will relieve to some extent one or more of the symptoms of the disease or condition being treated. The result includes reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case is determined using any suitable technique, such as a dose escalation study.

The term "excipient" or "pharmaceutically acceptable excipient" means a pharmaceutically-acceptable material, composition, or vehicle, such as a liquid or solid filler, diluent, carrier, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, e.g., *Remington: The Science and Practice of Pharmacy,* 21*st ed*.; Lippincott Williams & Wilkins: Philadelphia, Pa., 2005*; Handbook of Pharmaceutical Excipients,* 6*th ed*.; Rowe et al., Eds.; The Pharmaceutical Press and the American Pharmaceutical Association: 2009*; Handbook of Pharmaceutical Additives,* 3*rd ed*.; Ash and Ash Eds.; Gower Publishing Company: 2007*; Pharmaceutical Preformulation and Formulation,* 2*nd ed*.; Gibson Ed.; CRC Press LLC: Boca Raton, Fla., 2009.

The term "pharmaceutically acceptable salt" refers to a formulation of a compound that does not cause significant irritation to an organism to which it is administered and does not abrogate the biological activity and properties of the compound. In certain instances, pharmaceutically acceptable salts are obtained by reacting a compound described herein, with acids such as hydrochloric acid, hydrobromic acid, sulfuric acid, nitric acid, phosphoric acid, methanesulfonic acid, ethanesulfonic acid, p-toluenesulfonic acid, salicylic acid and the like. In some instances, pharmaceutically acceptable salts are obtained by reacting a compound having acidic group described herein with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, and salts with amino acids such as arginine, lysine, and the like, or by other methods previously determined. The pharmacologically acceptable salt is not specifically limited as far as it can be used in medicaments. Examples of a salt that the compounds described herein form with a base include the following: salts thereof with inorganic bases such as sodium, potassium, magnesium, calcium, and aluminum; salts thereof with organic bases such as methylamine, ethylamine and ethanolamine; salts thereof with basic amino acids such as lysine and ornithine; and ammonium salt. The salts may be acid addition salts, which are specifically exemplified by acid addition salts with the following: mineral acids such as hydrochloric acid, hydrobromic acid, hydroiodic acid, sulfuric acid, nitric acid, and phosphoric acid:organic acids such as formic acid, acetic acid, propionic acid, oxalic acid, malonic acid, succinic acid, fumaric acid, maleic acid, lactic acid, malic acid, tartaric acid, citric acid, methanesulfonic acid, and ethanesulfonic acid; acidic amino acids such as aspartic acid and glutamic acid.

The term "pharmaceutical composition" refers to a mixture of a compound described herein with other chemical components (referred to collectively herein as "excipients"), such as carriers, stabilizers, diluents, dispersing agents, suspending agents, and/or thickening agents. The pharmaceutical composition facilitates administration of the compound to an organism.

The term "subject" refers to an animal, including, but not limited to, a primate (e.g., human), monkey, cow, pig, sheep, goat, horse, dog, cat, rabbit, rat, or mouse. The terms "subject" and "patient" are used interchangeably herein in reference, for example, to a mammalian subject, such as a human.

The terms "treat," "treating," and "treatment," in the context of treating a disease or disorder, are meant to include alleviating or abrogating a disorder, disease, or condition, or one or more of the symptoms associated with the disorder, disease, or condition; or to slowing the progression, spread or worsening of a disease, disorder or condition or of one or more symptoms thereof. Often, the beneficial effects that a subject derives from a therapeutic agent do not result in a complete cure of the disease, disorder or condition. In some embodiments, the terms "treat," "treating," and "treatment," include virologically curing a viral disorder, disease, or condition; reducing viral shedding; decreasing viral RNA load (e.g., a measured by PCR); reducing the length of stay in a hospital; reducing the length of stay in an infectious disease unit and/or intensive care unit; or slowing (including stopping) the progression/development of respiratory (or other serious) symptoms.

The details of one or more embodiments of the invention are set forth in the description below. Other features, objects, and advantages of the invention will be apparent from the description and drawings, and from the claims.

DETAILED DESCRIPTION

This disclosure features niclosamide compounds (or pharmaceutically acceptable salts and/or co-crystals thereof, e.g., niclosamide), having one or more properties that include, but are not limited to: a particular purity (e.g., a chemical purity of greater than about 99.0%) or a particular particle size (e.g., a particular particle size distribution and/or a particular particle size range and/or a specific surface area range) which are useful e.g., in the treatment of infections caused by coronaviruses (e.g., treatment of COVID-19). In an aspect, the niclosamide compounds described herein (e.g., niclosamide) can form part of compositions, dosage forms (e.g., unit dosage forms), and the like, which are suitable for respiratory administration (e.g., inhalation). This disclosure also features methods of making and using the same.

Methods of Treatment

In one aspect, provided herein is a method for treating COVID-19 in a subject in need thereof, the method comprising administering an effective amount of a niclosamide compound, or a pharmaceutically acceptable salt thereof, to the subject.

In some embodiments of the methods herein, the subject is asymptomatic.

In some embodiments of the methods herein, the subject exhibits one or more symptoms selected from the group consisting of fever, cough, fatigue, shortness of breath (dyspnea), muscle and/or joint pain, sore throat, headache, conjunctivitis, diarrhea, lack or loss of appetite, vomiting, abdominal pain, and/or chills. In certain of these embodiments, the subject exhibits one or more symptoms selected from the group consisting of fever, cough, and shortness of breath. In some embodiments, the subject exhibits one or more digestive symptoms (e.g., extra-pulmonary symptoms) selected from the group consisting of diarrhea, lack or loss of appetite, vomiting, and abdominal pain.

COVID-19 may cause digestive symptoms for several reasons. For example, SARS-CoV-2 can invade the human body by binding to the human angiotensin converting enzyme 2 (ACE-2) receptor, which can liver tissue injury; SARS-CoV-2 can indirectly or directly damage the digestive system through an inflammatory response; SARS-CoV-2 may cause disorders of the intestinal flora; and changes in the composition and function of the digestive tract flora can affect the respiratory tract through the common mucosal immune system, and respiratory tract flora disorders also affect the digestive tract through immune regulation (e.g., SARS-CoV-2 may affect the gut-lung axis). See, e.g., Pan et al. Clinical Characteristics of COVID-19 Patients with Digestive Symptoms in Hubei, China: A Descriptive, Cross-Sectional, Multicenter Study. *Am. J. Gastroenterol* 2020 Mar. 19[EPub Ahead of Print].

Accordingly, also provided herein is a method for treating one or more digestive symptoms in a subject having COVID-19, the method comprising administering an effective amount of a niclosamide compound, or a pharmaceutically acceptable salt thereof, to the subject. In some embodiments, the one or more digestive symptoms are the result of autoimmune colitis. For example, the autoimmune colitis can be the result of inflammation in the GI tract. In some embodiments, the autoimmune colitis is the result of overresponsiveness and/or hyperreactivity of the subject's immune system to SARS-CoV-2.

In some embodiments of the methods herein, the one or more symptoms appear from 2-14 (e.g., 2-3 days, 4-5 days, 6-10 days, or 11-14 days) days after the subject's exposure to coronavirus.

In some embodiments, the subject is a subject at risk. In certain embodiments, the subject is 60 years of age or older. In certain embodiments, the subject suffers from one or more preexisting medical conditions selected from the group consisting of lung disease, cardiovascular disease, and diabetes. In certain embodiments, the subject is unresponsive to treatment with remdesivir.

In another aspect, provided herein is a method of reducing the risk of developing COVID-19 in a subject at risk thereof, the method comprising administering an effective amount (e.g., a prophylactically effective amount) of a niclosamide compound, or a pharmaceutically acceptable salt thereof, to the subject.

In certain embodiments, the subject at risk of developing COVID-19 is a healthcare worker (e.g., emergency room physician or nurse, first responder).

In certain embodiments, the subject at risk of developing COVID-19 is 60 years of age or older.

In certain embodiments, the subject at risk of developing COVID-19 suffers from one or more preexisting medical conditions selected from the group consisting of lung disease, cardiovascular disease, and diabetes.

In certain embodiments, the subject at risk of developing COVID-19 is a resident of an assisted living facility or nursing home, a patient in a hospital for an unrelated treatment (i.e., not related to treatment for COVID-19), or a person incarcerated or working in a prison or jail setting.

In certain embodiments, the subject at risk of developing COVID-19 is unresponsive to treatment with remdesivir.

In certain embodiments, the subject at risk of developing COVID-19 has been exposed to the virus or presumed to have been exposed to the virus.

In certain embodiments, the compound is administered prior to exposure to the virus or prior to presumed exposure to the virus (e.g., prior to contact with one or more individuals having or presumed to have COVID-19 and/or prior to contact with one or more articles contaminated with the virus). For example, the compound can be administered immediately after or shortly after exposure or presumed exposure to the virus.

In another aspect, provided herein is a method for treating COVID-19 in a subject in need thereof, the method comprising orally administering an effective amount of niclosamide:

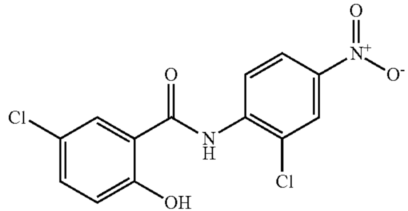 [SMILES: O=C(Nc1ccc([N+](=O)[O-])cc1Cl)c1cc(Cl)ccc1O]

or a pharmaceutically acceptable salt thereof, to the subject.

In certain of these embodiments, the method comprises administering niclosamide.

In certain embodiments, subject exhibits a digestive symptom. In certain embodiments, the subject exhibits a symptom selected from the group consisting of a lack or loss of appetite, diarrhea, vomiting, abdominal pain, a digestive disease, and combinations thereof. In certain embodiments, the subject exhibits a symptom selected from the group consisting of lack or loss of appetite, diarrhea, vomiting, abdominal pain, and combinations thereof. As a non-limiting example of the foregoing embodiments, the subject exhibits a symptom selected from the group consisting of diarrhea.

In certain embodiments, the subject does not exhibit an accompanying respiratory symptom. In certain other embodiments, subject exhibits an accompanying respiratory symptom.

In certain embodiments, the subject suffers from one or more preexisting medical conditions selected from the group consisting of lung disease, cardiovascular disease, cancer, hypertension, and an endocrine disease.

In certain embodiments, the subject suffers from, or is predisposed to suffer from colitis.

In certain embodiments, the colitis is an autoimmune colitis. In certain embodiments, the colitis is an inflammatory bowel disease. In certain embodiments, the colitis is ulcerative colitis or Crohn's disease. In certain embodiments, the colitis is iatrogenic autoimmune colitis. In certain embodiments, the colitis is selected from the group consisting of colitis induced by treatment with adoptive cell therapy, colitis associated by one or more alloimmune diseases, collagenous colitis, lymphocytic colitis, c. *difficile* colitis, and microscopic colitis.

In certain embodiments when the subject exhibits a digestive symptom, the digestive symptom appears from 2-14 (e.g., 2-3, 4-5, 6-7, 8-10, or 11-14) days after the subject's exposure to coronavirus.

In certain embodiments, the method further comprises administering a second therapeutic agent. As a non-limiting example of the foregoing embodiments, the second therapeutic agent is selected from the group consisting of azithromycin, remdesivir, hydroxychloroquine, colchicine, and chloroquine.

In certain embodiments, the niclosamide, or a pharmaceutically acceptable salt thereof, is administered by tablet or pill.

In certain embodiments, the method comprises orally administering the niclosamide, or a pharmaceutically acceptable salt thereof, as a pharmaceutical composition, wherein the pharmaceutical composition is capable of local delivery to the GI tract (e.g., lower GI tract).

In certain embodiments, the method comprises orally administering the niclosamide, or a pharmaceutically acceptable salt thereof, as a pharmaceutical composition, wherein the pharmaceutical composition is capable of local delivery to the colon.

In certain embodiments, the method comprises orally administering the niclosamide, or a pharmaceutically acceptable salt thereof, as a pharmaceutical composition, wherein the pharmaceutical composition is capable of local delivery to the small intestine.

In another aspect, the disclosure features a method of preventing (e.g., reducing the risk of developing) COVID-19 in a subject (e.g., a human) at risk thereof, the method comprising administering an effective amount of niclosamide:

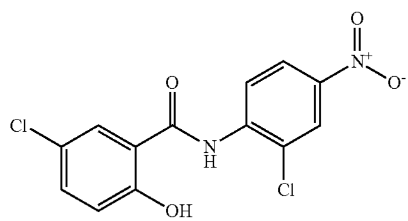 [SMILES: O=C(Nc1ccc([N+](=O)[O-])cc1Cl)c1cc(Cl)ccc1O]

or a pharmaceutically acceptable salt thereof, to the subject (e.g., the human).

In certain of these embodiments, subject is selected from the group consisting of a healthcare worker, a resident of an assisted living facility or nursing home, a patient in a hospital for an unrelated treatment, and a person incarcerated or working in a prison or jail setting. In certain embodiments, the subject is 60 years of age or older. In certain embodiments, the subject suffers from one or more preexisting medical conditions selected from the group consisting of lung disease, cardiovascular disease, cancer, colitis, hypertension, and an endocrine disease. In certain embodiments, the compound is administered prior to exposure to the coronavirus or immediately after exposure or presumed exposure to the coronavirus.

In another aspect, the disclosure features a method for clearing persistent infection in an asymptomatic individual who may or may not have previous COVID-19 illness caused by SARS-COV2, the method comprising administering an effective amount of niclosamide:

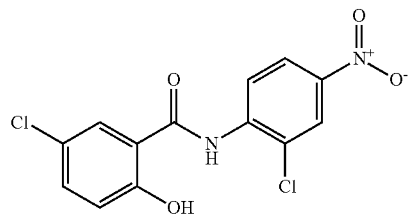 [SMILES: O=C(Nc1ccc([N+](=O)[O-])cc1Cl)c1cc(Cl)ccc1O]

or a pharmaceutically acceptable salt thereof, to the subject.

In some embodiments, the methods described herein further comprise one or more of the following: quarantine, self-quarantine, social distancing, frequent handwashing, and frequent environmental sanitization.

In some embodiments of the methods described herein, the subject is a human.

In some embodiments, the methods described herein comprise administering the effective amount of the niclosamide compound, or a pharmaceutically acceptable salt thereof, to the respiratory system of the subject.

In certain embodiments, the methods described herein comprise locally administering an effective amount of the niclosamide compound, or a pharmaceutically acceptable salt thereof, to the respiratory system of the subject.

In certain embodiments, the methods described herein comprise topically administering an effective amount of the niclosamide compound, or a pharmaceutically acceptable salt thereof, to the respiratory system of the subject.

In certain of the foregoing embodiments, the methods described herein comprise locally and topically administering an effective amount of the niclosamide compound, or a pharmaceutically acceptable salt thereof, to the respiratory system of the subject.

In some embodiments, the methods described herein comprise administering the effective amount of the niclosamide compound, or a pharmaceutically acceptable salt thereof, to the lungs of the subject.

In certain embodiments, the methods described herein comprise locally administering an effective amount of the niclosamide compound, or a pharmaceutically acceptable salt thereof, to the lungs of the subject.

In certain embodiments, the methods described herein comprise topically administering an effective amount of the niclosamide compound, or a pharmaceutically acceptable salt thereof, to the lungs of the subject.

In certain embodiments, the methods described herein comprise locally and topically administering an effective amount of the niclosamide compound, or a pharmaceutically acceptable salt thereof, to the lungs of the subject.

In certain embodiments of the methods described herein, the niclosamide compound, or a pharmaceutically acceptable salt thereof, is administered by inhalation.

In another aspect, provided herein is a method for treating COVID-19 in a subject in need thereof, the method comprising administering an effective amount of a niclosamide compound, or a pharmaceutically acceptable salt thereof, to the GI tract of the subject.

In certain embodiments, the method comprises locally administering an effective amount of the niclosamide compound, or a pharmaceutically acceptable salt thereof to the GI tract of the subject.

In certain embodiments, the method comprises topically administering an effective amount of the niclosamide compound, or a pharmaceutically acceptable salt thereof to the GI tract of the subject.

In certain of these embodiments, the niclosamide compound, or a pharmaceutically acceptable salt thereof, is administered by rectal administration. As a non-limiting example of the foregoing embodiments, the niclosamide compound, or a pharmaceutically acceptable salt thereof, is administered by enema, rectal gel, rectal foam, rectal aerosol, or suppository. For example, the niclosamide compound, or a pharmaceutically acceptable salt thereof, can be administered by enema.

In some embodiments, the method comprises orally administering the niclosamide compound, or a pharmaceutically acceptable salt thereof, as a pharmaceutical composition, wherein the pharmaceutical composition is capable of local delivery to the digestive or GI tract. In certain of these embodiments, the pharmaceutical composition comprises one or more pharmaceutically acceptable excipients that chemically and/or structurally predispose the composition for delivery of the niclosamide compound, or a pharmaceutically acceptable salt thereof, to the lower GI tract. For example, the composition comprises one or more pharmaceutically acceptable excipients that chemically and/or structurally predispose the composition for delivery of the niclosamide compound, or a pharmaceutically acceptable salt thereof, to the colon. As another non-limiting example, the composition comprises one or more pharmaceutically acceptable excipients that chemically and/or structurally predispose the composition for delivery of the niclosamide, or a pharmaceutically acceptable salt thereof, to the ascending colon and/or transverse colon and/or distal colon. As another non-limiting example, the composition comprises one or more pharmaceutically acceptable excipients that chemically and/or structurally predispose the composition for delivery of niclosamide, or a pharmaceutically acceptable salt thereof, to the small intestine (e.g., to the ileum).

The methods disclosed herein can further comprise a step of identifying a subject having COVID-19. Identification of a subject as having COVID-19 can include the detection of RNA from severe acute respiratory syndrome coronavirus 2 (SARS-CoV-2) in a biological sample from the subject. In some embodiments, the biological sample is a respiratory sample. Non-limiting examples of respiratory samples that can be used to detect SARS-CoV-2 include a nasopharyngeal swab sample, an oropharyngeal swab sample, a sputum sample, a bronchoalveolar lavage sample, a nasopharyngeal aspirate, a nasopharyngeal wash, a nasal aspirate, a nasal wash, and a lower respiratory tract aspirate. In some embodiments, the biological sample is a fecal sample and/or an anal/rectal swab sample. In some embodiments, polymerase chain reaction (PCR) is used to detect RNA from SARS-CoV-2 in a sample from a subject. Non-limiting examples of types of PCR that can be used to identify a subject as having COVID-19 include reverse transcription PCR (RT-PCR), real-time PCR (e.g., quantitative PCR (qPCR)), and real-time RT-PCR (rRT-PCR). In some embodiments, a specific gene from SARS-CoV-2 is detected. For example, the E gene, RNA-dependent RNA polymerase gene (RdRp) gene, ORF1a gene, ORF1b gene, N gene, or a combination thereof can be detected using primers or probes specific to the gene or a portion thereof. In some embodiments, detection of RNA from SARS-CoV-2 can include using a kit comprising, for example, PCR reagents and primers and/or probes for detecting RNA from SARS-CoV-2 (e.g., primers and/or probes specific to the E gene, RNA-dependent RNA polymerase gene (RdRp) gene, ORF1a gene, ORF1b gene, N gene, or a combination thereof). Many commercial kits are available to detect RNA from SARS-CoV-2. Non-limiting examples of such kits include PowerChek™ 2019-nCov RT-PCR kit (Kogene Biotech), RT-PCR Allplex 2019-nCoV Assay (Seegene); STANDARD M n-CoV Real-Time Detection Kit (SD Biosensor); rRT-PCR XPERT® Xpress SARS-CoV-2 (Cepheid Innovation); and Primerdesign Ltd COVID-19 GENESIG® Real-Time PCR assay. See also, the kits approved by the Food and Drug Administration (fda.gov/medical-devices/emergency-situations-medical-devices/emergency-use-authorizations#covid19ivd).

In some embodiments, the E gene and RdRp gene specific to SARS-CoV-2 is detected (see, e.g., PowerChek™ 2019-nCov RT-PCR kit; RT-PCR Allplex 2019-nCoV Assay; and STANDARD M n-CoV Real-Time Detection Kit (SD Biosensor)). In some embodiments, the ORF1a gene and N gene are detected (see, e.g., DiaPlexQ™ Novel Coronavirus Detection Kit (2019-nCoV) (SolGent Co., Ltd.)) In some embodiments, the RdRP gene, E gene, and N gene are detected (see, e.g., Corman et al. Eurosurveillance, 25, 2000045 (2020)). In some embodiments, the ORF1 ab genome region is detected (see, e.g., Primerdesign Ltd COVID-19 GENESIG® Real-Time PCR assay). In some embodiments, the N2 gene and E gene are detected (see, e.g., rRT-PCR XPERT® Xpress SARS-CoV-2 (Cepheid Innovation)). In some embodiments, primers and probes to detect the RdRp gene spanning nucleotides 12621-12727 and 14010-14116 (positions according SARS-CoV, NC_004718) can be used to detect SARS-CoV-2. See, e.g. the World Health Organization Protocol from the National Reference Center for Respiratory Viruses, Institut Pasteur, Paris (www.who.int/docs/default-source/coronaviruse/real-time-rt-pcr-assays-for-the-detection-of-sars-cov-2-institut-pasteur-paris.pdf?sfvrsn=3662fcb6_2). In some embodiments, a first gene is detected in a screening test and a second gene is detected for confirmation. For example, the N gene from SARS-CoV-2 can be detected in a screening assay and ORF1b from SARS-CoV-2 can be detected as a confirmatory assay.

In some embodiments, rRT-PCR can be used to monitor a subject with COVID-19. For example, prior to starting a therapy as described herein (e.g., a niclosamide compound, or a pharmaceutically acceptable salt thereof as described herein), a biological sample can be obtained from the subject and the level of SARS-CoV-2 RNA (e.g., the level of RNA corresponding to an SARS-CoV-2 gene described herein) determined in the biological sample. This sample can be considered a base-line sample. The subject can then be administered one or more doses of a therapy as described herein (e.g., a niclosamide compound, or a pharmaceutically acceptable salt thereof as described herein) and the levels of SARS-CoV-2 RNA can be monitored (e.g., after the first dose, second dose, third dose, etc. or after one week, two weeks, three weeks, four weeks, etc.). If the level of SARS-CoV-2 RNA is lower than the baseline sample (e.g., a 1% to about a 99% reduction, a 1% to about a 95% reduction, a 1% to about a 90% reduction, a 1% to about a 85% reduction, a 1% to about a 80% reduction, a 1% to about a 75% reduction, a 1% reduction to about a 70% reduction, a 1% reduction to about a 65% reduction, a 1% reduction to about a 60% reduction, a 1% reduction to about a 55% reduction, a 1% reduction to about a 50% reduction, a 1% reduction to about a 45% reduction, a 1% reduction to about a 40% reduction, a 1% reduction to about a 35% reduction, a 1% reduction to about a 30% reduction, a 1% reduction to about a 25% reduction, a 1% reduction to about a 20% reduction, a 1% reduction to about a 15% reduction, a 1% reduction to about a 10% reduction, a 1% to about a 5% reduction, about a 5% to about a 99% reduction, about a 10% to about a 99% reduction, about a 15% to about a 99% reduction, about a 20% to about a 99% reduction, about a 25% to about a 99% reduction, about a 30% to about a 99% reduction, about a 35% to about a 99% reduction, about a 40% to about a 99% reduction, about a 45% to about a 99% reduction, about a 50% to about a 99% reduction, about a 55% to about a 99% reduction, about a 60% to about a 99% reduction, about a 65% to about a 99% reduction, about a 70% to about a 99% reduction, about a 75% to about a 95% reduction, about a 80% to about a 99% reduction, about a 90% reduction to about a 99% reduction, about a 95% to about a 99% reduction, about a 5% to about a 10% reduction, about a 5% to about a 25% reduction, about a 10% to about a 30% reduction, about a 20% to about a 40% reduction, about a 25% to about a 50% reduction, about a 35% to about a 55% reduction, about a 40% to about a 60% reduction, about a 50% reduction to about a 75% reduction, about a 60% reduction to about 80% reduction, or about a 65% to about a 85% reduction etc.), this is indicative of responsiveness to therapy. In some embodiments, the level of SARS-CoV-2 RNA in a biological sample obtained from the subject (n) is compared to the sample taken just previous (n−1). If the level of SARS-CoV-2 RNA in the n sample is lower than the n−1 sample (e.g., a 1% to about a 99% reduction, a 1% to about a 95% reduction, a 1% to about a 90% reduction, a 1% to about a 85% reduction, a 1% to about a 80% reduction, a 1% to about a 75% reduction, a 1% reduction to about a 70% reduction, a 1% reduction to about a 65% reduction, a 1% reduction to about a 60% reduction, a 1% reduction to about a 55% reduction, a 1% reduction to about a 50% reduction, a 1% reduction to about a 45% reduction, a 1% reduction to about a 40% reduction, a 1% reduction to about a 35% reduction, a 1% reduction to about a 30% reduction, a 1% reduction to about a 25% reduction, a 1% reduction to about a 20% reduction, a 1% reduction to about a 15% reduction, a 1% reduction to about a 10% reduction, a 1% to about a 5% reduction, about a 5% to about a 99% reduction, about a 10% to about a 99% reduction, about a 15% to about a 99% reduction, about a 20% to about a 99% reduction, about a 25% to about a 99% reduction, about a 30% to about a 99% reduction, about a 35% to about a 99% reduction, about a 40% to about a 99% reduction, about a 45% to about a 99% reduction, about a 50% to about a 99% reduction, about a 55% to about a 99% reduction, about a 60% to about a 99% reduction, about a 65% to about a 99% reduction, about a 70% to about a 99% reduction, about a 75% to about a 95% reduction, about a 80% to about a 99% reduction, about a 90% reduction to about a 99% reduction, about a 95% to about a 99% reduction, about a 5% to about a 10% reduction, about a 5% to about a 25% reduction, about a 10% to about a 30% reduction, about a 20% to about a 40% reduction, about a 25% to about a 50% reduction, about a 35% to about a 55% reduction, about a 40% to about a 60% reduction, about a 50% reduction to about a 75% reduction, about a 60% reduction to about 80% reduction, or about a 65% to about a 85% reduction, etc.), this is indicative of responsiveness to therapy. In the case of responsiveness to therapy, the subject can to be administered one or more doses of therapy (e.g., a niclosamide compound, or a pharmaceutically acceptable salt thereof) and the SARS-CoV-2 RNA can be continued to be monitored.

In some embodiments, COVID-19 can be severe or mild. See, e.g, Liu et al. Lancet Infect. Dis. 2020; doi.org/10.1016/S1473-3099(20)30232-2. Also provided herein are methods for treating mild COVID-19 in a subject in need thereof, the method comprising administering an effective amount of a niclosamide compound, or a pharmaceutically acceptable salt thereof, to the subject. In some embodiments, a subject having mild COVID-19 has: (i) a respiratory rate of <30 breaths per min; (ii) an oxygen saturation at rest of >93%; and (iii) a ratio of partial pressure of arterial oxygen to fractional concentration of oxygen inspired air of >300 mm Hg. In some embodiments, a subject having mild COVID-19 does not have a severe disease complication. Severe disease complications can include, but are not limited to, respiratory failure, requirement of mechanical ventilation, septic shock, and non-respiratory organ failure. In some embodiments, a subject having mild COVID-19 does not have digestive symptoms. For example, the subject does not have diarrhea, abdominal pain, or vomiting. In some embodiments, a subject having mild COVID-19 has a low viral load. Viral load can be estimated using the ΔCt method ($Ct_{sample}-Ct_{ref}$). In some embodiments, a sample from a subject with a low viral load has a ΔCt>3. For example, a sample from a subject with a low viral load can have a ΔCt of about 3 to about 15. In some embodiments, the niclosamide compound, or a pharmaceutically acceptable salt thereof, is administered in combination with one or more additional therapeutic agents (e.g., any of the additional therapeutic agents described herein).

Also provided herein are methods for treating severe COVID-19 in a subject in need thereof, the method comprising administering an effective amount of a niclosamide compound, or a pharmaceutically acceptable salt thereof, to the subject. In some embodiments, a subject having severe COVID-19 has at least one of: (i) respiratory distress (i.e., ≥30 breaths per min); (ii) an oxygen saturation at rest of ≤93%; (iii) a ratio of partial pressure of arterial oxygen to fractional concentration of oxygen inspired air of ≤300 mm Hg; and (iv) a severe disease complication, e.g., a severe disease complication as described herein. In some embodiments, a subject having severe COVID-19 has one or more digestive symptoms. For example, the subject has one or more of diarrhea, abdominal pain, and vomiting. In some embodiments, a subject having severe COVID-19 has one or more of an elevated liver enzyme level, lower monocyte count, and longer prothrombin time. For example, an elevated liver enzyme level can include an AST or ALT level of >50 U/L. In some embodiments, a subject having severe COVID-19 has a high viral load. In some embodiments, a sample from a subject with a high viral load has a ΔCt≤2. For example, a sample from a subject with a low viral load can have a ΔCt of about 2 to about −10. In some embodiments, the niclosamide compound, or a pharmaceutically acceptable salt thereof, is administered in combination with one or more additional therapeutic agents (e.g., any of the additional therapeutic agents described herein). Also provided herein are methods for treating mild COVID-19 in a subject in need thereof, the method comprising administering an effective amount of a niclosamide compound, or a pharmaceutically acceptable salt thereof, to the nasal cavity of the subject. In some embodiments, a subject having mild COVID-19 has: (i) a respiratory rate of ≤30 breaths per min; (ii) an oxygen saturation at rest of ≥93%; and (iii) a ratio of partial pressure of arterial oxygen to fractional concentration of oxygen inspired air of ≥300 mm Hg. In some embodiments, the subject does not have a severe disease complication. In some embodiments, the subject having mild COVID-19 has a low viral load (e.g., a ΔCt of about 3 to about 15). In some embodiments, the niclosamide compound, or a pharmaceutically acceptable salt thereof, is formulated as an intranasal spray, ointment, or gel (e.g., any of the intranasal compositions described herein).

Also provided herein are methods of treating a subject having COVID-19 that include: identifying a subject that has: (i) a respiratory rate of <30 breaths per min; (ii) an oxygen saturation at rest of >93%; and (iii) a ratio of partial pressure of arterial oxygen to fractional concentration of oxygen inspired air of >300 mm Hg; and administering to the nasal cavity of the identified subject a treatment that includes a niclosamide compound, or a pharmaceutically acceptable salt thereof. In some embodiments, the subject does not have a severe disease complication. In some embodiments, the subject has a low viral load (e.g., a ΔCt of about 3 to about 15). In some embodiments, the niclosamide compound, or a pharmaceutically acceptable salt thereof, is formulated as an intranasal spray, ointment, or gel (e.g., any of the intranasal compositions described herein).

Also provided herein are methods for treating severe COVID-19 in a subject in need thereof, the method comprising administering an effective amount of a niclosamide compound, or a pharmaceutically acceptable salt thereof, to the lungs of the subject. In some embodiments, a subject having severe COVID-19 has at least one of: (i) respiratory distress (i.e., ≥30 breaths per min); (ii) an oxygen saturation at rest of ≤93%; (iii) a ratio of partial pressure of arterial oxygen to fractional concentration of oxygen inspired air of ≤300 mm Hg; and (iv) a severe disease complication, e.g., a severe disease complication as described herein. In some embodiments, the subject has one or more digestive symptoms (e.g., any of the digestive symptoms described herein). In some embodiments, the subject has one or more of an elevated liver enzyme level, lower monocyte count, and a longer prothrombin time. In some embodiments, the subject has a high viral load (e.g., a ΔCt of about 2 to about −10). In some embodiments, the niclosamide compound, or a pharmaceutically acceptable salt thereof, is formulated for delivery by inhalation (e.g., any of the compositions for inhalation described herein).

Also provided herein are methods of treating a subject having COVID-19 that include: identifying a subject that has at least one of (i) respiratory distress (i.e., ≥30 breaths per min); (ii) an oxygen saturation at rest of ≤93%; (iii) a ratio of partial pressure of arterial oxygen to fractional concentration of oxygen inspired air of ≤300 mm Hg; and (iv) a severe disease complication, e.g., a severe disease complication as described herein; and administering to the lungs of the identified subject a treatment that includes a niclosamide compound, or a pharmaceutically acceptable salt thereof. In some embodiments, the subject has one or more digestive symptoms (e.g., any of the digestive symptoms described herein). In some embodiments, the subject has one or more of an elevated liver enzyme level, lower monocyte count, and a longer prothrombin time. In some embodiments, the subject has a high viral load (e.g., a ΔCt of about 2 to about −10). In some embodiments, the niclosamide compound, or a pharmaceutically acceptable salt thereof, is formulated for delivery by inhalation (e.g., any of the compositions for inhalation described herein).

Also provided herein are methods for treating severe COVID-19 in a subject in need thereof, the method comprising administering an effective amount of a niclosamide compound, or a pharmaceutically acceptable salt thereof, to the GI tract of the subject. In some embodiments, a subject having severe COVID-19 has at least one of: (i) respiratory distress (i.e., ≥30 breaths per min); (ii) an oxygen saturation at rest of ≤93%; (iii) a ratio of partial pressure of arterial oxygen to fractional concentration of oxygen inspired air of ≤300 mm Hg; and (iv) a severe disease complication, e.g., a severe disease complication as described herein. In some embodiments, the subject has one or more digestive symptoms (e.g., any of the digestive symptoms described herein). In some embodiments, the subject has one or more of an elevated liver enzyme level, lower monocyte count, and a longer prothrombin time. In some embodiments, the subject has a high viral load (e.g., a ΔCt of about 2 to about −10). In some embodiments, the niclosamide compound, or a pharmaceutically acceptable salt thereof, is formulated for oral delivery.

Also provided herein are methods of treating a subject having COVID-19 that include: (a) identifying a subject having (i) a respiratory rate of <30 breaths per min; (ii) an oxygen saturation at rest of >93%; and (iii) a ratio of partial pressure of arterial oxygen to fractional concentration of oxygen inspired air of >300 mm Hg; and (b) administering one or more doses of a niclosamide compound, or a pharmaceutically acceptable salt thereof, to the nasal cavity of the subject; (c) after (a) and (b), identifying whether the subject has at least one of: (i) respiratory distress (i.e., ≥30 breaths per min); (ii) an oxygen saturation at rest of ≤93%; (iii) a ratio of partial pressure of arterial oxygen to fractional concentration of oxygen inspired air of ≤300 mm Hg; and (iv) a severe disease complication, e.g., a severe disease complication as described herein; and (d) administering one or more doses of a niclosamide compound, or a pharmaceutically acceptable salt thereof, to the lungs of the subject in which the subject has at least one of: (i) respiratory distress (i.e., ≥30 breaths per min); (ii) an oxygen saturation at rest of ≤93%; (iii) a ratio of partial pressure of arterial oxygen to fractional concentration of oxygen inspired air of ≤300 mm Hg; and (iv) a severe disease complication, e.g., a severe disease complication as described herein; or (e) administering additional doses of the niclosamide compound, or a pharmaceutically acceptable salt thereof, to the nasal cavity of the subject in which (i) a respiratory rate of <30 breaths per min; (ii) an oxygen saturation at rest of >93%; and (iii) a ratio of partial pressure of arterial oxygen to fractional concentration of oxygen inspired air of >300 mm Hg. In some embodiments, the subject identified in step (a) does not have a severe disease complication. In some embodiments, wherein the niclosamide compound, or a pharmaceutically acceptable salt thereof is administered to the nasal cavity of the subject, the niclosamide compound, or the pharmaceutically acceptable salt thereof, is formulated as an intranasal spray, ointment, or gel (e.g., any of the intranasal compositions described herein). In some embodiments, wherein the niclosamide compound, or a pharmaceutically acceptable salt thereof is administered to the lungs of the subject, the niclosamide compound, or the pharmaceutically acceptable salt thereof, is formulated for delivery by inhalation (e.g., any of the compositions for inhalation described herein).

Also provided herein are methods of treating a subject having COVID-19 that include: (a) identifying a subject having (i) a respiratory rate of <30 breaths per min; (ii) an oxygen saturation at rest of >93%; and (iii) a ratio of partial pressure of arterial oxygen to fractional concentration of oxygen inspired air of >300 mm Hg; and (b) administering one or more doses of a niclosamide compound, or a pharmaceutically acceptable salt thereof, to the nasal cavity of the subject; (c) after (a) and (b), identifying whether the subject has at least one of: (i) respiratory distress (i.e., ≥30 breaths per min); (ii) an oxygen saturation at rest of ≤93%; (iii) a ratio of partial pressure of arterial oxygen to fractional concentration of oxygen inspired air of ≤300 mm Hg; and (iv) a severe disease complication, e.g., a severe disease complication as described herein; and (d) administering one or more doses of a niclosamide compound, or a pharmaceutically acceptable salt thereof, to the GI tract of the subject in which the subject has at least one of: (i) respiratory distress (i.e., ≥30 breaths per min); (ii) an oxygen saturation at rest of ≤93%; (iii) a ratio of partial pressure of arterial oxygen to fractional concentration of oxygen inspired air of ≤300 mm Hg; and (iv) a severe disease complication, e.g., a severe disease complication as described herein; or (e) administering additional doses of the niclosamide compound, or a pharmaceutically acceptable salt thereof, to the nasal cavity of the subject in which (i) a respiratory rate of <30 breaths per min; (ii) an oxygen saturation at rest of >93%; and (iii) a ratio of partial pressure of arterial oxygen to fractional concentration of oxygen inspired air of >300 mm Hg. In some embodiments, the subject identified in step (a) does not have a severe disease complication. In some embodiments, wherein the niclosamide compound, or a pharmaceutically acceptable salt thereof is administered to the nasal cavity of the subject, the niclosamide compound, or the pharmaceutically acceptable salt thereof, is formulated as an intranasal spray, ointment, or gel (e.g., any of the intranasal compositions described herein). In some embodiments, wherein the niclosamide compound, or a pharmaceutically acceptable salt thereof is administered to the GI tract of the subject, the niclosamide compound, or the pharmaceutically acceptable salt thereof, is formulated as an oral composition (e.g., any of the oral compositions described herein).

Also provided herein are methods of treating a subject having COVID-19 that include: (a) identifying a subject having (i) a respiratory rate of <30 breaths per min; (ii) an oxygen saturation at rest of >93%; and (iii) a ratio of partial pressure of arterial oxygen to fractional concentration of oxygen inspired air of >300 mm Hg; and (b) administering one or more doses of a niclosamide compound, or a pharmaceutically acceptable salt thereof, to the nasal cavity of the subject; (c) after (a) and (b), identifying whether the subject has at least one of: (i) respiratory distress (i.e., ≥30 breaths per min); (ii) an oxygen saturation at rest of ≤93%; (iii) a ratio of partial pressure of arterial oxygen to fractional concentration of oxygen inspired air of ≤300 mm Hg; and (iv) a severe disease complication; and (d) administering one or more doses of a niclosamide compound, or a pharmaceutically acceptable salt thereof, to the GI tract of the subject and administering one or more doses of a niclosamide compound, or a pharmaceutically acceptable salt thereof, to the lungs of the subject in which the subject has at least one of: (i) respiratory distress (i.e., ≥30 breaths per min); (ii) an oxygen saturation at rest of ≤93%; (iii) a ratio of partial pressure of arterial oxygen to fractional concentration of oxygen inspired air of ≤300 mm Hg; and (iv) a severe disease complication, e.g., a severe disease complication as described herein; or (e) administering additional doses of the niclosamide compound, or a pharmaceutically acceptable salt thereof, to the nasal cavity of the subject in which (i) a respiratory rate of <30 breaths per min; (ii) an oxygen saturation at rest of >93%; and (iii) a ratio of partial pressure of arterial oxygen to fractional concentration of oxygen inspired air of >300 mm Hg. In some embodiments, the subject identified in step (a) does not have a severe disease complication. In some embodiments, wherein the niclosamide compound, or a pharmaceutically acceptable salt thereof is administered to the nasal cavity of the subject, the niclosamide compound, or the pharmaceutically acceptable salt thereof, is formulated as an intranasal spray, ointment, or gel (e.g., any of the intranasal compositions described herein). In some embodiments, wherein the niclosamide compound, or a pharmaceutically acceptable salt thereof is administered to the GI tract of the subject, the niclosamide compound, or the pharmaceutically acceptable salt thereof, is formulated as an oral composition (e.g., any of the oral compositions described herein). In some embodiments, wherein the niclosamide compound, or a pharmaceutically acceptable salt thereof is administered to the lungs of the subject, the niclosamide compound, or the pharmaceutically acceptable salt thereof, is formulated for delivery by inhalation (e.g., any of the compositions for inhalation described herein).

Also provided herein are methods of treating a subject having COVID-19 that include: (a) identifying a subject having at least one of (i) respiratory distress (i.e., ≥30 breaths per min); (ii) an oxygen saturation at rest of ≤93%; (iii) a ratio of partial pressure of arterial oxygen to fractional concentration of oxygen inspired air of ≤300 mm Hg; and (iv) a severe disease complication; and (b) administering one or more doses of a niclosamide compound, or a pharmaceutically acceptable salt thereof, to the lungs of the subject; (c) after (a) and (b), identifying whether the subject has (i) a respiratory rate of <30 breaths per min; (ii) an oxygen saturation at rest of >93%; and (iii) a ratio of partial pressure of arterial oxygen to fractional concentration of oxygen inspired air of >300 mm Hg; and (d) administering one or more doses of a niclosamide compound, or a pharmaceutically acceptable salt thereof, to the nasal cavity of the subject in which the subject has (i) a respiratory rate of <30 breaths per min; (ii) an oxygen saturation at rest of >93%; and (iii) a ratio of partial pressure of arterial oxygen to fractional concentration of oxygen inspired air of >300 mm Hg; or (e) administering additional doses of the niclosamide compound, or a pharmaceutically acceptable salt thereof, to the lungs of the subject in which the subject has at least one of (i) respiratory distress (i.e., ≥30 breaths per min); (ii) an oxygen saturation at rest of ≤93%; (iii) a ratio of partial pressure of arterial oxygen to fractional concentration of oxygen inspired air of ≤300 mm Hg; and (iv) a severe disease complication, e.g., a severe disease complication as described herein. In some embodiments, the subject identified in step (c) does not have a severe disease complication. In some embodiments, wherein the niclosamide compound, or a pharmaceutically acceptable salt thereof is administered to the GI tract of the subject, the niclosamide compound, or the pharmaceutically acceptable salt thereof, is formulated as an oral composition (e.g., any of the oral compositions described herein). In some embodiments, wherein the niclosamide compound, or a pharmaceutically acceptable salt thereof is administered to the lungs of the subject, the niclosamide compound, or the pharmaceutically acceptable salt thereof, is formulated for delivery by inhalation (e.g., any of the compositions for inhalation described herein). Also provided herein are methods of treating a subject having COVID-19 that include: (a) identifying a subject having a low viral load (e.g., a ΔCt of about 3 to about 15); and (b) administering one or more doses of a niclosamide compound, or a pharmaceutically acceptable salt thereof, to the nasal cavity of the subject; (c) after (a) and (b), identifying whether the subject has a high viral load (e.g., a ΔCt of about 2 to about −10); and (d) administering one or more doses of a niclosamide compound, or a pharmaceutically acceptable salt thereof, to the lungs of the subject in which the subject has a high viral load (e.g., a ΔCt of about 2 to about −10); or (e) administering additional doses of the niclosamide compound, or a pharmaceutically acceptable salt thereof, to the nasal cavity of the subject in which the subject has a low viral load (e.g., a ΔCt of about 3 to about 15). In some embodiments, the subject identified in step (a) does not have a severe disease complication. In some embodiments, wherein the niclosamide compound, or a pharmaceutically acceptable salt thereof is administered to the nasal cavity of the subject, the niclosamide compound, or the pharmaceutically acceptable salt thereof, is formulated as an intranasal spray, ointment, or gel (e.g., any of the intranasal compositions described herein). In some embodiments, wherein the niclosamide compound, or a pharmaceutically acceptable salt thereof is administered to the lungs of the subject, the niclosamide compound, or the pharmaceutically acceptable salt thereof, is formulated for delivery by inhalation (e.g., any of the compositions for inhalation described herein).

Also provided herein are methods of treating a subject having COVID-19 that include: (a) identifying a subject having a low viral load (e.g., a ΔCt of about 3 to about 15); and (b) administering one or more doses of a niclosamide compound, or a pharmaceutically acceptable salt thereof, to the nasal cavity of the subject; (c) after (a) and (b), identifying whether the subject has a high viral load (e.g., a ΔCt of about 2 to about −10).; and (d) administering one or more doses of a niclosamide compound, or a pharmaceutically acceptable salt thereof, to the GI tract of the subject in which the subject has a high viral load (e.g., a ΔCt of about 2 to about −10).; or (e) administering additional doses of the niclosamide compound, or a pharmaceutically acceptable salt thereof, to the nasal cavity of the subject in which the subject has a low viral load (e.g., a ΔCt of about 3 to about 15). In some embodiments, the subject identified in step (a) does not have a severe disease complication. In some embodiments, wherein the niclosamide compound, or a pharmaceutically acceptable salt thereof is administered to the nasal cavity of the subject, the niclosamide compound, or the pharmaceutically acceptable salt thereof, is formulated as an intranasal spray, ointment, or gel (e.g., any of the intranasal compositions described herein). In some embodiments, wherein the niclosamide compound, or a pharmaceutically acceptable salt thereof is administered to the GI tract of the subject, the niclosamide compound, or the pharmaceutically acceptable salt thereof, is formulated as an oral composition (e.g., any of the oral compositions described herein).

Also provided herein are methods of treating a subject having COVID-19 that include: (a) identifying a subject having a low viral load (e.g., a ΔCt of about 3 to about 15).; and (b) administering one or more doses of a niclosamide compound, or a pharmaceutically acceptable salt thereof, to the nasal cavity of the subject; (c) after (a) and (b), identifying whether the subject has a high viral load (e.g., a ΔCt of about 2 to about −10); and (d) administering one or more doses of a niclosamide compound, or a pharmaceutically acceptable salt thereof, to the GI tract of the subject and administering one or more doses of a niclosamide compound, or a pharmaceutically acceptable salt thereof, to the lungs of the subject in which the subject has a high viral load (e.g., a ΔCt of about 2 to about −10); or (e) administering additional doses of the niclosamide compound, or a pharmaceutically acceptable salt thereof, to the nasal cavity of the subject in which the subject has a low viral load (e.g., a ΔCt of about 3 to about 15). In some embodiments, the subject identified in step (a) does not have a severe disease complication. In some embodiments, wherein the niclosamide compound, or a pharmaceutically acceptable salt thereof is administered to the nasal cavity of the subject, the niclosamide compound, or the pharmaceutically acceptable salt thereof, is formulated as an intranasal spray, ointment, or gel (e.g., any of the intranasal compositions described herein). In some embodiments, wherein the niclosamide compound, or a pharmaceutically acceptable salt thereof is administered to the GI tract of the subject, the niclosamide compound, or the pharmaceutically acceptable salt thereof, is formulated as an oral composition (e.g., any of the oral compositions described herein). In some embodiments, wherein the niclosamide compound, or a pharmaceutically acceptable salt thereof is administered to the lungs of the subject, the niclosamide compound, or the pharmaceutically acceptable salt thereof, is formulated for delivery by inhalation (e.g., any of the compositions for inhalation described herein).

Also provided herein are methods of treating a subject having COVID-19 that include: (a) identifying a subject having 19 has a high viral load (e.g., a ΔCt of about 2 to about −10); and (b) administering one or more doses of a niclosamide compound, or a pharmaceutically acceptable salt thereof, to the lungs of the subject; (c) after (a) and (b), identifying whether the subject has a low viral load (e.g., a ΔCt of about 3 to about 15).; and (d) administering one or more doses of a niclosamide compound, or a pharmaceutically acceptable salt thereof, to the nasal cavity of the subject in which the subject has a low viral load (e.g., a ΔCt of about 3 to about 15).; or (e) administering additional doses of the niclosamide compound, or a pharmaceutically acceptable salt thereof, to the lungs of the subject in which the subject has a high viral load (e.g., a ΔCt of about 2 to about −10). In some embodiments, the subject identified in step (c) does not have a severe disease complication. In some embodiments, wherein the niclosamide compound, or a pharmaceutically acceptable salt thereof is administered to the GI tract of the subject, the niclosamide compound, or the pharmaceutically acceptable salt thereof, is formulated as an oral composition (e.g., any of the oral compositions described herein). In some embodiments, wherein the niclosamide compound, or a pharmaceutically acceptable salt thereof is administered to the lungs of the subject, the niclosamide compound, or the pharmaceutically acceptable salt thereof, is formulated for delivery by inhalation (e.g., any of the compositions for inhalation described herein).

Combination Therapy

In some embodiments, the methods and compositions described herein are suitable for use in combination therapy with various other therapeutic regimens. In certain embodiments, the niclosamide compounds, or pharmaceutically acceptable salts thereof, and methods described herein can be used to treat side effects produced by such therapeutic regimens.

In some embodiments, the methods and compositions described herein are suitable for use in combination therapy with one or more additional therapeutic agents.

In certain embodiments, the one or more additional therapeutic agents is administered to the subject prior to contacting with or administering the niclosamide compound, or a pharmaceutically acceptable salt thereof, (e.g., about one hour prior, or about 6 hours prior, or about 12 hours prior, or about 24 hours prior, or about 48 hours prior, or about 1 week prior, or about 1 month prior).

In other embodiments, the one or more additional therapeutic agents is administered to the subject at about the same time as contacting with or administering the niclosamide compound, or a pharmaceutically acceptable salt thereof. By way of example, the second therapeutic agent or regimen and the niclosamide compound, or a pharmaceutically acceptable salt thereof, are provided to the subject simultaneously in the same dosage form. As another example, the second therapeutic agent or regimen and the niclosamide compound, or a pharmaceutically acceptable salt thereof, are provided to the subject concurrently in separate dosage forms.

In still other embodiments, the one or more additional therapeutic agents is administered to the subject after contacting with or administering the niclosamide compound, or a pharmaceutically acceptable salt thereof, (e.g., about one hour after, or about 6 hours after, or about 12 hours after, or about 24 hours after, or about 48 hours after, or about 1 week after, or about 1 month after).

In some embodiments, one or more therapies can be used in combination with the materials and/or methods described herein. In some embodiments, a combination therapy can include one or more of a macrolide antibiotic, an anti-malarial agent, an anti-diabetic agent, an angiotensin receptor inhibitor, an angiotensin-converting enzyme (ACE) inhibitor, a statin, a polymerase inhibitor (e.g., a RNA-dependent RNA polymerase inhibitor), a protease inhibitor, a neuraminidase inhibitor, a fusion inhibitor, a transmembrane protease serine 2 (TMPRSS2) inhibitor, a broad-spectrum antiviral agent, a JAK-STAT pathway inhibitor, a DNA synthesis inhibitor, a phosphodiesterase 5 (PDE5) inhibitor, a monoclonal antibody, passive antibody therapy, recombinant human angiotensin-converting enzyme 2 (rhACE2), traditional Chinese medicine, a pharmaceutically acceptable salt or solvate of any thereof, or two or more of any thereof. In some embodiments, the macrolide antibiotic and/or anti-malarial agent is a lysosomotropic agent. Non-limiting examples of lysosomotropic agents include azithromycin, hydroxychloroquine, chloroquine, and ammonium chloride. Non-limiting examples of an anti-diabetic agent include a biguanide, a sulfonylurea, a glitazar, a thiazolidinedione, a dipeptidyl peptidase 4 (DPP-4) inhibitor, a meglitinide, a sodium-glucose linked transporter 2 (SGLT2) inhibitor, a glitazone, a GRP40 agonist, a glucose-dependent insulinotropic peptide (GIP), an insulin or insulin analogue, an alpha glucosidase inhibitor, a sodium-glucose linked transporter 1 (SGLT1) inhibitor. In some embodiments, the biguanide is metformin. A non-limiting example of an angiotensin receptor inhibitor includes a sartan (e.g., eprosartan, olmesartan, olmesartan medoxomil, valsartan, candesartan, candesartan cilexetil, losartan, telmisartan, irbesartan, BRA-657, and azilsartan medoxomil). Non-limiting examples of an ACE inhibitor include: quinapril, fosinopril perindopril, captopril, enalapril, enalaprilat, ramipril, cilazapril, delapril, fosenopril, zofenopril, indolapril, benazepril, lisinopril, spirapril, trandolapril, perindep, pentopril, moexipril, rescinnamine, and pivopril. Non-limiting examples of a statin include atorvastatin, fluvastatin, lovastatin, pitavastatin, pravastatin, rosuvastatin, and simvastatin, cerivastatin, and mevastatin. Non-limiting examples of polymerase inhibitors include ganciclovir, valganciclovir, and RNA-dependent RNA polymerase (RdRP) inhibitors (e.g., remdesivir, ribavirin, and favipiravir). Non-limiting examples of protease inhibitors include lopinavir, ritonavir, indinavir, atazanavir, nelfinavir, darunavir, tipranavir, amprenavir, and fosamprenavir. A non-limiting example of a neuraminidase inhibitor is oseltamivir. A non-limiting example of a fusion inhibitor is umifenovir. A non-limiting example of a TMPRSS2 inhibitor is camostat. Non-limiting examples of broad-spectrum antiviral agents include nitazoxanide, chloroquine, hydroxychloroquine, and interferon (e.g., interferon alfa). Non-limiting examples of JAK-STAT pathway inhibitors include baricitinib, fedratinib, and ruxolitinib. Non-limiting examples of DNA synthesis inhibitors include tenofovir disoproxil and lamivudine. A non-limiting example of a PDE5 inhibitor is sildenafil. A non-limiting example of traditional Chinese medicine is huaier extract. See, e.g., Liu, Cynthia, et al. "Research and Development on Therapeutic Agents and Vaccines for COVID-19 and Related Human Coronavirus Diseases." (2020). doi/10.1021/acscentsci.0c00272; Lai, Chih-Cheng, et al. "Severe acute respiratory syndrome coronavirus 2 (SARS-CoV-2) and coronavirus disease-2019 (COVID-19): the epidemic and the challenges." International journal of antimicrobial agents (2020): 105924; Chang, Yu-Chuan, et al. "Potential therapeutic agents for COVID-19 based on the analysis of protease and RNA polymerase docking." (2020). doi: 10.20944/preprints202002.0242.v1; NCT04252885; NCT04306497; NCT04287686; NCT04307693; NCT04292899; NCT04304313; NCT04291053; Ko W C, Rolain J M, Lee N Y, et al. Arguments in favor of remdesivir for treating SARS-CoV-2 infections [published online ahead of print, 2020 Mar. 5]. Int J Antimicrob Agents. 2020; 105933. doi:10.1016/j.ijantimicag.2020.105933; Dhama, K., et al. (2020). Coronavirus Disease 2019-COVID-19. doi: 10.20944/preprints202003.0001.v1; Stebbing, Justin, et al. "COVID-19: combining antiviral and anti-inflammatory treatments." The Lancet Infectious Diseases (2020); Yang, Naidi, and Han-Ming Shen. "Targeting the Endocytic Pathway and Autophagy Process as a Novel Therapeutic Strategy in COVID-19." Int J Biol Sci 16.10 (2020): 1724-1731.; Casadevall, Arturo, and Liise-anne Pirofski. "The convalescent sera option for containing COVID-19." The Journal of Clinical Investigation 130.4 (2020); Shanmugaraj, Balamurugan, et al. "Perspectives on monoclonal antibody therapy as potential therapeutic intervention for Coronavirus disease-19 (COVID-19)." Asian Pacific journal of allergy and immunology (2020); and Xu, Jimin, et al. "Broad Spectrum Antiviral Agent Niclosamide and Its Therapeutic Potential." ACS Infectious Diseases (2020), each of which is incorporated by reference herein in its entirety.

Provided herein are methods for treating COVID-19 in a subject in need thereof, the method comprising administering a niclosamide compound, or a pharmaceutically acceptable salt thereof, and a lysosomotropic agent to the subject. In some embodiments, the lysosomotropic agent is selected from azithromycin, hydroxychloroquine, chloroquine, ammonium chloride, and a combination thereof.

In some embodiments, methods provided herein for treating COVID-19 in a subject in need thereof include administering a niclosamide compound, or a pharmaceutically acceptable salt thereof, and azithromycin. In some embodiments, about 500 mg azithromycin is administered to the subject once per day. In some embodiments, about 250 mg azithromycin is administered to the subject once per day. In some embodiments, about 500 mg azithromycin is administered to the subject on Day 1 and about 250 mg azithromycin is administered to the subject once per day on Days 2-5. See, e.g., Gautret et al. Int J Antimicrob Agents. 2020 Mar. 20:105949.

In some embodiments, methods provided herein for treating COVID-19 in a subject in need thereof include administering a niclosamide compound, or a pharmaceutically acceptable salt thereof, and hydroxychloroquine. In some embodiments, about 200 mg hydroxychloroquine is administered to the subject three times per day. In some embodiments, about 200 mg hydroxychloroquine is administered to the subject three times per day for about 10 days. See, e.g., Gautret et al. *Int J Antimicrob* Agents. 2020 Mar. 20:105949.

In some embodiments, methods provided herein for treating COVID-19 in a subject in need thereof include administering a niclosamide compound, or a pharmaceutically acceptable salt thereof, and chloroquine.

In some embodiments, methods provided herein for treating COVID-19 in a subject in need thereof include administering a niclosamide compound, or a pharmaceutically acceptable salt thereof, azithromycin, and hydroxychloroquine.

In some embodiments, methods provided herein for treating COVID-19 in a subject in need thereof include administering a niclosamide compound, or a pharmaceutically acceptable salt thereof, azithromycin, and chloroquine.

In some embodiments, the chloroquine is chloroquine phosphate (e.g., ARALEN®). In some embodiments, the hydroxychloroquine is hydroxychloroquine sulfate (e.g., PLAQUENIL®).

Also provided herein are methods for treating COVID-19 in a subject in need thereof, the methods comprising administering a niclosamide compound, or a pharmaceutically acceptable salt thereof, and an anti-diabetic agent. In some embodiments, the anti-diabetic agent is metformin.

Also provided herein are methods for treating COVID-19 in a subject in need thereof, the methods comprising administering a niclosamide compound, or a pharmaceutically acceptable salt thereof, and an angiotensin receptor inhibitor. In some embodiments, the angiotensin receptor inhibitor is selected from eprosartan, olmesartan, valsartan, candesartan, losartan, telmisartan, irbesartan, azilsartan medoxomil, and a combination thereof.

Also provided herein are methods for treating COVID-19 in a subject in need thereof, the methods comprising administering a niclosamide compound, or a pharmaceutically acceptable salt thereof, and a statin. In some embodiments, the statin is selected from atorvastatin, fluvastatin, lovastatin, pitavastatin, pravastatin, rosuvastatin, and simvastatin, cerivastatin, mevastatin, and a combination thereof.

Niclosamide Compounds

Chemical Purity

In some embodiments, the niclosamide compounds (e.g., niclosamide) has a chemical purity of greater than about 99.0%; e.g., greater than about 99.5%; or greater than about 99.7%; or greater than about 99.8%.

In some embodiments, the niclosamide compounds (e.g., niclosamide) have less than about 45 ppm of 5-chlorosalicylic acid; e.g., less than about 30 ppm of 5-chlorosalicylic acid.

In some embodiments, the compound has less than about 50 ppm of 2-chloro-4 nitro-aniline. In certain embodiments, the compound has less than about 10 ppm of 2-chloro-4 nitro-aniline.

In some embodiments, the compound has less than about 45 ppm of 5-chloro-salicylic acid and less than about 50 ppm of 2-chloro-4 nitro-aniline.

In some embodiments, the compound has less than about 30 ppm of 5-chloro-salicylic acid and less than about 10 ppm of 2-chloro-4 nitro-aniline.

In some embodiments, the compound has less than about 0.05% water. In certain embodiments, the compound is substantially free of hydrated niclosamide solid forms. As a non-limiting example, the compound can be anhydrous niclosamide.

In some embodiments, purification can be carried out according to the following process. Acetone and crude niclosamide are mixed in a vessel and heated to reflux (−56° C.) until solids dissolve. The solution is clarified by filtration and transferred to a second vessel, heated to 45° C. to 55° C. to dissolve the solids, cooled to −5° C. to 5° C. and stirred at this temperature for at least 2 hours. The solids are filtered and washed with acetone. Crystallized niclosamide is obtained after vacuum drying of the solids at 70° C. IPC LOD testing is performed on the dry solids with a specification of <1.0%. If the LOD results are >1.0% the drying step may be repeated two additional times. IPC testing is also performed to ensure the level of the starting material 2-chloro-4-nitroaniline is <100 ppm. If the level of 2-chloro-4-nitroaniline is >100 ppm, a second crystallization may be performed.

In some embodiments, purity analysis can be achieved according to the following procedure. Chromatograph: UPLC system consisting pump, diode array; detector, autosampler, auto injector, and column cooler/heater, or equivalent. Column: Agilent Poroshell 120 EC-C18 column, 4.6×50 mm, 2.7 m or equivalent. Column Temperature: 35° C. Mobile phase A: 20 mM ammonium acetate (pH 5.50). Mobile phase B: MeOH:ACN (70:30, v/v). Diluent: MeOH: DMSO (70:30, v/v).

| Time (min.) | Solvent A (%) | Solvent B (%) |
|---|---|---|
| 0.0 | 75 | 25 |
| 1.0 | 75 | 25 |
| 21.0 | 30 | 70 |

Flow rate: 1.0 ml/min. Injected volume: 3.00 μl. Preparation of standard and sample solutions. Niclosamide Standard Solutions: Concentration of this solution is nominally 0.8 mg/mL. Retention times: 5-Chlorosalicylic acid (2.9 minutes); 2-Chloro-4-nitroaniline (7.0 minutes); and Niclosamide (18.8 minutes).

Particle Size

In some embodiments, the compound has a reduced particle size (e.g., as achieved by techniques including but not limited to milling).

In some embodiments, niclosamide compounds having reduced particle size can be prepared by jet milling, e.g., using CMTI equipment NGMP-Mill-A, a 2-inch, pancake micronizer manufactured by Sturtevant; a flexible containment unit was used during the milling process (Mill and Venturi pressure both=50 psi; feed rate 96.0 g/hour).

In some embodiments of the foregoing, the compound has a particle size range of from about 0.1 μm to about 30 μm. In certain embodiments, the compound has a particle size range of from about 0.1 μm to about 20 μm. In certain embodiments, the compound has a particle size range of from about 0.1 μm to about 10 μm.

The term "particle size distribution" of a powder, or granular material, or particles dispersed in fluid, as used within this application, is a list of values or a mathematical function that defines the relative amounts of particles present, sorted according to size. The d(0.1), d(0.5) and d(0.9) values indicate that 10%, 50% and 90% of the particles measured were less than or equal to the size stated. For example, values of d(0.1)=0.6, d(0.5)=3.1 and d(0.9)=7.3 mean that 10% of the particles were less than or equal to 0.6 μm, 50% were less than or equal to 3.1 μm, and 90% were less than or equal to 7.3 μm.

Particle Size Distribution (PSD) can be determined by laser diffraction technique, e.g., using a "MALVERN MASTERSIZER 2000" (standard range between 0.020 and 2000.0 microns), model "APA 2000", equipped with "Hydro 2000 sm" as dispersing unit. A representative procedure includes: approximately 50 mg of Niclosamide is dispersed manually into 25 ml of water; after dispersion the sample was sonicated with external ultrasound for two minutes (Ultrasonic frequency; 37 kHz—Elmasonic S100 (H)—Elma Schmidbauer GmbH, Germany); the following operative conditions/machine parameters are taken into account: Dispersant: Water+3 drops of Tyloxapol 1.5%; Background measurement time: 10 seconds; Number of measurements cycles: 3 (to obtain average value); Stir speed (dispersing unit): 1500 rpm.

In some embodiments, the compound has a particle size distribution D(0.9) of from about 1.0 μm to about 15.0 μm. In certain embodiments, the compound has a particle size distribution D(0.9) of from about 1.0 μm to about 10.0 μm. In certain embodiments, the compound has a particle size distribution D(0.9) of from about 6.0 μm to about 8.0 μm (e.g., about 7.3 μm (e.g., 7.3 μm)). In other embodiments, the compound has a particle size distribution D(0.9) of from about 2.2 μm to about 3.2 μm.

In some embodiments, the compound has a particle size distribution D(0.1) of from about 0.1 μm to about 1.5 μm. In certain embodiments, the compound has a particle size distribution D(0.1) of from about 0.1 μm to about 1.0 μm. In certain embodiments, the compound has a particle size distribution D(0.1) of from about 0.3 μm to about 0.9 μm. In certain embodiments, the compound has a particle size distribution D(0.1) of from about 0.45 μm to about 0.75 μm (e.g., about 0.6 μm (e.g., 0.6 μm)).

In some embodiments, the compound has a particle size distribution D(0.5) of from about 0.5 μm to about 6.0 μm. In certain embodiments, the compound has a particle size distribution D(0.5) of from about 1.0 μm to about 4.0 μm. In certain embodiments, the compound has a particle size distribution D(0.5) of from about 1.0 μm to about 2.0 μm. In certain other embodiments, the compound has a particle size distribution D(0.5) of from about 2.5 μm to about 3.5 μm (e.g., about 3.1 μm (e.g., 3.1 μm)).

The parameter D(0.1) as used herein refers to the mesh size of a single notional sieve allowing 10% of the total of all particles of the sample to pass. Thus D(0.1)=0.1-1.5 μm means that the upper limit of the particle size range defining the 10% of smallest particles in the sample is between 0.1 μm to 1.5 μm. Thus 10% of the total particles have a particle size of not more than D(0.1) meaning in this case that they have a maximum size of 0.1 μm to 1.5 μm.

The parameter D(0.5) refers to the mesh size of a single notional sieve allowing 50% of the total of all particles of the sample to pass. Thus D(0.5)=0.5-6.0 μm means that the upper limit of the particle size range defining the notional half of the sample containing the smaller particles is between 0.5 μm to 6.0 μm. Thus, 50% of the total of all particles have a particle size of not more than D(0.5) meaning in this case that they have a maximum size of 0.5 μm to 6.0 μm.

The parameter D(0.9) refers to the mesh size of a single notional sieve allowing 90% of the total of all particles of the sample to pass i.e. only 10% of the sample is retained. Thus, D(0.9)=1.0-15.0 μm means that the lower limit of the particle size range defining the 10% of largest particles in the sample is between 1.0 μm to 15.0 μm. Thus 90% of all particles have a particle size of not more than D(0.9) meaning in this case that they have a maximum size of 1.0 μm to 15.0 μm.

In some embodiments, the compound has less than about 0.05% water (e.g., as determined by Karl Fisher technique). In certain embodiments, the compound is substantially free of hydrated niclosamide solid forms. As a non-limiting example, the compound can be anhydrous niclosamide.

In some embodiments, the compound is crystalline.

In some embodiments, the compound has a specific surface area of from about 5 $m^2/g$ to about 10 $m^2/g$.

Non-Limiting Combination

Non-Limiting Combinations [A]

In some embodiments, the compound has a particle size distribution D(0.9) of from about 1.0 μm to about 10.0 μm, a particle size distribution D(0.5) of from about 1.0 μm to about 4.0 μm, and a particle size distribution D(0.1) of from about 0.1 μm to about 1.0 μm.

In some embodiments, the compound has a particle size distribution D(0.9) of from about 6.0 μm to about 8.0 μm, a particle size distribution D(0.5) of from about 1.0 μm to about 4.0 μm, and a particle size distribution D(0.1) of from about 0.3 μm to about 0.9 μm.

In some embodiments, the compound has a particle size distribution D(0.9) of from about 7.0 μm to about 7.5 μm (e.g., about 7.3 μm), a particle size distribution D(0.5) of from about 2.5 μm to about 4.0 μm (e.g., about 3.1 μm), and a particle size distribution D(0.1) of from about 0.45 μm to about 0.75 μm (e.g., about 0.6 μm).

In some embodiments, the compound has a particle size distribution D(0.9) of about 7.3 μm, a particle size distribution D(0.5) of about 3.1 μm, and a particle size distribution D(0.1) of about 0.6 μm.

In some embodiments, the compound has a particle size distribution D(0.9) of from about 2.2 μm to about 3.2 μm, a particle size distribution D(0.5) of from about 1.0 μm to about 4.0 μm, and a particle size distribution D(0.1) of from about 0.3 μm to about 0.9 μm.

In some embodiments, the compound has a chemical purity of greater than about 99.0%, a particle size distribution D(0.9) of from about 1.0 μm to about 10.0 μm, a particle size distribution D(0.5) of from about 1.0 μm to about 4.0 μm, and a particle size distribution D(0.1) of from about 0.1 μm to about 1.0 μm.

In some embodiments, the compound has a chemical purity of greater than about 99.0%, a particle size distribution D(0.9) of from about 6.0 μm to about 8.0 μm, a particle size distribution D(0.5) of from about 1.0 μm to about 4.0 μm, and a particle size distribution D(0.1) of from about 0.3 μm to about 0.9 μm.

In some embodiments, the compound has a chemical purity of greater than about 99.0%, a particle size distribution D(0.9) of from about 2.2 μm to about 3.2 μm, a particle size distribution D(0.5) of from about 1.0 μm to about 4.0 μm, and a particle size distribution D(0.1) of from about 0.3 μm to about 0.9 μm.

In some embodiments, the compound has a chemical purity of greater than about 99.0%, a particle size range of from about 0.1 μm to about 30 μm, a particle size distribution D(0.9) of from about 1.0 μm to about 10.0 μm, a particle size distribution D(0.5) of from about 1.0 μm to about 4.0 μm, and a particle size distribution D(0.1) of from about 0.1 μm to about 1.0 μm.

In some embodiments, the compound has a chemical purity of greater than about 99.0%, a particle size range of from about 0.1 μm to about 30 μm, a particle size distribution D(0.9) of from about 6.0 μm to about 8.0 μm, a particle size distribution D(0.5) of from about 1.0 μm to about 4.0 μm, and a particle size distribution D(0.1) of from about 0.3 μm to about 0.9 μm.

In some embodiments, the compound has a chemical purity of greater than about 99.0%, a particle size range of from about 0.1 μm to about 30 μm, a particle size distribution D(0.9) of from about 2.2 μm to about 3.2 μm, a particle size distribution D(0.5) of from about 1.0 μm to about 4.0 μm, and a particle size distribution D(0.1) of from about 0.3 μm to about 0.9 μm.

In certain embodiments of [A], the compound has a particle size distribution D(0.5) of from about 2.5 μm to about 3.5 μm.

In certain embodiments of [A], the compound has a particle size distribution D(0.5) of from about 1.0 μm to about 2.0 μm.

In certain embodiments of [A], the compound has a chemical purity of greater than about 99.5%; or a chemical purity of greater than about 99.7%; or a chemical purity of greater than about 99.8%.

In certain embodiments of [A], the compound has less than about 45 ppm of 5-chloro-salicylic acid; or less than about 30 ppm of 5-chloro-salicylic acid.

In certain embodiments of [A], the compound has less than about 50 ppm of 2-chloro-4 nitro-aniline; or less than about 10 ppm of 2-chloro-4 nitro-aniline.

In certain embodiments of [A], the compound has less than about 45 ppm of 5-chloro-salicylic acid and less than about 50 ppm of 2-chloro-4 nitro-aniline; or less than about 30 ppm of 5-chloro-salicylic acid and less than about 10 ppm of 2-chloro-4 nitro-aniline.

In certain embodiments of [A], the compound has less than about 0.05% water.

In certain embodiments of [A], the compound is substantially free of hydrated niclosamide solid forms.

In certain embodiments of [A], the compound is anhydrous niclosamide.

In certain embodiments of [A], the compound is crystalline.

In certain embodiments of [A], the compound has a specific surface area of from about 5 $m^2/g$ to about 10 $m^2/g$.

Cocrystals of Niclosamide Compounds

Overview

In some embodiments, the niclosamide compounds (e.g., niclosamide) can be in the form of a cocrystal that includes (i) a niclosamide compound (e.g., niclosamide) or a pharmaceutically acceptable salt thereof, and (ii) one or more pharmaceutically acceptable coformers. The term "co-crystal" as used herein refers to a crystalline material comprised of two or more unique solids at room temperature in a stoichiometric or non-stoichiometric ratio, which are held together in the crystal lattice by one or more non-covalent interactions (e.g., hydrogen bonds, pi-stacking, guest-host complexation and van der Waals interactions).

In some embodiments, at least one of the one or more non-covalent interactions is a hydrogen bond. In certain of these embodiments, the chemical entity is the hydrogen bond donor, and one of one or more coformers is the hydrogen bond acceptor. In other embodiments, the chemical entity is the hydrogen bond acceptor, and one of one or more coformers is the hydrogen bond donor.

The co-crystals described herein can include one or more solvate (e.g., water or an organic solvent containing one or more hydroxyl groups, e.g., a $C_1$-$C_6$ alcohol or diol, e.g., a $C_1$-$C_6$ alcohol or diol, e.g., ethanol or propylene glycol) molecules in the crystalline lattice. However, solvates of chemical entities that do not further comprise a coformer (e.g., a solid conformer) are not encompassed by the co-crystal definition set forth in this disclosure.

In some embodiments, the cocrystal includes more than one coformer. For example, two, three, four, five, or more co formers can be incorporated in a co-crystal with the chemical entity. The ratio of the chemical entity to each of the one or more pharmaceutically acceptable coformers may be stoichiometric or non-stoichiometric. As a non-limiting example, 1:1, 1:1.5 and 1:2 ratios of chemical entity:coformer are contemplated.

The niclosamide compounds (e.g., niclosamide) and each of the one or more pharmaceutically acceptable coformers may each be independently specified as a free form, or more specifically, a free acid, free base, or zwitter ion; a salt, or more specifically for example, an inorganic base addition salt such as sodium, potassium, lithium, calcium, magnesium, ammonium, aluminum salts or organic base addition salts, or an inorganic acid addition salts such as HBr, HCl, sulfuric, nitric, or phosphoric acid addition salts or an organic acid addition salt such as acetic, proprionic, pyruvic, malanic, succinic, malic, maleic, fumaric, tartaric, citric, benzoic, methanesulfonic, ethanesulforic, stearic or lactic acid addition salt; an anhydrate or hydrate of a free form or salt, or more specifically, for example, a hemihydrate, monohydrate, dihydrate, trihydrate, quadrahydrate, pentahydrate; or a solvate of a free form or salt.

Coformers

In some embodiments, at least one of the one or more pharmaceutically acceptable coformers can form one or more hydrogen bonds with the chemical entity in the cocrystal. In some embodiments, at least one of the one or more pharmaceutically acceptable coformers can accept one or more hydrogen bonds from the chemical entity in the cocrystal. In some embodiments, at least one of the one or more pharmaceutically acceptable coformers can form one or more hydrogen bonds with the chemical entity in the cocrystal, and at least one of the one or more pharmaceutically acceptable coformers can accept one or more hydrogen bonds from the chemical entity in the cocrystal.

In some embodiments, at least one of the one or more pharmaceutically acceptable coformers comprises one or more functional groups selected from the group consisting of: ether, thioether, hydroxy, sulfhydryl, aldehyde, ketone, thioketone, nitrate ester, phosphate ester, thiophosphate ester, ester, thioester, sulfate ester, carboxylic acid, phosphonic acid, phosphinic acid, sulfonic acid, amido, primary amine, secondary amine, ammonia, tertiary amino, sp2 amino, thiocyanate, cyanamide, oxime, nitrile, diazo, haloalkyl, nitro, heterocyclic ring, heteroaryl ring, epoxide, peroxide, and hydroxamic acid.

In certain embodiments, each of the one of the one or more pharmaceutically acceptable coformers is independently selected from acetamide, benzamide, (+/−)-limonene, 1-(phenylazo)-2-naphthylamine, 1,2,6-hexanetriol, 1,2-dimyristoyl-sn-glycero-3-(phospho-s-(1-glycerol)), 1,2-dimyristoyl-sn-glycero-3-phosphocholine, 1,2-dioleoyl-snglycero-3-phosphocholine, 1,2-dipalmitoyl-sn-glycero-3-(phospho-rac-(1-glycerol)), 1,2-distearoyl-sn-glycero-3-(phospho-rac-(1-glycerol)), 1,2-distearoyl-sn-glycero-3-phosphocholine, 1,5-naphthalene-disulfonic acid, 1-hydroxy-2-naphthoic acid, 1-o-tolylbiguanide, 2-ethyl-1,6-hexanediol, 4-aminobenzoic acid, 4-aminopyridine, 4-aminosalicylic acid, 4-chlorobenzene-sulfonic acid, 4-ethoxyphenyl urea, 7-oxo-dhea, acacia, acacia mucilage, acacia syrup, acesulfame, acesulfame potassium, acetohydroxamic acid, acetone sodium bisulfite, acetylated lanolin alcohols, acetylated monoglycerides, acetylcysteine, acetyltributyl citrate, acrylates copolymer, acrylic acid-isooctyl acrylate copolymer, adenine, adipic acid, alanine, albumin aggregated, albumin colloidal, albumin human, albumins, alginic acid, alkyl ammonium sulfonic acid betaine, alkyl aryl sodium sulfonate, allantoin, allopurineol, allyl alpha-ionone, alpha-terpineol, alpha-tocopherol, alpha-tocopherol acetate, aminobenzoate sodium, amyl acetate, anethole, anhydrous citric acid, anhydrous dextrose, anhydrous lactose, anhydrous tribasic sodium phosphate, anhydrous trisodium citrate, arginine, arlacel, asafetida, ascorbic acid, ascorbyl palmitate, asparagine, aspartame, aspartic acid, bacteriostatic sodium chloride injection, barium sulfate, benzalkonium chloride, benzenesulfonic acid, benzethonium chloride, benzododecinium bromide, benzoic acid, benzyl acetate, benzyl alcohol, benzyl benzoate, benzyl chloride, beta-carotene, betanaphthol, betose, bibapcitide, bismuth subcarbonate, bismuth subgallate, boric acid, brocrinat, butyl stearate, butylated hydroxyanisole, butylated hydroxytoluene, butylparaben, butyric acid, C-11-1-amino-cyclohexanecarboxylic acid, C12-15 alkyl lactate, caffeine, calcobutrol, caldiamide sodium, caloxetate trisodium, calteridol calcium, camphoric acid, capric acid, captan, captisol, carboxypolymethylene, carmine, carnauba wax, carnauba yellow wax, carrageenan, carrageenan calcium, carrageenan salt, carrageenan sodium, ceresin, ceteareth-12, ceteareth-15, ceteareth-30, cetearyl alcohol/ceteareth-20, cetearyl ethylhexanoate, ceteth-10, ceteth-2, ceteth-20, ceteth-23, cetostearyl alcohol, cetrimonium chloride, cetyl alcohol, cetyl esters wax, cetyl palmitate, cetylpyridinium chloride, chlorocresol, chloroxylenol, cholesterol, chrysin, cinnamaldehyde, cinnamic acid, citrate, citric acid, citric acid monohydrate, clemizole, cocamide ether sulfate, cocamine oxide, coco betaine, coco diethanolamide, coco monoethanolamide, coco-caprylate, coco-glycerides, creatine, creatinine, cresol, cupric sulfate, cyclamic acid, cyclomethicone, cyclomethicone 5, cysteine, dalfampridine, decyl methyl sulfoxide, dehydroacetic acid, denatonium benzoate, deoxycholic acid, dextran, dextran 40, dextrates, dextrin, dextrose, dextrose monohydrate, diacetylated monoglycerides, diatrizoic acid, dibasic anhydrous sodium phosphate, dibasic sodium phosphate, dibasic sodium phosphate dihydrate, dibasic sodium phosphate dodecahydrate, dibasic sodium phosphate heptahydrate, dibutyl phthalate, dibutyl sebacate, diethyl phthalate, diethyl pyrocarbonate, diethyl sebacate, diethylaminoethyl stearamide phosphate, diethylene glycol monoethyl ether, diethylene glycol monomethyl ether, diethylhexyl phthalate, diisopropyl adipate, diisopropyl dilinoleate, diisopropylbenzothiazyl-2-sulfenamide, dimethicone medical fluid 360, dimethyl isosorbide, dimethyl phthalate, dimethyl sulfoxide, dimethyldioctadecylammonium bentonite, dimethylglycine, dimethylsiloxane/methylvinylsiloxane copolymer, dinoseb-ammonium, dipropylene glycol, disodium cocoamphodiacetate, disodium hydrogen citrate, disodium laureth sulfosuccinate, disodium lauryl sulfosuccinate, disodium oleamido monoethanolamine sulfosuccinate, disodium sulfosalicylate, disofenin, dl-a350 lactic acid, dl-acetyltryptophan, dl-alpha-tocopherol, dl-alpha-tocopherol acetate, dl-dipalmitoylphosphatidylglycerol, dl-distearoylphosphatidylcholine, dl-glutamic acid, dl-tartaric acid, d-mannose, dmdm hydantoin, docosanol, docusate sodium, d-ribose, edetate calcium disodium, edetate disodium, edetate sodium, edetic acid, egg phosphatidyl glycerol, egg phospholipids, entsufon, entsufon sodium, epilactose, epitetracycline hydrochloride, erythorbic acid, erythritol, ethanolamine hydrochloride, ethyl maltol, ethyl oleate, ethyl vanillate, ethyl vanillin, ethylenediamine dihydrochloride, ethylhexyl hydroxystearate, ethylparaben, eucalyptol, eugenol, exametazime, fatty acid esters, fatty acid glycerides, fatty acid pentaerythriol ester, fatty acids, fatty alcohol citrate, fatty alcohols, ferric chloride, ferric oxide, ferrosoferric oxide, ferrous fumarate, ferrous oxide, fluorescein, fructose, fumaric acid, fumaryl diketopiperazine, gadolinium oxide, galactaric acid, galactose, gamma cyclodextrin, genistein, gentisic acid, gentisic acid ethanolamide, gentisic acid ethanolamine, gluceptate sodium, gluconic acid, gluconolactone, glucosamine, glucose, glucuronic acid, glutamic acid, glutamic acid hydrochloride, glutamine, glutaric acid, glutathione, glyceryl caprylate, glyceryl dibehenate, glyceryl distearate, glyceryl isostearate, glyceryl laurate, glyceryl monostearate, glyceryl oleate, glyceryl palmitate, glyceryl palmitostearate, glyceryl ricinoleate, glyceryl stearate, glyceryl stearate-laureth-23, glyceryl stearate/peg stearate, glyceryl stearate/peg-100 stearate, glyceryl stearate/peg-40 stearate, glyceryl stearate-stearamidoethyl diethylamine, glyceryl trioleate, glycine, glycine hydrochloride, glycol distearate, glycol stearate, glycolic acid, glycyrrhizin, guanidine hydrochloride, hexylresorcinol, hippuric acid, histidine, hyaluronate sodium, hydrocortisone, hydroquinone, hydrous-citric acid, hydroxyethylpiperazine ethane sulfonic acid, hydroxyoctacosanyl hydroxystearate, hydroxyprogesterone caproate, hydroxypropyl beta-cyclodextrin, hystrene, illicium anisatum, imidazole, imidurea, indigotindisulfonate sodium, iodoxamic acid, iofetamine hydrochloride, ipriflavone, isoleucine, isopropyl isostearate, isopropyl myristate, isopropyl myristate-myristyl alcohol, isopropyl palmitate, isopropyl stearate, isostearic acid, isostearyl alcohol, lactate, lactitol monohydrate, lactobionic acid, lactose, landalgine, lanolin, lauralkonium chloride, lauramine oxide, laureth sulfate, lauric acid, lauric diethanolamide, lauric myristic diethanolamide, lauroyl sarcosine, lauryl lactate, lauryl sulfate, lecithin, leucine, levomenthol, levulinic acid, lidofenin, 1-sodium lactate, lysine, maleic acid, malic acid, malonic acid, maltitol, maltodextrin, maltol, maltose anhydrous, mandelic acid, mannitol, maprofix, mebrofenin, medium-chain triglycerides, medronate disodium, medronic acid, menthol, metacresol, methionine, methyl salicylate, methyl stearate, methylchloroisothiazolinone, methylisothiazolinone, methylparaben, methylparaben sodium, miripirium chloride, mono and diglyceride, monobasic sodium phosphate, monobasic sodium phosphate anhydrous, monobasic sodium phosphate dihydrate, monobasic sodium phosphate monohydrate, monoglyceride citrate, monoglycerides, monosodium citrate, monosodium glutamate, monostearyl citrate, monothioglycerol, myristic acid, myristyl alcohol, myristyl lactate, niacinamide, nicotinamide, nicotinic acid, N-methyl glucamine, octanoic acid, oleth-20, oleyl alcohol, oleyl oleate, orotic acid, oxalic acid, oxidronate disodium, oxyquinoline, palmitamine oxide, palmitic acid, pamoic acid, pentadecalactone, pentaerythritol cocoate, pentasodium pentetate, pentetate calcium trisodium, pentetic acid, phenol, phenonip, phenoxyethanol, phenylalanine, phenylethyl alcohol, phospholipid, piperazine, piperazine hexahydrate, procaine, product wat, proline, propenyl guaethol, propyl gallate, propylene carbonate, propylene glycol, propylene glycol-lecithin, propylene glycol alginate, propylene glycol diacetate, propylene glycol dicaprylate, propylene glycol monolaurate, propylene glycol monopalmitostearate, propylene glycol palmitostearate, propylene glycol ricinoleate, propylene glycol/diazolidinyl urea/methylparaben/propylparben, propylparaben, propylparaben sodium, p-toluenesulfonic acid, pyridoxamine, pyridoxine (4-pyridoxic acid), quercetin, resveratrol, riboflavin, saccharin, saccharin calcium, saccharin sodium, saccharin sodium anhydrous, salicylic acid, saturated fatty acid esters, sebacic acid, serine, sodium 1,2-ethanedisulfonate, sodium 2-naphthalenesulfonate, sodium acetate, sodium acetate anhydrous, sodium alginate, sodium alkyl sulfate, sodium aluminium silicate, sodium ascorbate, sodium benzoate, sodium bicarbonate, sodium bisulfate, sodium bisulfate acetone, sodium bisulfite, sodium bitartrate, sodium borate, sodium borate decahydrate, sodium carbonate, sodium carbonate decahydrate, sodium carbonate monohydrate, sodium carboxymethyl beta-glucan (ds 065-085), sodium caseinate, sodium cellulose, sodium cetostearyl sulfate, sodium chlorate, sodium chloride, sodium chloride injection, sodium cholesteryl sulfate, sodium citrate, sodium citrate hydrous, sodium cocoyl sarcosinate, sodium cyclamate, sodium desoxycholate, sodium dithionite, sodium dodecylbenzenesulfonate, sodium ethylparaben, sodium formaldehyde sulfoxylate, sodium gluconate, sodium hydroxide, sodium hypochlorite, sodium iodide, sodium lactate, sodium laureth-2 sulfate, sodium laureth-3 sulfate, sodium laureth-5 sulfate, sodium lauroyl sarcosinate, sodium lauryl sulfate, sodium lauryl sulfoacetate, sodium metabisulfite, sodium nitrate, sodium oleate, sodium phosphate, sodium phosphate dihydrate, sodium phosphite, sodium polyacrylate, sodium polyacrylate (2500000 MW), sodium polymetaphosphate, sodium propionate, sodium pyrophosphate, sodium pyrrolidone carboxylate, sodium starch glycolate, sodium starch glycolate type a corn, sodium starch glycolate type a potato, type B potato sodium starch glycolate, sodium stearate, sodium stearyl fumarate, sodium succinate hexahydrate, sodium sulfate, sodium sulfate anhydrous, sodium sulfate decahydrate, sodium sulfite, sodium sulfosuccinated undecyclenic monoalkylolamide, sodium tartrate, sodium thioglycolate, sodium thiomalate, sodium thiosulfate, sodium thiosulfate anhydrous, sodium trimetaphosphate, sodium tripolyphosphate, sodium xylenesulfonate, sorbic acid, sorbitan, sorbitan isostearate, sorbitan monolaurate, sorbitan monooleate, sorbitan monopalmitate, sorbitan monostearate, sorbitan sesquioleate, sorbitan trioleate, sorbitan tristearate, sorbitol, squalane, stannous 2-ethylhexanoate, stearalkonium chloride, stearalkonium hectorite/propylene carbonate, stearamidoethyl diethylamine, stearates, stearic acid, stearic diethanolamide, stearoxytrimethylsilane, stearyl alcohol, succinic acid, sucralose, sucrose, sucrose distearate, sucrose laurate, sucrose palmitate, sucrose polyesters, sucrose stearate, sucrose syrup, sulfacetamide sodium, sulfobutylether beta-cyclodextrin, tagatose, tartaric acid, tegacid, tert-butylhydroquinone, tetrofosmin, theophylline, thimerosal, threonine, thymol, tocopherol, tocophersolan, tragacanth, triacetin, tribasic sodium phosphate, tribasic sodium phosphate monohydrate, tribehenin, tricaprylin, triceteareth-4 phosphate, triethanolamine lauryl sulfate, triethyl citrate, trihydroxystearin, trilaneth-4 phosphate, trilaureth-4 phosphate, trimyristin, tris, trisodium citrate dihydrate, trisodium hedta, tristearin, trolamine, tromantadine, tromethamine, tryptophan, tyloxapol, tyrosine, undecylenic acid, urea, urethane, ursodiol, valine, vanillin, versetamide, viscarin, vitamin E, vitamin E acetate, vitamin K5, xylitol, and zinc sulfate. See also U.S. Pat. No. 7,927,613, which is incorporated herein by reference in its entirety. Other pharmaceutically acceptable coformers include those delineated in the "Generally Regarded as Safe" ("GRAS") and/or the US FDA "Everything Added to Food in the United States" ("EAFUS") lists.

In certain embodiments, at least one of the one or more pharmaceutically acceptable coformers is selected from the group consisting of caffeine, urea, p-aminobenzoic acid, theophylline, benzyl benzoate, and nicotinamide. In other embodiments, the one or more pharmaceutically acceptable coformers is other than those selected from the group consisting of caffeine, urea, p-aminobenzoic acid, theophylline, benzyl benzoate, and nicotinamide. In other embodiments, the one or more pharmaceutically acceptable coformers is other than those selected from the group consisting of acetamide, benzamide, 2-aminothiazole, and isoniazide. In still other embodiments, the one or more pharmaceutically acceptable coformers is an amino acid (e.g., proline, e.g., D-proline or L-proline, or racemic proline). In another embodiment, the one or more pharmaceutically acceptable coformers is a 5-10 (e.g., 5-9, 5-6, or 5) membered heteroaryl, e.g., a nitrogen-containing heteroaryl, e.g., imidazole.

In certain embodiments, at least one of the one or more pharmaceutically acceptable coformers is a second API. In certain of these embodiments, the second API is independently selected from (−)-amlodipine, (−)-halofenate, (R)-salbutamol, (R)-salbutamol, (R,R)-formoterol, (S)-doxazosin, (S)-fluoxetine, (S)-oxybutynin, 1,2-naphthoquinone, 17-methyltestosterone, 17α-hydroxyprogesterone, 195mPt-cisplatin, 1-naphthyl salicylate, 1-naphthylamine-4-, 1-theobromineacetic, 1α-hydroxycholecalciferol, 2,4,6-tribromo-m-cresol, 2,6-diamino-2'-butyloxy-3,5'-azopyridine, 2-[[[(1r)-2-(1h-imidazol-4-yl)-1-methylethyl]imino]phenylmethyl]-phenol, 21-acetoxypregnenolone, 2-amino-4-picoline, 2-aminothiazole, 2-ethoxybenzoic acid, 2-naphthol, 2-naphthyl benzoate, 2-naphthyl lactate, 2-naphthyl salicylate, 2-p-sulfanilylanilinoethanol, 2-thiouracil, 3',3",5',5"-tetra-bromophenolphthalein, 3-amino-4-hydroxybutyric acid, 3-Bromo-D-camphor, 3-Hydroxycamphor, 3-O-Lauroylpyridoxol Diacetate, 3-pentadecylcatechol, 3-quinuclidinol, 4,4'-oxydi-2-butanol, 4,4'-sulfinyldianiline, 4-amino-3-hydroxybutyric acid, 4-amino-3-phenylbutyric acid, 4-aminosalicylic acid, 4-chloro-m-cresol, 4-hexylresorcinol, 4-salicyloylmorpholine, 5'-nitro-2'-propoxyacetanilide, 5-aminolevulinic acid, 5-azacitidine, 5-bromosalicyl-hydroxamic acid, 5F-DF-203, 5-FU, 5-HT3 antagonists, 6-azauridine, 6-mercaptopurine, 8-hydroxyquinoline, 9-aminocamptothecin, A-151892, A-5021, abacavir, abaperidone, abarelix, abciximab, abecarnil, abetimus, abiraterone, ABLC, ABT-751, AC-5216, acadesine, acamprosate, acamprosate, acarbose, acebrophylline, acebutolol, acecainide, acecarbromal, aceclofenac, acedapsone, acediasulfone, acefylline, aceglutamide, aceglutamide, acemetacin, acenocoumarol, aceponate, acetal, acetamidoeugenol, acetaminophen, acetaminosalol, acetanilide, acetarsone, acetazolamide, acetiamine, acetohexamide, acetohydroxamic acid, acetophenazine, acetophenide, acetophenone, acetosulfone, acetoxolone, acetrizoat, acetyl, acetylcarnitine, acetylcholine, acetylcholine, acetylcysteine, acetylleucine, acetylpheneturide, acetylsalicylate, acetylsalicylic acid, aciclovir, acifran, acipimox, acitazanolast, acitretin, aclarubicin, aclatonium, aconitine, acranil®, acriflavine, acrisorcin, acrivastine, acrivastine, actagardine derivative, actarit, ACTH, acyclovir, adapalene, ADCON-L, adefovir, adefovir dipivoxil, adenoscan, adenosine triphosphate, ADEPT, adinazolam, adiphenine, ADL-10-0101, adrafinil, adrenalone, adrenochrome, adrogolide, AEOL-10150, aesthinol, AET, AF-2259, afloqualone, AG-041R, AG-2037, AGN-194310, agomelatine, ahistan, AHL-157, AIT-034, AIT-202, AJ-9677, AJG-049, ajmaline, akzo desogestrel, alacepril, alapivoxil, albaconazole, albendazole, albuterol, albutoin, alclofenac, alclometasone, alcuronium, aldioxa, aldol, aldosterone, alendronate, alendronic acid, alexidine, alfacalcidol, alfadolone, alfaxalone, alfentanil, alfimeprase, alfuzosin, alfuzosin, algestone, algestone, algin, alglucerase, alibendol, aliskiren, alitertinoin, alizapride, alkannin, alkofanone, allantoin, allobarbital, allopurinol, allyl isothiocyanate, allylestrenol, almagate, alminoprofen, almitrine, almotriptan, aloe-emodin, aloin, alosetron, alovudine, aloxiprin, alpha-, alpha-1 protease, alphaprodine, alpidem, alpiropride, alprazolam, alprenolol, alsactide, ALT-711, Althiazid, altinicline, altretamine, aluminium chloride hexahydrate, aluminon, aluminum acetate solution, aluminum chlorate, aluminum hydroxychloride, aluminum potassium sulfate, aluminum sodium sulfate, alusulf, alverine, alvimopan, alvocidib, ALX-0646, AM-24, AM-36, AM-477, amantadine, amantanium, ambazon, ambenonium, ambrisentan, ambroxol, ambucaine, ambuphylline, ambusid, ambutonium bromide, amcinonide, AMD-3100, amdinocillin, amdinocillin pivoxil, amdoxovir, amelubant, americaine, amezinium, amfenac, amidephrine, amidinomycin, amifostine, amiglumide, amikacin, amiloride, aminacrine, amineptine, aminitrozole, amino acid preparations, aminocaproic acid, aminoglutethimide, aminoguanidine, aminohippurate, aminometradine, aminopentamide, aminophylline, aminopromazine, aminopyrine, aminoquinuride, aminorex, amiodarone, amiodipine, amiphenazole, amiprilose, amisulpride, amitriptyline, amitriptyline+ketamine, amitriptylinoxide, amlexanox, ammoniacum, ammoniated mercuric chloride, ammonium benzoate, ammonium mandelate, ammonium salicylate, ammonium valerate, amobarbital, amocarzine, amodiaquin, amorolfine, amoscanat, amosulalol, amotriphene, amoxapine, amoxicillin, amoxicillin+potassium clavulan, AMPAlex, amphetamine, amphetaminil, amphotericin B, ampicillin, ampiroxicam, ampligen, amprenavir, amrinose, amrubicin, amsacrine, amtolmetin guacil, amylocaine, AN-152, anabolic steroids, anagestone, anagrelide, anastrozole, anazolene, ancitabine, ancrod, andolast, androisoxazole, androstenediol, anecortave, anethole, anethole trithione, angiogenix, angiotensin, anhydrovinblastine, anidulafungin, anilerdine, aniracetam, anisindione, anisomycin, anisotropine, anistreplase, antazoline, anthiolimine, anthralin, anthramycin, anthrarobin, anthrax inhibitor, anti-angiogenic, anticort, antidepressants, anti-invasins, antimony potassium tartrate, antimony sodium thioglycollate, antimony thioglycollamide, antiprogestin, antipyrine, antipyrine salicylate, antithrombin III, anxiolytics, AP-521, AP-5280, apalcillin, apaziquone, apazone, apocodeine, apomine, apomorphine, apraclonidine, aprepitant, aprindine, aprobarbital, apronalide, aprotinin, aptiganel, AQ4N, aquavan, AR-116081, AR-A2, arachidonic acid, aranidipine, arbekacin, arbidol, arbutamine, arcitumomab, ardeparin, arecoline, argatroban, arginine, Ariflo®, aripiprazole, arofylline, arotinolol, arsacetin, arsenic trioxide, arsphenamine, arteether, arteflene, artemether, artemisinin, artemotil, artesunate, arzoxifene, AS-3201, ASA, ascaridole, ascorbic acid, asenapine, asimadoline, asocarboxazid, asoprisnil, asoxime, aspartic acid, aspidin, aspidinol, aspirin, aspirin dipyridamole, aspoxicillin, AST-120, astemizole, asulacrine, AT-1015, atamestane, atazanavir, atenolol, atenolol+chlorthalidone, atenolol+nifedipine, atevirdine, atipamezole, atiprimod dimaleate, ATL-146e, atomoxetine, atorvastatin, atosiban, atovaquone, atovaquone+proguanil, atracurium, atrasentan, atrial natriuretic, atrolactamide, atropine, augmentin, auranofin, aurothioglucose, avasimibe, avobenzone, AWD-12-281, azacitidine, azacyclonol, azanidazole, azapropazone, azaserine, azasertron, azatadine, azathipprine, AZD-4282, AZD-6140, azelaic acid, azelastine, azelnidipine, azidamfenicol, azidocillin, azimilide, azintamide, azithromycin, azlocillin, azosemide, aztreonam, azulene, bacampicillin, bacitracin, baclofen, baicalein, balofloxacin, balsalazide, bambuterol, bamethan, bamifylline, bamipine, barbital, barnidipine, BAS-118, basic alumina, baslilximab, batimastat, batroxobin, Bay-41-2272, Bay-41-8543, BAY-43-9006, BAY-57-1293, bazedoxifen, BBR-3464, BBR-3576, BBR-3610, BCH-1868, bebeerine, beclamide, beclometasone, befloxatone, befunolol, bemegride, benactyzine, benazepril, bencyclane, bendazac, bendroflumethiazide, benetonide, benexate, benfluorex, benfotiamine, benfurodil, benidipine, benorylate, benoxaprofen, benoxinate, benperidol, benproperine, benserazide, bentazepam, bentiromide, bentoquatam, benzafibrate, benzalkonium, benzarone, benzathine, benzbromarone, benzethonium, benzetimide, benzilonium, benziodarone, benznidazole, benzocaine, benzoctamine, benzonatate, benzoxonium chloride, benzoyl peroxide, benzoylpas, benzphetamine, benzpiperylon, benzquinamide, benzthiazide, benztropine, benzydamine, benzyl benzoate, benzylhydrochloro-thiazide, benzylmorphine, bephenium, bepotastine, bepridil, beraprost, berberine, bergapten, bermoprofen, besipirdine, betahistine, betaine, betamethasone, betamipron, betasine, betaxolol, betazole, bethanechol, bethanidine, betoxycaine, bevantolol, bevonium, bexarotene, bezitramide, BG-9928, BIA-2-024, BIA-2-093, BIA-3-202, bialamicol, biapenem, bibenzonium, bibrocathol, bicalutamide, bicifadine, bicisate, bicyclic, bidisomide, bietamiverine, bietanautine, bietaserpine, bifermelane, bifluranol, bifonazole, bimatoprost, bimoclomol, bimosiamose, binifibrate, binodenoson, biomed-101, biotin, biperiden, biriperone, birlcodar, bisacodyl, bisantrene, bisbentiamine, bisdequalinium, bismuth, bismuth, bismuth, bismuth aluminate, bismuth ethyl, bismuth sodium, bismuth sodium triglycollamate, bismuth subcarbonate, bismuth subgallate, bismuth subnitrate, bismuth subsalicylate, bisoprolol, bisoprolol+HCTZ, bisoprolol+ trichloromethiazide, bisoxatin, bithionol, bitolterol, bitoscanat, BL-3875, bleomycin, blonanserin, BMS-184476, BMS-387032, BN-82451, BNP-7787, BO-653, bolandiol, bolasterone, boldenone, bopindolol, bornyl chloride, bornyl salicylate, bortezomib, bosentan, bradycor, brain natriuretic, brallobarbital, brasofensine, brequinar, bretylium, brilliant green, brimonidine, brinzolamide, brivudin, brodimoprim, bromazepam, bromfenac, bromhexine bromide, bromindione, bromisovalum, bromocriptine, bromo-diphenhydramine, bromoform, bromopride, bromo-salicychloranilide, bromperidol, brompheniramine, broparoestrol, bropirimine, brostallicin, brotizolam, brovincamine, broxyquinoline, brozuridine, brucine, bucetin, bucillamine, bucindolol, bucladesine, buclizine, buclosamide, bucolome, bucricaine, bucumolol, budesonide, budesonide+formoterol, budipine, budralazine, bufeniode, bufetolol, bufexamac, buflomedil, buformin, bufuralol, bumadizon, bumetanide, bunaftine, bunamiodyl sodium, bunazosin, bunitrolol, bupivacaine, bupranolol, buprenorphine, bupropion, buramate, buserelin, buspirone, busulfan, busulfan, butabarbital, butacaine, butacetin, butalamine, butalbital, butallylonal, butambcen, butamirate, butanilicaine, butaperazine, butaverine, butazolamide, butedronic acid, butenafine, butethal, butethamate, butethamine, buthalital, buthiazide, butibufen, butidrine, butobendine, butoconazole, butoctamide, butofilolol, butorphanol, butoxycaine, butriptyline, butropium, butylthiolaurate, butyrate propio, buzepide, BVT-5182, BXT-51072, C-1311, cabergoline, cabergoline, cacodylic acid, cactinomycin, cadexomer iodine, cadmium salicylate, cadralazine, cafaminol, caffeine, calcifediol, calcipotriene, calcipotriol, calcipotriol+beclometasone, calcitriol, calcium 3-aurothio-2-propanol-1-sulfonate, calcium acetylsalicylate, calcium bromolactobionate, calcium carbonate, calcium gluconate, calcium glycerophosphate, calcium hopantothenate, calcium iodobehenate, calcium iodosterate, calcium lactate, calcium levulinate, calcium mesoxalate, calcium N-carbamoylaspartate, calcium polycarbophil, calcium propionate, calcium succinate, caldaret, calusterone, camazepam, camostat, camphor, camphorate, camphotamide, camptothecin, candesartan, candesartan cilexetil, candoxatril, canertinib, canrenone, cantharidin, cantuzumab mertansine, capecitabine, capobenic acid, capravirine, capromab, capsaicin cream, captodiamine, captopril, captopril+HCTZ, capuride, carabersat, caramiphen, carazolol, carbachol, carbamazepine, carbamide peroxide, carbarsone, carbaryl, carbazochrome, carbendazim, carbenicillin, carbenoxolone, carbetapentane, carbicarb, carbidopa, carbidopa+levodopa-1, carbimazole, carbinoxamine, carbocloral, carbocysteine, carbon tetrachloride, carbonate gel, carboplatin, carboprost, carboprost, carboquone, carbromal, carbubarb, carbutamide, carbuterol, carfimate, carglumic acid, cargutocin, carindacillin, cariporide, cariporide, carisoprodol, carmofur, carmoxirole, carmustine, carnitine, caroverine, caroxazone, carphenazine, carpipramine, carprofen, carsalam, carteolol, carticaine, carubicin, carumonam, carvacrol, carvedilol, carvone, cascarillin, caspofungin, catechin, cathepsin K inhibitors, cathepsin S inhibitors, CC-401, CCI-779, CCR5 antagonists, CDC-394, CDC-801, CEE-03-310, cefactor, cefadroxil, cefalexin, cefalexin pivoxil, cefamandole, cefatrizine, cefazedone, cefazolin, cefbuperazone, cefcapene pivoxil, cefclidin, cefdinir, cefditoren pivoxil, cefepime, cefetamet, cefetamet pivoxil, cefixime, cefmenoxime, cefmetazole, cefminox, cefodizime, cefonicid, cefoperazone, cefoperazone+sulbactam, ceforanide, cefoselis, cefotazime, cefotetan, cefotiam, cefotiam hexetil, cefoxitin, cefozopran, cefpimizole, cefpiramide, cefpirome, cefpodoxime, cefprozil, cefroxadine, cefsulodin, ceftazidime, cefteram, ceftezole, ceftibuten, ceftizoxime, ceftizoxime, ceftriaxone, cefuroxime, cefuroxime axetil, cefuzonam, celecoxib, celgosivir, celiprolol, cellulose ethyl, CEP-1347, CEP-701, cephacetrile, cephaeline, cephalexin, cephaloglycin, cephaloridine, cephalosporin C, cephalothin, cephapirin, cephradine, cerivastatin, ceronapril, certoparin, ceruletide, cerviprost, cetalkonium, cetamolol, cethexonium, cethromycin, cetiedil, cetirizine, cetirizine, cetirizine+ pseudoephedrine, cetotiamine, cetoxime, cetraxate, cetrimonium, cetrorelix, cetyldimethylethyl-ammonium, cetylpyridinium, cevimeline, CG-1521, chaulmoogric acid, chenodiol, CHF-3381, chlophedianol, chloracizine, chloral, chlorambucil, chloramine-B, chloramine-T, chloramino-chloramphenicol, chlorazanil, chlorbenzoxamine, chlorbetamide, chlorcyclizine, chlordantoin, chlorguanide, chlorhexadol, chlorhexidine, chloriazepoxide, chlorisondamine, chlormadinone, chlormerodrin, chlormezanone, chlormidazole, chlornaphazine, chloroazodin, chlorophyll, chloroprednisone, chloroprocaine, chloropyramine, chloroquine, chlorothen, chlorothiazide, chlorotrianisene, chloroxine, chloroxylenol, chlorozotocin, chlorphenamine, chlorphenesin, chlorpheniramine, chlorphenoxamide, chlorphenoxamine, chlorphentermine, chlorproethazine, chlorproguanil, chlorproguanil+dapsone, chlorpromazine, chlorpropamide, chlorprothixene, chlorquinaldol, chlortetracycline, chlorthalidone, chlorthenoxazine(e), chlorzoxazone, cholic acid, choline, choline theophyllinate, choline-L-alfoscerate, chromocarb, chromonar, chrysoidine, CHS-828, CI-1031, CI-1040, cibenzoline, ciclesonide, cicletanine, ciclonicate, ciclopirox, ciclosidomine, ciclosporin A, cidofovir, cifenline, cilansetron, cilastatin, cilazapril, cilengitide, cilnidipine, cilomilast, cilostazol, cimetidine, cimetropium, cinacalcet, cinchonidine, cinchonine, cinchophen, cinepazet, cinepazide, cinepazide, cinitapride, cinmetacin, cinnamedrine, cinnarizine, cinolazepam, cinoxacin, cinoxate, cinromide, cioteronel, cipamfylline, cipralisant, ciprofibrate, ciprofloxacin, ciprofloxacin+ciramadol, cisapride, cisatracurium, cisplatin, citalopram, citicoline, Citiolone, citrate, citric acid, citrulline, cizolirtine, CJ-13610, CKD-602, cladribine, clanobutin, clarithromycin, clavulan, clavulanate disodium, clavulanic acid, clebopride, clemastine, clemizol, clenbuterol, clentiazem, clevidipine, clevudine, clidanac, clidinium, clinafloxacin, clindamycin, clindamycin, clindamycin+tretinoin, clinofibrate, clinprost, clobazam, clobenfurol, clobenoside, clobenzepam, clobenzorex, clobenztropine, clobetasol, clobetasone, clobutinol, clocapramine, clocinizine, cloconazole, clocortolone, clodronate, clodronic acid, clofarabine, clofazimine, clofenamide, clofibrat, clofibric acid, cloflucarban, clofoctol, cloforex, clomacran, clomestrone, clometacin, clomethiazole, clometocillin, clomiphene, clomipramine, clomocycline, clonazepam, clonidine, clonitazene, clonitrate, clonixin, clopamid, clopenthixol, cloperastine, clopidogrel, clopirac, cloprednol, cloranolol, clorazepic acid, clorexolone, cloricromene, clorindione, clorprenaline, clortermine, clospirazine, clostebol, clothiapine, clotiazepam, clotrimazole, clotrimazole+betamethasone, cloxacillin, cloxazolam, cloxotestosterone, cloxyquin, clozapine, CMI-392, CMT-3, CNI-1493, CNS-5161, cobamamide, cocaethylene, cocaine, codeine, cofactor, colchicine, colesevelam, colestilan, colestipol, colforsin daropate, colfosceril, collagraft, colocynthin, colpormon, coluracetam, combretastatin A-4 prodrug, compound B, conivaptin conjugate, connettivina, convallatoxin, coparaffinate, corticorelin ovine, corticosterone, cortisone, cortivazol, cosyntropin, cotarnine, cotinine, co-trimazine, coumetarol, CP-248, CP-461, CPC-211, CPI-1189, CRA-0450, creatinol-O-phosphate, CRL-5861, crobenetine, croconazole, cromoglicic acid, cromolyn, cropropamide, crotamiton, crotethamide, crystacide, CS-502, CS-758, CS-834, CT-052923, CT-32228, cupric citrate, cuproxoline, CVT-2584, CX-659S, cyacetacide, cyamemazine, cyanidin, CYC400, cyclacillin, cyclandelate, cyclazocine, cyclexanone, cyclexedrine, cyclidrol, cyclin D1 inhibitors, cyclizine, cyclobarbital, cyclobendazole, cyclobenzaprine, cyclobutyrol, cyclocumarol, cyclodrine, cyclofenil, cycloguanil, cyclomethycaine, cycloniumelodide, cyclopentamine, cyclopenthiazide, cyclopentobarbital, cyclopentolate, cyclophosphamide, cyclopiroxalamine, cycloserine, cyclothiazide, cyclovalone, cymarin, cymserine, cynarin(e), cyp26 inhibitors, cyproheptadine, cyproterone, cysteamine, cystic fibrosis ther, cytarabine, D-24851, D-4418, DA-5018, DA-6034, DA-7867, DA-7911, DA-8159, dacarbazine, daclizumab, dactinomycin, dalbavancin, dalfopristin, dalfopristin+quinupristin, dalteparin, daltroban, danaparoid, danazol, danthron, dantrolene, dapiprazole, dapivirine, dapoxetine, dapsone, daptomycin, darbepoetin alfa, darifenacin, daunorubicin, DAX<SciClone, DB-67, D-camphocarboxylic, DCF-987, DDT, deaminooxytocin, deanol, debrisoquin, decamethonium, decimemide, decitabine, decloprамide, deferiprone, deferoxamine, deflazacort, defosfamide, degarelix, dehydroascorbic acid, dehydroemetine, dehyrdocholic acid, delapri+manidipine, delapril, delavirdine, delmadinone, delmopinol, delorazepam, delucemine, demanyl, demecarium, demeclocycline, demecolcine, demegestone, demexiptilline, denaverine, dendrimers, denileukin diftitox, denopamine, denopterin, deoxycholic acid, deoxycorticosterone, deoxydihydro-streptomycin, deoxyepinephrine, depreotide, depsipeptide, deptropine, dequalinium, dersalazine, deserpidine, desferrioxamine, desflurane, desipramine, deslanoside, desloratadine, deslorelin, desmopressin, desogestrel, desogestrel+estradiol, desogestrel+ethinylestrad (1), desomorphine, desonide, desoximetasone, detaxtran, devacade, dexamethasone, dexanabinol, dexecadotril, dexefaroxan, dexetimide, dexibuprofen, dexketoprofen, dexloxiglumide, dexmedetomidine, dexmethylphenidate, dexpanthenol, dexrazoxane, dextran-1, dextranomer, dextroamphetamine, dextromethorphan, dextromoramide, dextropropoxyphene, dezocine, DF-1012, DFA-IV, D-fenchone, D-glucuronolactone, Diab II, diacerein, diampromide, diamthazole, diathymosulfone, diatrizoate, diazepam, diaziquone, diazoxide, dibekacin, dibenzepin, dibromopropamidine, dibucaine, dichloralphenazone, dichloramine T, dichlorisone, dichlorobenzyl alcohol, dichlorohydrin, dichlorophen, dichlorophenarsine, dichlorphenamide, diclofenac, diclofenac+HA, dicloxacillin, dicoumarol, dicumarol, dicyclomine, didanosine, dideoxyadenosine, didox, dienestrol, dienogest, dienogest+estradiol, diethadione, diethazine, diethylamide, diethylbromo-acetamide, diethylcarbamazine, diethylpropion, diethylstilbestrol, difemerine, difenamizole, difenoxin, difenpiramide, diflomotecan, diflorasone, difloxacin, diflucortolone, diflunisal, difluprednate, digitalin, digitoxin, digoxin, dihexyverine, dihydralazine, dihydrocodeine, dihydrocodeinone enol, dihydroergocryptine, dihydroergocryptine, dihydroergotamine, dihydromorphine, dihydrostreptomycin, dihydrotachysterol, dihydroxyaluminum, diisopromine, diisopropyl paraoxon, diisopropylamine, dilazep, dilevalol, diloxanide, diltiazem, dimecrotic acid, dimefline, dimeglumine, dimemorfan, dimenhydrinate, dimenoxadol, dimepheptanol, dimercaprol, dimetacrine, dimethadione, dimethazan, dimethindene, dimethisoquin, dimethisterone, dimethocaine, dimethoxanate, dimethyl sulfoxide, dimethylthiambutene, dimetofrine, dimorpholamine, dinoprostone, diosmectite, diosmin, dioxadrol, dioxaphetyl, dioxethedrine, dioxybenzone, diphemanil, diphenadione, diphencyprone, diphenhydramine, diphenidol, diphenoxylate, diphenylpyraline, diphetarsone, diphtheria & tetanus toxoids and acellular pertussis vaccine adsorbed, dipipanone, dipivefrin, dipyridamole, dipyridamole, dipyrocetyl, dipyrone, diquafosol, dirithromycin, disodium pamidronate, disofenin, disopyramide, distigmine, disulfamide, disulfiram, ditazol, dithiazanine, dithranol, ditiocarb, dixanthogen, dixyrazine, DJ-927, DK-507k, DL-Lactic Acid, DMDC, DMXAA, DNA Stealth, dobesilate, dobutamine, docarpamine, docetaxel, docosahexaenoic acid, docosanol, docusate, dofetilide, dolasetron mesilate, domiodol, domiphen, domitroban, domperidone, donepezil, donitriptan, dopamine, dopexamine, doramapimod, doranidazole, doripenem, dorzolamide, dorzolamide+timolol, dosmalfate, dosulepine, dotarizine, dothiepin, doxacurium, doxapram, doxazosin, doxefazepam, doxenitoin, doxepin, doxercalciferol, doxifluridine, doxofylline, doxorubicin, doxycycline, doxylamine, DPC-817, DPI-3290, DQ-113, drofenine, droloxifene, drometrizole, dromostanolone, dronabinol, dronedarone, droperidol, droprenilamine, dropropizine, drospirenone, drotaverine, drotebanol, droxicam, droxidopa, droxidopa, DU-125530, duloxetine, duramycin, durapatite, dutasteride, DW-1141, DW-286a, DW-471, DX-9065a, DY-9760e, dyclonine, dydrogesterone, dymanthine, dyphyllin, E-1010, E-2101, E2F antagonists, E-3620, E-5564, E-5842, E-6259, EAA-90, ebastine, eberconazole, ebrotidine, ebselen, eburnamonine, ecabapide, ecabet, ecadotril, ecgonidine, ecgonine, echothiophate, econazole, ecopipam, ecraprost, ectylurea, ED-71, edaravone, edatrexate, edetate calcium disodium, edetate disodium, edetate sodium, edetate trisodium, edonentan, edotreotide, edoxudine, edrecolomab, edrophonium, efalith, efaproxiral, efavirenz, efletirizine, eflornithine, efloxate, eflucimibe, efonidipine, EGIS-7229, eglumegad, egualen, elarofiban, elcatonin, elcosapentaenoic acid, eledoisin, eletriptan, elgodipine, ellagic acid, elliptinium, eltoprazine, elvucitabine, elzasonan, embelin, embramine, emedastine, emepronium, emetine, emitefur, EMM-210525, emodin, emorfazone, EMR-62203, emtricitabine, emylcamate, enalapril, enalaprilat, enallylpropymal, encainide, enciprazine, endralazine, enfenamic acid, enflurane, enilconazole, eniluracil, ENMD-0995, enocitabine, enol-3-IPA, enoxacin, enoxaparin, enoximone, enoxolone, enprostil, enrasentan, entacapone, entecavir, enviomycin, eoinephrine, epalrestat, epavir, EPC-K1, eperisone, epervudine, ephedrine, epicillin, epimestrol, epinastine, epirizole, epirubicin, epitiostanol, eplerenone, eplivanserin, epoprostenol, epostane, eprazinone, epristeride, eprosartan, eprozinol, eptapirone, eptaplatin, eptastigmine, eptazocine, eptifibatide, equilenin, equilin, ERA-923, erdosteine, ergocornine, ergocorninine, ergoloid mesylates, ergonovine, ergosterol, ergotamine, eritadenine, erlotinib, ertapenem, erythrityl tetranitrate, erythrocentaurin, erythromycin acistrate, erythromycin erythrophleine, erythromycin estolate, erythromycin glucoheptonate, erythromycin lactobionate, erythromycin propionate, erythromycin stearate, erythromycin stinoprate, esaprazole, escitalopram, esculin, eseridine, esmolol, esomeprazole, estazolam, ester, estradiol, estradiol, estramustine, estriol, estrogen, estrone, eszopiclone, etafedrine, etafenone, etamiphyllin, etanercept, etanidazole, etaqualone, eterobarb, ethacridine, ethacrynic acid, ethadion, ethambutol, ethamivan, ethamsylate, ethanolamine, ethaverine, ethchlorvynol, ethenzamide, ethiazide, ethinamate, ethinyl estradiol, ethinyl estradiol, ethinyl estradiol, ethionamide, ethisterone, ethoheptazine, ethopropazine, ethosuximide, ethotoin, ethoxzolamide, ethybenztropine, ethyl alcohol, ethyl biscoumacetate, ethyl chloride, ethyl dibunate, ethyl ether, ethyl icosapentate, ethyl loflazepate, ethyl loflazepate, ethylamine, ethylene, ethylestrenol, ethylidene, ethylmethyl-thiambutene, ethylmorphine, ethylnorepinephrine, ethynodiol, ethynylcytidine, etidocaine, etidronate, etidronic acid, etifelmin, etifoxine, etilefrin, etilevodopa, etiprednol, etiroxate, etizolam, etodolac, etodroxizine, etofenamate, etofibrate, etofylline, etofylline clofibrate, etofylline nicotinate, etoglucid, etomidate, etomidoline, etonitazene, etonogestrel, etoperidone, etoposide, etoposide phosphate, etoricoxib, etoxadrol, etozolin, etretinate, etryptamine, etymemazine, eucatropine, eugenol, EUK-134, EUK-189, evans blue, everolimus, exalamide, exametazime, exatecan, exemestane, exifone, exisulind, Exosurf®, ezetimibe, Factor IX, Factor VIII, Factor XIII, fadolmidine, fadrozole, falecalcitriol, famciclovir, famotidine, fampridine, fandofloxacin, fantofarone, faropenem, faropenem daloxate, fasidotril, fasudil, fazadinium bromide, febarbamate, febuprol, febuxostat, fedotozine, felbamate, felbinac, felodipine, felypressin, femoxetine, fenbenicillin, fenbufen, fenbutrazate, fencamfamine, fencamine, fenclozic acid, fendiline, fendosal, fenethylline, fenfluramine, fenipentol, fenofibrate, fenoldopam, fenoprofen, fenoterol, fenoverine, fenoxazoline, fenoxedil, fenozolone, fenpentadiol, fenpiprane, fenpiverinium, fenproporex, fenquizone, fenretinide, fenspiride, fentanyl, fentiazac, fenticlor, fenticonazole, fentonium bromide, fepradinol, feprazone, ferric sodium edetate, ferrioxamine B, ferrocholinate, ferrous gluconate, ferumoxytol, fesoterodine, fexofenadine, fibrostat, fidarestat, fiduxosin, finasteride, finrozole, fipexide, FK-960, flavopiridol, flavoxate, flecainide, fleroxacin, flesinoxan, flibanserin, floctafenine, flomoxef, flopropione, florantyrone, flosequinan, floxacillin, floxuridine, fluacizine, fluanisone, fluarizine, fluasterone, fluazacort, flucloronide, flucloxacillin, fluconazole, flucytosine, fludarabine, fludeoxyglucose F18, fludiazepam, fludrocortisone, flufenamic acid, fluindione, flumazenil, flumecinol, flumequine, flumethasone, flumethiazide, flunisolide, flunitrazepam, flunoxaprofen, fluocinolone acetonide, fluocinolone SAL, fluocinonide, fluocortin butyl, fluocortolone, fluorescein, fluoresone, fluorometholone, fluorosalan, fluorouracil, fluoxetine, fluoxymesterone, flupentixol, fluperolone, fluphenazine, flupirtine, fluprednidene acetate, fluprednisolone, fluproquazone, flurandrenolide, flurazepam, flurbiprofen, flurithromycin, flurogestone, flurothyl, fluroxen, fluspirilene, flutamide, flutazolam, fluticasone, flutoprazepam, flutrimazole, flutropium bromide, fluvastatin, fluvoxamine, folic acid, folinic acid, fomepizole, fominoben, fomivirsen, fomocaine, fonazine, fondaparinux, formebolone, formestane, formocortal, formoterol, fosamprenavir, foscarnet, fosfestrol, fosfluconazole, fosfomycin, fosfomycin, fosfosal, fosinopril, fosphenytoin, fotemustine, fropenem, frovatriptan, fructose, fructose-1,6-diphosphate, FTC, FTY-720, fudosteine, fulvestrant, fumagiline, fumagillin, furaltadone, furazabol, furazolidone, furazolium chloride, furonazide, furosemide, fursultiamine, furtrethonium, fusidic acid, G1, YM BioSciences, G25, GABA-A Alpha5, gabapentin, gabexate, gaboxadol, gadobenat, gadobutrol, gadodiamide, gadolinium, gadopentetic acid, gadoteridol, gadoversetamide, gadoxetic acid, galantamine, galanthamine, galarubicin, gallamine triethiodide, gallic acid, gallium maltolate, gallium nitrate, gallopamil, ganaxolone, ganciclovir, ganirelix, ganstigmine, gantofiban, garenoxacin, garnocestim, gatifloxacin, gefarnate, gefitinib, gemcabene, gemcitabine, gemeprost, gemfibrozil, gemifloxacin, gentamicin, gentian violet, gentiopicrin, gentisic acid, gepefrine, gepirone, gestodene, gestodene+ethinylest, gestonorone caproate, gestrinone, gimatecan, giractide, gitoxin, GL-406349, Glafenine, glatiramer, Glibornuride, gliclazide, glimepiride, glipizide, gliquidone, glisolamide, glisoxepid, globulin (human), glucametacin, glucoheptonic acid, gluconic acid, glucosamine, glucosulfone, glufosfamide, glutamic acid, glutaraldehyde, glutethimide, glyburide, glybuthiazol(e), glybuzole, glycerol, glycerophosphate, glycocyamine, glycol salicylate, glyconiazide, glycopyrrolate, glyhexamide, glymidine, glypinamide, GMDP, gold sodium, goserelin, GPI-1485, GPI-5693, graftskin, granisetron, grepafloxacin, griseofulvin, guaiacol, guaiapate, guaiazulene, guaifenesin, guaimesal, gualacolsulfonate, guamecycline, guanabenz, guanadrel, guanethidine, guanfacine, guanoxabenz, guanoxan, gugulipid, gusperimus, GW-280430A, GW-320659, GYKI-16084, hachimycin, halazepam, halcinonide, halobetasol, halofantrine, halometasone, haloperidol, halopredone, haloprogin, halopropane, halothane, haloxazolam, harkoseride, HE-2000, healos, hematoporphyrin, hepronicate, heptabarbital, heptaminol, hetacillin, hetastarch, hexacetonide, hexachlorophene, hexadimethrine, hexafluorenium, hexamethonium, hexamidine, hexapropymate, hexedine, hexestrol, hexestrol Bis(β-diethylaminoethyl ether), hexethal, hexetidine, hexobarbital, hexobendine, hexocyclium methyl sulfate, hexoprenaline, hextend, hexylcaine, HF-0299, HGP-2, HGP-6A, hidrosmin, histamine, Histapyrrodine, histrelin, HM-101, HMN-214, homatropine, homocamfin, homochlorcyclizine, hopantenic acid, HP-228, huperzine A, hyaluronan, hycanthone, hydnocarpic acid, hydralazine, hydrastine, hydrastinine, hydrochlorothiazide, hydrocodone, hydrocortamate, hydrocortisone, hydrocortisone, hydroflumethiazide, hydromorphone, hydroquinidine, hydroquinine, hydroquinone, hydroxid, hydroxocobalamin, hydroxyamphetamine, hydroxychloroquine, hydroxydione, hydroxyethyl ether, hydroxynaphthoate, hydroxypethidine, hydroxyphenamate, hydroxypropyl cellulose, hydroxystilbamidine, hydroxytetracaine, hydroxyzine, Hylan G-F 20, hymecromone, hyoscyamine, hypericin, IACFT, ibandronic acid, ibopamine, ibopamine, Ibritumomab, ibrolipim, ibudilast, Ibufenac, ibuprofen, ibuprofen piconol, ibuproxam, ibutilide, ICA-17043, icodextrin, idarubicin, Idazoxan, IdB-1016, idebenone, IDN-5109, idoxifen, idraparinux, idrocilamide, ifenprodil, ifosfamide, iguratimod, ilaprazole, ilomastat, iloperidone, iloprost trometamol, ILX23-7553, imatinib, imidapril, imidazole salicylate, imipenem, imipramine, imipramine N-Oxide, imiquimod, imolamine, implitapide, improsulfan, inactivated, inaperisone, incadronate, incadronic acid, indalpine, indanazoline, indapamide, indecainid, indeloxazine, indeloxazine, indenolol, indinavir, indiplon, indisetron, indisulam, indobufen, indocyanine green, indometacin, indoprofen, indoramin, induclem, infliximab, inhibitor, inhibitors, inosine pranobex, inositol, inositol niacinate, inverse agonist Mer, iobenguane, iobenzamic acid, iobitridol, iocarmic acid, iocetamic acid, iodamide, iodide, iodine, iodipamide, iodixanol, iodoalphionic acid, iodochlorhydroxyquin, iodoform, iodopyracet, iodopyrrole, iodoquinol, iodosubgallate, iofetamine 1231, ioglycamic acid, iohexol, iomeglamic acid, iomeprol, iopamidol, iopanoic acid, iopentol, iophendylate, iophenoxic acid, iopromide, iopronic acid, iopydol, iopydone, iothalamic acid, iotrolan, ioversol, ioxaglic acid, ioxilan, IP-751, ipidacrine, IPL-576092, ipodate, iponiazid, ipratpopium, ipratropium, ipratropium bromide, iprazochrome, ipriflavone, iprindole, iproclozid, ipsapiron, irbesartan, IRFI-042, IRFI-165, iridomyrmecin, irindalone, irinotecan, irofulven, iron sorbitex, irsogladine, IS-741, isaglitazone, ISAtx-247, isbogrel, isepamicin, isoaminile, isobutyl p-aminobenzoate, isoconazole, isoetharine, isofloxythepin, isoflurane, isoflurophate, isoladol, isomethadone, isometheptene, isoniazid, isonixin, isopromethazine, isopropamide iodide, isopropyl alcohol, isopropyl unoprostone, isoproterenol, isosorbide, isosorbide dinitrate, isosorbide mononitrate, isothipendyl, isotretinoin, isovaleryl, isoxepac, isoxicam, isoxsuprine, isradipine, israpafant, ISV-403, itasetron, ITF-282, itopride, itraconazole, itramin, itriglumide, iturelix, ivabradine, ixabepilone, J-104132, J-107088, J-113397, Janex-1, josamycin, JTV-519, K-777, kainic acid, kalimate, kallidin, KB-130015, KCB-328, kebuzone, ketamine, ketanserin, ketazolam, kethoxal, ketobemidone, ketoconazole, ketoprofen, ketorolac, ketorolac, ketotifen, khellin, kinetin, KNI-272, KP-103, KP-157, KP-544, KRN-5500, KT-136, KUL-7211, KW-2170, KW-6002, KW-7158, L-365260, L-5-hydroxy-tryptophan, L-745337, L-758298, L-826141, labetalol, lacidipine, lactic acid, lactitol, lactulose, lafutidine, lamifiban, lamivudine, lamotrigine, landiolol, lanicemine, laniquidar, lanoconazole, lanoteplase, lanreotide, lansoprazole, lanthanum carbonate, lapatinib, laquinimod, lasofoxifene, latamoxef, latanoprost, lauroguadine, laurolinium acetate, lawsone, LAX-111, lazabemide, LB-30057, L-cysteine, lefetamine, leflunomide, leflunomide, leiopyrrole, lenampicillin, lentinan, lepirudin, lercanidipine, lerisetron, lesopitron, leteprinim, letosteine, letrozole, leucocyanidin, leuprolide, leuprolide acetate, leuprorelin, levallorphan, levaminsole, levcromakalim, levetiracetam, levobetaxolol, levobunolol, levobupivacaine, levocabastine, levocetirizine, levodopa, levodropropizine, levofloxacin, levomethadyl acetate, levomoprolol, levonorgestrel, levophacetoperane, levopropoxyphene, levorphanol, levosimendan, levosulpride, levothyroxine, levovirin, lexidronam, lexipafant, LF-15-0195, LF-16-0687, LGD-1550, LH, LH-RH, liarozote, licofelone, licostinel, lidadronate, lidamidine, lidocaine, lidofenin, lidoflazine, limaprost, lincomycin, lindan, linezolid, linoleic acid, linolenic acid, liothyronine, lipase, lipo-dexamethasone, lipo-flurbiprofen, Lipogel HA, LiquiVent, liranaftate, lisinopril, lisofyllin, lisuride, lithium, lithium citrate, lixivaptan, LJP-1082, LLUAlpha, LMP-160, LMP-420, loanzapine, lobaplatin, lobeline, lobenzarit, lodoxamide, lofentanil, lofepramine, lofexidine, loflucarban, lomefloxacin, lomerizine, lomifylline, lomustine, lonafarnib, lonapalene, lonazolac, lonidamine, loperamide, loperamide oxide, loprazolam, loprinone, loracarbef, lorajmine, loratadine, lorazepam, lorcainide, lormetazepam, lornoxicam, losartan, loteprednol, lotrafiban, lovastatin, loxapine, loxiglumide, loxoprofen, Lu-35-138, lubeluzole, lubiprostone, lucanthone, lucanthone, lumefantrine, lumiracoxib, lurtotecan, lutetium texaphyrin, LV-216, LX-104, LY-156735, LY-293111, LY-293558, LY-355703, lyapolate, lymecycline, lynestrenol, lypressin, lysine acetylsalicylate, lysine salicylate, lysophospholipids, M-40403, mabuprofen, mabuterol, macrophage colony-stimulating factor, MADU, mafenide, mafosfamide, magaldrate, magenta I, magnesium, magnesium carbonate, magnesium chloride, magnesium citrate, magnesium gluconate, magnesium lactate, magnesium salicylate, malathion, malotilate, mandelic acid, mandelic acid isoamyl, mangafodipir, manidipine, mannomustine, mannose-6-phosphate, maprotilline, maribavir, marimastat, maxacalcitol, mazindol, mazipredone, MC-5723, MCC-478, MCI-154, m-cresyl acetate, MDAM, MDI-101, MDI-403, MDL-100907, mebendazole, mebeverine, mebhydroline, mebrofenin, mebutamate, mecamylamine, mechlorethamine, mechlorethamine oxide, mecillinam, meclizine, meclocycline, meclofenamate, meclofenamic acid, meclofenoxate, mecloqualone, mecysteine, medazepam, medifoxamine, medrogestone, medronic acid, medroxyprogesterone, medrysone, mefenamic acid, mefenorex, mefexamide, mefloquine, mefruside, megestrol, meglumin, meglutol, melagatran, melanocortin-4 agonist, melarsoprol, melengestrol, melevodopa, melinamide, melitracen, meloxicam, melperone, melphalan, meluadrine, memantine, MEN-10700, MEN-10755, menadiol, menadione, menadoxime, menbutone, menogaril, MENT, menthol, menthyl valerate, meobentine, meparfynol, mepartricin, mepazine, mepenzolate bromide, meperidine, mephenesin, mephenoxalone, mephentermine, mephenytoin, mephobarbital, mepindolol, mepitiostane, mepivacaine, mepixanox, meprednisone, meprobamate, meproscillarin, meptazinol, mequitazine, meralein, meralluride, merbromin, mercaptomerin, mercumallylic acid, mercuric oleate, mercuric oxycyanide, merimepodib, meropenem, mersalyl, mertiatide, mesalamine, mesalazine, mesna, mesoridazine, mestanolone, mesterolone, mestranol, mesulfen, metaclazepam, metampicillin, metapramine, metaproterenol, metaraminol, metazocine, metergoline, metformin, methacholine, methacycline, methadone, methafurylene, methamphetamine, methandriol, methandrostenolone, methantheline, methapyrilene, methaqualone, metharbital, methazolamide, methdilazine, methenamine, methenolone, methestrol, methetoin, methicillin, methimazole, methiodal, methionic acid, methionine, methisazone, methitural, methixene, methocarbamol, methohexital, methotrexate, methotrimeprazine, methoxamine, methoxsalen, methoxycinnamate, methoxyflurane, methoxyphenamine, methoxypromazine, methscopolamine, methsuximide, methyclothiazide, methyl blue, methyl nicotinate, methyl propyl ether, methyl salicylate, methyl tert-butyl ether, methylbenzethonium chloride, methylbromide, methylcobalamin, methyldopa, methylene blue, methylergonovine, methylhexaneamide, methylphenidate, methylprednisolone, methylprednisolone, methylprednisolone, methylthiouracil, methyltrienolone, methyprylon, methysergide, metiazinic acid, metipranolol, metoclopramide, metocurine iodide, metofenazate, metolazone, metopimazine, metopon, metoprolol, metralindole, metrizamide, metrizoic acid, metron s, metyrapone, metyrosine, mexazolam, mexenone, mexiletine, mezlocillin, MFH-244, mianserin, mibefradil, miboplatin, micafungin, miconazole, micronomicin, midaxifyline, midazolam, midecamycin, midecamycin acetate, midesteine, midodrine, midostaurin, mifepristone, miglitol, miglustat, mildronate, milnacipran, miloxacin, milrinone, miltefosine, minaprine, minocycline, minodronic acid, minoxidil, miokamycin, mirtazapine, misoprostol, mitemcinal, mitiglinide, mitobronitol, mitoguazone, mitolactol, mitomycin, mitotane, mitoxantrone, mitoxantrone, MIV-210, mivacurium, mivazerol, mizolastine, mizoribine, MKC-733, MLN-519, MLN-576, moclobemide, modafinil, moexipril, mofarotene, mofebutazone, mofegiline, mofetil, mofezolac, MOL-6131, molindone, molsidomine, mometasone, monatepil, monobenzone, monoethanolamine, monolaurin, monoterpene diols, montelukast, monteplase, moperone, mopidamol, moprolol, moracizine, morazone, moricizine, moroxydine, morphazinamide, morphine, morphine-6-glucuronide, mosapramine, mosapride, motexafin, motretinide, moveltipril, moxalactam, moxastine, moxaverine, moxestrol, moxifloxacin, moxisylyte, moxonidine, M-PGA, MPI-5010, MPI-5020, MPL, MRS-1754, MS-209, MS-275, MS-325, MS-377, mupirocin, muscarin, muzolimine, MX-1013, mycophenolate, mycophenolic acid, myrophine, N-(hydroxymethyl)-nicotinamide, N,N,N',N'-tetraethylphthalamide, N-[4-[4-(2-methoxyphenyl)-1-piperazinyl]butyl]naphthalene-2-carboxamide, N2-formylsulfisomidine, N4-sulfanilylsulfanilamide, N4-O-D-glucosylsulfanilamide, nabilone, nabumetone, N-acetylcysteine, N-acetylmethionine, nadifloxacin, nadolol, nadoxolol, nafamostat, nafarelin, nafcillin, nafronyl, naftidofuryl, naftifine, naftopidil, nalbuphine, nalidixic acid, nalmefene, nalorphine, naloxone, naltrexone, NAMI, naminidil, nandrolone, napadisilate, naphazoline, naphthalene, naproxen, naproxen betainate, naratriptan, narceine, narcobarbital, natamycin, nateglinide, N-butyldeoxy-nojirimycin, N-butylscopolammonium Bromide, NC-503, NC-531, NCX-1000, NCX-4016, NCX-456, NCX-950, n-docosanol, NE-100, nealbarbital, nebivolol, nebostinel, nebracetam, nedaplatin, nedocromil, nefazodone, nefiracetam, nefopam, negamycin, nelfinavir, nemonapride, neostigmine, nepadutant, neramexane, neridronic acid, neriifolin, N-ethylamphetamine, neticonazole, netilmicin, nevirapine, NGD-98-2, nialamide, niaprazine, nicametate, nicaraven, nicardipine, nicergoline, niceritrol, niclosamide, nicoclonate, nicofuranose, nicomol, nicomorphine, nicorandil, nicotinamide, nicotine, nicotinic acid, nicotinic acid benzyl ester, nicotinyl alcohol, nifedipine, nifekalant, nifenalol, niflumic acid, nifuratel, nifurfoline, nifuroxazide, nifuroxime, nifurpirinol, nifurprazine, nifurtimox, nifurtoinol, nifurzide, NIK-254, nikethamide, nilutamide, nilvadipine, nimesulide, nimetazepam, nimodipine, nimorazole, nimustine, ninopterin, NIP-142, NIP-531, niperotidine, nipradilol, niridazole, nisoldipine, nitazoxanide, nitisinone, nitracrine, nitrazepam, nitrendipine, nitroflurbiprofen, nitrofurantoin, nitrofurazone, nitroglycerin, nitromersol, nitronaproxen, nitroxazepine, nitroxoline, nizatidine, nizofenone, NM-3, NM-702, N-methylephedrine, N-methylepinephrine, N-methylglucamine, NN-414, NNC-05-1869, nobel, nogalamycin, nolatrexed, nolomirole, nolpitantium, nomegestrol, nomifensine, noprylsulfamide, norbolethone, nordazepam, nordefrin, nordihydroguaiaretic acid, norelgestromin, norepinephrine, norethandrolone, norethindrone, norethynodrel, norfenefrine, norfloxacin, norgesterone, norgestimate, norgestrel, norgestrienone, norlevorphanol, normethadone, normethandrone, normorphine, norphenazone, norpipanone, norpseudoephedrine, nortriptyline, norvinisterone, noscapine, novembichin, novobiocin, noxiptillin, noxythiolin, NS-1209, NS-1231, NS-126, NS-220, NS-2330, NS5A inhibitors, NS-7, NS-8, NSC-330507, NSC-619534, NSC-697726, N-sulfanilyl-3,4-xylamide, NU-6027 nucleosides, NV-07, NVP-SRA880, NW-1029, NXY-059, Nylidrin, NZ-314, NZ-419, obidoxime chloride, OC-108, ocinaplon, octabenzone, octacaine, octamoxin, octaverine, octenidine, octodrine, octopamine, octotiamine, octreotide, octyl, ofloxacin, oleandrin, oleic acid, olmesartan-medoxomil, o-lodohippurate, olopatadine, olpadronic acid, olsalazine, oltipraz, OM-294DP, omacor, omapatrilat, omeprazole, omiloxetine, omoconazole, onapristone, ondansetron, ONO-3403, ONO-4128, ONO-8815 Ly, ONT-093, OPC-14523, OPC-31260, OPC-51803, OPC-6535, opiniazide, opioid analgesics, opipramol, orazamide, orazipone, Org-12962, Org-24448, oritavancin, orlistat, ormeloxifene, ornidazole, ornipressin, ornithine, ornoprostil, orotic acid, orphenadrine, orthocaine, osalmid, osanetant, osaterone, oseltamivir, OSI-7836, OSI-7904, ospemifene, otilonium bromide, ouabain, oxaceprol, oxacillin, oxaflozane, oxaliplatin, oxalyt-C, oxamarin, oxametacine, oxamniquine, oxandrolone, oxantel, oxapropanium, oxaprozin, oxatomide, oxazepam, oxazolam, oxcarbazepine, oxeladin, oxendolone, oxethazaine, oxetoron, oxiconazole, oxidronic acid, oxiniacic acid, oxiracetam, oxitropium, oxolamin, oxolinix acid, oxophenarsine, oxprenolol, oxybenzone, oxybutynin, oxycinchophen, oxycodone, oxygent, oxymesterone, oxymetazoline, oxymetholone, oxymethurea, oxymorphone, oxypendyl, oxypertine, oxyphenbutazone, oxyphencyclimine, oxyphenisatin, oxyphenonium, oxypinocamphone, oxypurinol, oxytedrine, oxytetracycline, ozagrel, p-(benzylsulfonamido)-benzoic acid, P-100, P-1202, P32/98, PA-824, PACAP 38, pactitaxel, PADRE, pagoclone, PAI inhibs, palindore, palivizumab, palonosetron, pamabrom, pamaquine, pamicogral, pamidronate, p-aminobenzoic acid, p-aminohippuric acid, p-amino-propiophenone, p-aminosalicylic acid, panavir, pancuronium, panipenem, pantethine, pantoprazole, pantothenic acid, papain, papaverine, paracetamol, paraflutizide, paraldehyde, paramethadione, paramethasone, paranyline, parathyroid hormone, parecoxib, parethoxycaine, pargyline, paricalcitol, paromomycin, paroxetine, paroxypropione, parsalmide, patrin-2, pazinaclone, pazufloxacin, p-bromoacetanilide, PC-NSAIDs, PD-0166285, pecilocin, pefloxacin, pegvisomant, pelletierine, pemetrexed, pemirolast, pemoline, pempidine, PEN-203, penamecillin, penbutolol, penciclovir, penethamate, penfluridol, penicillamine, penicillin G, penicillin G Procaine, penicillin N, penicillin O, penicillin V, penimepicycline, penntuss, pentaerythritol, pentaerythritol, pentaerythritol chloral, pentagastrin, pentagestrone, pentalyte, pentam thonium, pentamidine, pentazocine, pentetate, pentetic acid, pentetreotide, penthienate, pentifyllin, pentigetide, pentisomide, pentobarbital, pentolinium, pentorex, pentosan, pentostatin, pentoxifylline, pentoxyl, pentrinitrol, pentylenetetrazole, peplomycin, peptide, peptide, perazine, perfiromycin, perflubron, perfosfamide, pergolide, perhexiline, pericyazine, perifosine, perillyl alcohol, perimethazine, perindopril, periodyl, perisoxal, perlapine, permanganate, permethrin, perospirone, perphenazine, petroleum benzin, PH-10, phanquinone, pharmacor, pharmaprojects no. 6362, pharmaprojects no. 4994, pharmaprojects no. 5325, pharmaprojects no. 5972, pharmaprojects no. 6446, pharmaprojects no. 6590, pharmaprojects no. 6656, pharmaprojects no. 6691, pharmaprojects no. 6743, pharmaprojects no. 6748, phenacaine, phenacemide, phenacetin, phenadoxone, phenallymal, phenamet, phenamide, phenazocine, phenazopyridine, phenbutamide, phencyclidine, phendimetrazine, phenelzine, phenesterine, phenetharbital, phenethicillin, pheneturide, phenformin, phenglutarimide, phenindamine, phenindione, pheniprazine, pheniramine, phenmetrazine, phenobarbital, phenobutiodil, phenocoll, phenoctide, phenolphthalein, phenolphthalol, phenolsulfonphthalein, phenol-tetrachlorophthalein, phenoperidine, phenosulfazole, phenoxybenzamine, phenoxypropazine, phenprobamate, phenprocoumon, phenserine, phensuximide, phentermine, phentetiothalein, phentolamine, phenyl acetylsalicylate, phenyl aminosalicylate, phenyl salicylate, phenylbutazone, phenylephrine, phenylethanolamine, phenylmercury, phenylmethylbarbituric acid, phenylpropanolamine, phenylpropyl-methylamine, phenyltoloxamine, phenyramidol, phenytoin, phethenylate, phloroglucinol, pholcodine, pholedrine, phoramide, phosphate, phosphate, phosphocreatine, phoscysteamine, phosphorylcholine, phthalylsulfathiazole, phthalysulfacetamide, p-hydroxyephedrine, phylloquinone, physostigmine, phytic acid, PI-88, piberaline, piboserod, picilorex, picloxydine, picoperine, picosulfate, picotamide, picumast, pidotimod, pifarnine, piketoprofen, pildralazine, pilocarpine, piloplex, pilsicainide, pimeclone, pimecrolimus, pimefylline, pimilprost, piminodine, pimobendan, pimozide, pinacidil, pinaverium, pinazepam, pindolol, pioglitazone, pipacycline, pipamazine, pipamperone, pipazethate, pipebuzone, pipecurium, pipecuronium, pipemidic acid, pipenzolate bromide, piperacetazine, piperacillin, piperazine adipate, piperidione, piperidolate, piperilate, piperine analogues, piperocaine, piperonal, piperoxan, piperylone, pipobroman, piposulfan, pipotiazine, pipoxolan, pipradrol, piprozolin, piracetam, pirarubicin, pirazolac, pirbuterol, pirenoxine, pirenzepine, piretanide, pirfenidone, piribedil, piridocaine, pirifibrate, piritramide, piritrexim, pirlindole, pirmenol, piroctone, piroheptine, piromidic acid, piroxicam, piroxicam betadex, piroxicam cinnamate, pirozadil, pirprofen, pitavastatin, pivagabine, pivaloyloxymethyl, pivalylbenzhydrazine, pivampicillin, pivampicillin/pivmecillinam, pivcefalexin, pivmecillinam, pixantrone, pizotifen, pizotyline, PKI-166, p-lactophenetide, plafibride, plasminogen activator, plasmocid, platonin, plaunotol, PLD-118, PLD-147, pleconaril, plicamycin, p-methyldiphenhydramine, PMS-601, Pneumococcal, PNU-288034, podophyllotoxin, polaprezinc, poldine methylsulfate, policresulen, polidexide, polidocanol, poliovirus vaccine, poly-ADPRT inhibitors, polyestradiol, polyphenon E, polythiazide, porfimer, posaconazole, posatirelin, potassium, potassium, potassium, potassium chloride, potassium gluconate, potassium p-aminobenzoate, povidone, povidone-iodine, PP-117, PR-2699, PR-608, practolol, prajmaline, pralidoxime, pralnacasan, pramipexole, pramiracetam, pramiverin, pramlintide, pramoxine, pranidipine, pranlukast, pranoprofen, prasterone, pratosartan, pravastatin, prazepam, praziquantel, prazosin, prednicarbate, prednimustine, prednisolone, prednisolone 21-diethylaminoacetate, prednisolone farnesil, prednisolone sodium, prednisone, prednival, prednylidene, pregabalin, pregnan-3α-o-20-one, premarin+trimegestone, prenalterol, prenoxdiazine, prenylamine, prezatide, pridinol, prifinium, prilocaine, primaquine, primidone, prinomastat, PRO-2000, probenecid, probucol, procainamide, procaine, procarbazine, procaterol, prochlorperazine, procodazol, procyclidine, procymate, prodipine, proflavine, progabide, progesterone, proglumetacin, proglumide, proheptazine, prolactin, prolintane, prolonium, promazine, promedol, promegestone, promestriene, promethazine, pronethalol, propacetamol, propafenone, propagermanium, propallylonal, propamidine, propane-1,2-diol, propanidid, propantheline, proparacaine, propatyl, propenidazole, propentofylline, propicillin, propiomazine, propionic acid, propionyl 1-carnitine, propipocaine, propiram, propiverine, propizepine, propofol, propoxycaine, propoxyphene, propranolol, propylhexedrine, propyliodone, propylthiouracil, propyphenazone, proquazone, proscillaridin, prostacyclin, prostaglandin E1, prostaglandin E2, prostaglandin F2a, prosultiamine, protein C, protheobromine, prothipendyl, protiofate, protionamide, protizinic acid, protoanemonin, protoklol, protoporphyrin IX, protriptyline, pro-urokinase, proxazole, proxetil, proxibarbal, proxigermanium, proxyphylline, prozapine, prucalopride, prulifloxacin, pseudococaine, pseudoephedrine, pseudoephedrine, pseudoephedrine+triprolidine, psilocybin, PSK-3841, p-sulfanilyl-benzylamine, PT-141, pteropterin, puromycin, PX-12, pyrantel, pyrazinamide, pyridinol carbamate, pyridostigmine, pyridoxal 5-phosphate, pyridoxine, pyrilamine, pyrimethamine, pyrinoline, pyrisuccideanol, pyrithione, pyrithyldione, pyritinol, pyrocatechol, pyrogallol, pyronaridine, pyrophosphate, pyrovalerone, pyroxylin, pyrrobutamine, pyrrocaine, pyrrolntrin, pyrvinium pamoate, quazepam, quercetin, quetiapine, quinacillin, quinacrine, quinagolide, quinapril, quinaprilat, quinapyramine, quinbolone, quinestradiol, quinestrol, quinethazone, quinfamide, quinidine, quinine, quinocide, quinupramine, quinupristin, R-107500, R-667, rabeprazole, racecadotril, racemethorphan, raloxifene, raltitrexed, ramatroban, ramifenazone, ramipril, ramosetron, Ramot project No. 1097, ranimustine, ranitidine, ranitidine bismuth, ranolazine, ranpirnase, rapacuronium, rasagiline, raubasine, ravuconazole, raxofelast, razoxane, RC-529, rebamipide, rebimastat, reboxetime, remacemide, remifentanil, reminetant, remoxipride, renzapride, repaglinide, repertaxin L-lysine salt, repinotan, repirinast, reposal, reproterol, rescimetol, rescinnamine, reserpiline, reserpine, resibufogenin, resiquimod, resorcinol, reteplase, retigabine, retinoic acid, revimid, R-flurbiprofen, rho (D) immune, rho-kinase inhibitors, ribavirin, riboflavin, ribostamycin, ricinoleic acid, ridogrel, rifabutin, rifalazil, rifametane, rifamide, rifampicin+trimethoprim, rifampin, rifamycin SV, rifapentine, rifaximin, rifaximine cream, rilmazafone, rilmenidine, riluzole, rimantadine, rimazolium, rimexolone, rimiterol, rimonabant, riodoxol, rioprostil, risedronate, risedronic acid, risperidone, ritanserin, ritipenem, ritodrine, ritonavir, rituximab, rivastigmine, rizatriptan, RJR-2403, RNA Stealth, Ro-0094889, Ro-61-1790, rociverine, rocuronium, rofecoxib, roflumilast, rokitamycin, rolipram, rolitetracycline, romurtide, ronifibrate, ropinirole, ropivacaine, roquinimex, rosaprostol, rosaramicin, rose bengal, rosiglitazone, rosoxacin, rostaporfin, rosuvastatin, rotigotine, rotraxate, roxarsone, roxatidine, roxifiban, roxindol, roxithromycin, RPR-109881A, RPR-130401, R-roscovitine, RS-0406, RSR-13, rubijervine, rubitecan, ruboxistaurin, rufinamide, rufloxacin, rupatadine, rutin, RWJ-54428, S-0139, S-15535, S-18886, S-34730, S-3578, S-36496, S-36527, S-5751, S-8510, S-8921, sabcomeline, sabeluzole, S-adenosylmethionine, safinamide, salacetamide, salazosulfadimidine, salbutamol, salicin, salicyl alcohol, salicylamide, salicylamide O-acetic acid, salicylanilide, salicylic acid, salicylsilfuric acid, salinazid, salmeterol, salsalate, salverine, samarium $^{153}$Sm, sampatrilat, sancycline, saperconazole, sapropterin, saquinavir, saralasin, saredutant, saredutant, sarizotan, sarizotan, sarpogrelate, sarpogrelate, satigrel, satigrel, satraplatin, satraplatin, satumomab, satumomab, SB-237376, SB-237376, SB-238039, SB-238039, SB-277011, SB-277011, scarlet red, SCH-00013, SCH-00013, Sch-23863, Sch-23863, Sch-57790, Sch-63390, scillarenin, scopolamine, scopolamine, scopolamine N-oxide, SCS technology, secalciferol, secnidazole, secobarbital, selegiline, selenomethionine, sematilide, semotiadil, seocalcitol, sepimostat, seratrodast, sertaconazole, sertaconazole, sertindole, sertindole, sertraline, sertraline, sestamibi, setastine, setastine, sevelamer, sevelamer, sevoflurane, sevoflurane, SG-210, sibutramine, siccanin, sildenafil, silodosin, silprostone, silver lactate, silver picrate, silver sulfadiazine, simetride, simfibrate, simvastatin, sincalide, sintropium bromide, sisomicin, sitafloxacin, sitamaquine, sitaxsentan, sivelestat, SJA-6017, SL-65-1498, SLV-306, SLV-308, Sm153 lexidronam, S-methylmethionine, SMP-300, SN-38, SNAP-7941, SOA-132, soblidotin, sobrerol, sobuzoxane, sodium arsanilate, sodium arsphenamine, sodium chloride, sodium dibunate, sodium folate, sodium formaldehydesulfoxylate, sodium hyaluronate, sodium iodomethamate, sodium nitrite, sodium nitroprusside, sodium oxybate, sodium phenol-sulfonate, sodium phenylbutyrate, sodium phosphate, sodium prasterone sulfate, sodium propionate, sodium salicylate, sodium tetradecyl sulfate, sofalcone, solasulfone, solifenacin, sorbinicate, sorbitol, sorivudine, sotalol, soterenol, sozoiodolic acid, spaglumic acid, sparfloxacin, sparteine, SPA-S-843, spasmolytol, SPD-754, spectinomycin, SPI-339, spiperone, spirapril, spirogermanium, spironolactone, SR-121463, SR-144190, SR-146131, SR-271425, SR-27897, SR-31747, SR-58611, SS732, SS-750, SSR-149415, SSR-180575, SSR-181507, SSR-591813, SST-101, SSY-726, ST-200, stachyfilin, stallimycin, stampidine, stannous, stannsoporfin, stanolone, stanozolol, staph aureus ther, STAT4 inhibitors, stavudine, stenbolone, stepronim, stibocaptate, stibophen, stilbamidine, stiripentol, streptodornase, streptomycin, streptonicozid, streptonigrin, streptozocin, strontium ranelate, strontium-89 chloride, succimer, succinimide, succinylcholine, succinylcholine, succinylsulfathiazole, succisulfone, suclofenide, sucralfate, sufentanil, sulbactam, sulbactam+ampicillin, sulbenicillin, sulbentine, sulbutiamine, sulconazole, suleptanate, sulesomab, sulfabenzamide, sulfacetamide, sulfachlorpyridazine, sulfachrysoidine, sulfacytine, sulfadiazine, sulfadicramide, sulfadimethoxine, sulfadoxine, sulfaethidole, sulfaguanidine, sulfaguanole, sulfalene, sulfaloxic acid, sulfamerazine, sulfameter, sulfamethazine, sulfamethizole, sulfamethomidine, sulfamethoxazole, sulfamethoxypyrazine, sulfamethoxypyridazine, sulfametrole, sulfamidochrysoidine, sulfamoxole, sulfanilamide, sulfanilic acid, sulfanilylurea, sulfaperine, sulfaphenazole, sulfaproxyline, sulfapyrazine, sulfapyridine, sulfarside, sulfarsphenamine, sulfasalazine, sulfasomizole, sulfasymazine, sulfathiazole, sulfathiourea, sulfinalol, sulfinpyrazone, sulfiram, sulfisomidine, sulfisoxazole, sulfobromophthalein, sulfonethylmethane, sulfoniazide, sulfonic acid, sulfonmethane, sulforidazine, sulfoxone, sulindac, sulisatin, sulisobenzone, sulmarin, sulmazole, suloctidil, sulphan blue, sulpiride, sultamicillin, sulthiame, sultopride, sultosilic acid, sumanirole, sumatriptan, SUN-N8075, suplatast, suprofen, suramin, surfactant TA, suriclone, suxibuzone, SYM-1010, SYM-2081, SYM-2207, symclosene, Syn-1253, Syn-2190, Syn-2869, synephrine, syrosingopine, T-1095, T-1249, T-3912, T-588, T-67, T-82, TA-2005, TA-2005, TA-993, tabimorelin, tacalcitol, tacedinaline, tacrine, tacrolimus, tadalafil, tafenoquine, tafluposide, TAK-375, TAK-427, TAK-559, taka-diastase, talampanel, talampicillin, talaporfin, talastine, talbutal, talinolol, talipexole, talnetant, talniflumate, taltirelin, tamoxifen, tamsulosin, tandospirone, tannoform, taprostene, tariquidar, TAS-103, tasosartan, taurocholic acid, taurolidine, tazanolast, tazarotene, tazobactam, tazobactam+piperacillin, TBC-3711, TCH-346, tebipenem, teboroxime, tecadenoson, tecastemizole, Technetium $^{99}$Tc, teclothiazide, teclozan, tedisamil, teflurane, tegafur, tegafur+uracil, tegaserod, teicoplanin, telbivudine, telenzepine, telithromycin, telmesteine, telmisartan, telomerase inhibs, temazepam, temiverine, temocapril, temocillin, temoporfin, temozolomide, tenatoprazole, tenecteplase, tenidap, teniposide, tenofovir, tenofovir disoproxil, tenonitrozole, tenoxicam, tenuazonic acid, teprenone, terazosin, terbinafine, terbutaline, terconazole, terfenadine, terguride, terlipressin, terodiline, terofenamate, terpin, tertalolol, tert-pentyl alcohol, tesaglitazar, tesmilifene, testolactone, testosterone, tetrabamate, tetrabarbital, tetrabenazine, tetracaine, tetrachloroethylene, tetracine, tetracycline, tetrahydrozoline, tetrandrine, tetrantoin, tetrazepam, tetrofosmin, tetroxoprim, Tevenel®, tezacitabine, tezosentan, thalidomide, thenaldine, thenyldiamine, theobromine, theofibrate, theophylline, thiabendazole, thiacetazone, thiacymserine, thialbarbital, thiamine, thiamiprine, thiamphenicol, thiamylal, thiazesim, thiazinamium, thiazolinobutazone, thiazolsulfone, thibenzazoline, thiemalat, thiethylperazine, thimerfonate, thimerosal, thiobarbital, thiobutabarbital, thiocarbamizine, thiocarbarsone, thiocolchicine, thiocresol, thioctic acid, thioglycerol, thioguanine, thioimrag, thiopental, thiophosphoramide, thiopropazate, thioproperazine, thioridazine, thiosulfate, thiothixene, thiovir, thiphenamil, thiram, thonzylamine, thozalinone, thromboplastin, thurfyl nicotinate, thymectacin, thymol, thymopentin, thymyl N-isoamylcarbamate, thyropropic acid, thyroxine, tiadenol, tiagabine, tiamenidine, tianeptine, tiapride, tiaprofenic acid, tiaramide, tiazofurin, tibezonium, tibolone, ticarcillin, ticlopidine, ticrynafen, tiemonium, tigecycline, tigemonam, tigloidine, tilidine, tilisolol, tilmacoxib, tiludronic acid, timentin, timepidium, timiperone, timolol, timonacic, tin ethyl etiopurpurin, tinazoline, tinidazole, tinoridine, tiocarlide, tioclomarol, tioconazole, tiopronin, tiotropium, tioxolone, tipepidine, tipifarnib, tipranavir, tiquizium, tirapazamine, tiratricol, tirilazad, tirofiban, tiropramide, titanium sulfate, tiuxetan, tixocortol, tizanidine, TLK-199, TLK-286, TNF-β analogue, TNP-470, TO-186, tobramycin, tocainide, tocamphyl, tocladesine, tocoretinate, todralazine, tofenacin, tofimilast, tofisopam, tolazamid, tolazolin, tolbutamide, tolcapone, tolciclate, tolcyclamide, tolevamer, tolfenamic acid, tolindate, toliprolol, tolmetin, tolnaftate, tolonidine, tolonium, toloxatone, tolperisone, tolpropamine, tolrestat, tolserine, tolterodine, tolvaptan, tolycaine, topiramate, topoisomerase, topotecan, torasemide, torcetapib, torcitabine, toremifene, torsemide, tositumomab, tosulfloxacin, tramadol, tramazoline, trandolapril, tranexamic acid, tranilast, trans-retinoic acid, tranylcypromine, trapidil, trastuzumab, travoprost, traxanox, traxoprodil, trazodone, tremacamra, trenbolone, trengestone, treosulfan, trepibutone, treprostinol, tretinoin, tretoquinol, TRH, TRI-50b, triacetin, triamcinolone, triamcinolone, triamcinolone, triamcinolone acetonide, triamterene, triapine, triaziquone, triazolam, tribenoside, tribromophenate, trichlorfon, trichlormethiazide, trichlormethine, trichloroethylene, triclobisonium, triclocarban, triclofenol piperazine, triclofos, triclosan, tricromyl, tridihexethyl iodide, trientine, triethanolamine, triethylenemelamine, trifluoperazine, trifluperidol, triflupromazine, trifluridine, triflusal, triflutate, trihexyphenidyl, trimazosin, trimebutine, trimecaine, trimeprazine, trimetazidine, trimethadione, trimethaphan, trimethobenzamide, trimethoprim, trimetozine, trimetrexate, trimipramine, trimoprostil, triolstane, trioxsalen, tripamide, triparanol, tripelennamine, triprolidine, triptorelin, tritiozine, tritoqualine, TRK-530, TRK-820, troclosene, trofosfamide, troglitazone, troleandomycin, trolnitrate, tromantadine, trometamol, trometamol, tromethamine, tromethamine, tropacine, tropesin, tropicamide, tropine, tropisetron, trospectomycin, trospium, trovafloxacin, troxacitabine, troxerutin, troxipide, trypan red, tryparsamide, tryptophan, TSH, TSN-09, TU-2100, tuaminoheptane, tubercidin, tubocurarine chloride, tulobuterol, TV-3326, TY-11223, TY-12533, TYB-3215, tybamate, tyloxapol, tymazoline, tyramine, tyropanoate, ubenimex, ufenamate, undecylenic acid, unoprostone, UR-8880, uracil mustard, uralyt-U, urapidil, urea, uredepa, urethan, uridine 5'-triphosphate, urinastatin, ursodeoxycholic acid, ursodiol, ushercell, uzarin, vaccine, Diphtheria Vaccine, Polyvalent Vaccine, valacyclovir, valdecoxib, valdetamide, valethamate, valganciclovir, valnoctamide, valomaciclovir, valproate, valproic acid, valpromide, valrocemide, valrubicin, valsartan, valspodar, vardenafil, varespladib, varicella virus, vatanidipine, VEA, vecuronium, velnacrine, venlafaxine, veralipride, verapamil, verteporfin, vesnarinone, vetrabutine, VF-233, VI-0134, vidarabine, vigabatrin, vilazodone, viloxazine, viminol, vinbarbital, vinblastine, vinburnine, vincamine, vinconate, vincristine, vindesine, vinflunine, vinorelbine, vinpocetine, vinyl ether, vinylbital, viquidil, viridin, visnadine, vitamin A, vitamin B12, vitamin C, vitamin D2, vitamin D3, vitamin K5, prenatal vitamins, VLA-4 antagonists, VNP-4010M, voglibose, voriconazole, vorozole, VUF-K-8788, warfarin, WF-10, WMC-79, wound healing matrix, WP-170, xaliproden, xamoterol, xanomeline, xanthinol niacinate, xemilofiban, xenbucin, xibenolol, xibornol, ximelagatran, ximoprofen, xipamide, xorphanol, XR-5118, XR-5944, xylometazoline, xylose, YH-1885, YM-511, YM-598, yohimbine, YT-146, Z-321, Z-335, zafirlukast, zalcitabine, zaldaride, zaleplon, zaltoprofen, zanamivir, zanapezil, zatebradine, ZD-0473, ZD-0947, ZD-6126, ZD-9331, zebularine, zelandopam, zenarestat, ziconotide, zidovudine, zileuton, zimeldine, zinc acetate, zinc acexamate, zinc ibuprofenate, zinc p-phenolsulfonate, zinc salicylate, zinostatin, zinostatin stimalamer, zipeprol, ziprasidone, zofenopril, zofenpril+HCTZ, zoledronic acid, zolimidine, zolmitriptan, zolpidem, zomepirac, zonampanel, zoniporide, zonisamide, zopiclone, zopolrestat, zorubicin, zosuquidar, zotepine, ZP-123, Z-tamoxifen, zuclopenthixol, α1-antitrypsin, α-bisabolol, α-chloralose, α-ethylbenzyl alcohol, α-glucose-1-phosphate, α-phenylbutyramide, α-santonin, α-terpineol, α-tocopherol, β-alethine, β-benzalbutyramide, β-carotene, β-eucaine, β-propiolactone, β-sitosterol, γ-aminobutyric acid, γ-hydroxybutyrate, γ-linolenic acid, δ-aminolevulinic acid, ε-acetamidocaproic, and ε-aminocaproic acid. See also U.S. Pat. No. 7,927,613, which is incorporated herein by reference in its entirety. Other pharmaceutically acceptable coformers include those delineated in the "Generally Regarded as Safe" ("GRAS") and/or the US FDA "Everything Added to Food in the United States" ("EAFUS") lists.

In some of these embodiments, at least one of the one or more pharmaceutically acceptable coformers can be a compound having any one of formulas (I), (XVIII)-(XXV), and XXVII, (e.g., formula XXIV or XXV) as described in U.S. Pat. No. 10,292,951 which is incorporated herein by reference in its entirety; or any one of the compounds delineated above. In certain of these embodiments, at least one of the one or more pharmaceutically acceptable coformers can be a niclosamide analogue having any one of formulas (I), (XVIII)-(XXV), and XXVII (e.g., formula XXIV or XXV; or XXVI) as described in U.S. Pat. No. 10,292,951 which is incorporated herein by reference in its entirety; or any one of the compounds specifically delineated above.

In some embodiments, the coformer can be any one or more additional therapeutic agents as described herein.

Non-Limiting Combinations

In some embodiments, the cocrystal includes (i) niclosamide; and (ii) a pharmaceutically acceptable salt of niclosamide; or a pharmaceutically acceptable salt and/or hydrate of niclosamide of a niclosamide analog.

In some embodiments, the cocrystal includes (i) niclosamide; and (ii) a second API.

In some embodiments, the cocrystal includes (i) a pharmaceutically acceptable salt of niclosamide; and (ii) a second API.

In some embodiments, the cocrystal includes (i) niclosamide; and (ii) a second API.

In some embodiments, the cocrystal includes (i) a pharmaceutically acceptable salt of niclosamide; and (ii) an amino acid (e.g., proline, e.g., D-proline, or L-proline, or racemic proline).

In some embodiments, the cocrystal includes (i) niclosamide; and (ii) an amino acid (e.g., proline, e.g., D-proline, or L-proline, or racemic proline).

In some embodiments, the cocrystal includes (i) a pharmaceutically acceptable salt of niclosamide; and (ii) a 5-10 (e.g., 5-9, 5-6, or 5) membered heteroaryl, e.g., a nitrogen-containing heteroaryl, e.g., imidazole.

In some embodiments, the cocrystal includes (i) niclosamide; and (ii) a 5-10 (e.g., 5-9, 5-6, or 5) membered heteroaryl, e.g., a nitrogen-containing heteroaryl, e.g., imidazole.

For examples, see Sanphui, P. *Cryst. Growth Des.* 2012, 12, 4588; Imramovský, A. *Crystals* 2012, 2, 349-361; and Grifasi, F. *Cryst. Growth Des.* 2015, 15, 4588.

Niclosamide Compound of the Co-Crystal

In some embodiments, the chemical purity of the niclosamide compound can be as defined anywhere herein.

Particle Size of the Co-Crystal

In some embodiments, the co-crystal can have a reduced particle size as defined anywhere herein for the niclosamide compounds.

In some embodiments, co-crystals having reduced particle size can be prepared by jet milling, e.g., using CMTI equipment NGMP-Mill-A, a 2-inch, pancake micronizer manufactured by Sturtevant.

Particle Size Distribution (PSD) can be determined by laser diffraction technique, e.g., using a "MALVERN MASTERSIZER 2000" (standard range between 0.020 and 2000.0 microns), model "APA 2000", equipped with "Hydro 2000 sm" as dispersing unit.

In some embodiments, the co-crystal has a reduced particle size range.

In some embodiments, co-crystal has a particle size range of from about 0.1 μm to about 30 μm. In certain embodiments, the co-crystal has a particle size range of from about 0.1 μm to about 20 μm. In certain embodiments, the co-crystal has a particle size range of from about 0.1 μm to about 10 μm.

In some embodiments, the co-crystal has a particle size distribution D(0.9) of from about 1.0 μm to about 15.0 μm. In certain embodiments, the co-crystal has a particle size distribution D(0.9) of from about 1.0 μm to about 10.0 μm. In certain embodiments, the co-crystal has a particle size distribution D(0.9) of from about 6.0 μm to about 8.0 μm. In certain embodiments, the co-crystal has a particle size distribution D(0.9) of from about 2.2 μm to about 3.2 μm.

In some embodiments, the co-crystal has a particle size distribution D(0.1) of from about 0.1 μm to about 1.5 μm. In certain embodiments, the co-crystal has a particle size distribution D(0.1) of from about 0.1 μm to about 1.0 μm. In certain embodiments, the co-crystal has a particle size distribution D(0.1) of from about 0.3 μm to about 0.9 μm.

In some embodiments, the co-crystal has a particle size distribution D(0.5) of from about 0.5 μm to about 6.0 μm. In certain embodiments, the co-crystal has a particle size distribution D(0.5) of from about 1.0 μm to about 4.0 μm. In certain embodiments, the co-crystal has a particle size distribution D(0.5) of from about 1.0 μm to about 2.0 μm. In certain embodiments, the co-crystal has a particle size distribution D(0.5) of from about 2.5 μm to about 3.5 μm.

In some embodiments, the co-crystal has a particle size distribution D(0.9) of from about 1.0 μm to about 10.0 μm, a particle size distribution D(0.5) of from about 1.0 μm to about 4.0 μm, and a particle size distribution D(0.1) of from about 0.1 μm to about 1.0 μm.

In some embodiments, the co-crystal has a particle size distribution D(0.9) of from about 6.0 μm to about 8.0 μm, a particle size distribution D(0.5) of from about 1.0 μm to about 4.0 μm, and a particle size distribution D(0.1) of from about 0.3 μm to about 0.9 μm.

In some embodiments, the co-crystal has a particle size distribution D(0.9) of from about 2.2 μm to about 3.2 μm, a particle size distribution D(0.5) of from about 1.0 μm to about 4.0 μm, and a particle size distribution D(0.1) of from about 0.3 μm to about 0.9 μm.

In some embodiments, the niclosamide compound has a chemical purity of greater than about 99.0%; and the co-crystal has a particle size distribution D(0.9) of from about 1.0 μm to about 10.0 μm, a particle size distribution D(0.5) of from about 1.0 μm to about 4.0 μm, and a particle size distribution D(0.1) of from about 0.1 μm to about 1.0 μm.

In some embodiments, the niclosamide compound has a chemical purity of greater than about 99.0%; and the co-crystal has a particle size distribution D(0.9) of from about 6.0 μm to about 8.0 μm, a particle size distribution D(0.5) of from about 1.0 μm to about 4.0 μm, and a particle size distribution D(0.1) of from about 0.3 μm to about 0.9 μm.

In some embodiments, the niclosamide compound has a chemical purity of greater than about 99.0%; and the co-crystal has a particle size distribution D(0.9) of from about 2.2 μm to about 3.2 μm, a particle size distribution D(0.5) of from about 1.0 μm to about 4.0 μm, and a particle size distribution D(0.1) of from about 0.3 μm to about 0.9 μm.

In some embodiments, the niclosamide compound has a chemical purity of greater than about 99.0%; and the co-crystal has a particle size range of from about 0.1 μm to about 30 μm, a particle size distribution D(0.9) of from about 1.0 μm to about 10.0 μm, a particle size distribution D(0.5) of from about 1.0 μm to about 4.0 μm, and a particle size distribution D(0.1) of from about 0.1 μm to about 1.0 μm.

In some embodiments, the niclosamide compound has a chemical purity of greater than about 99.0%; and the co-crystal has a particle size range of from about 0.1 μm to about 30 μm, a particle size distribution D(0.9) of from about 6.0 μm to about 8.0 μm, a particle size distribution D(0.5) of from about 1.0 μm to about 4.0 μm, and a particle size distribution D(0.1) of from about 0.3 μm to about 0.9 μm.

In some embodiments, the niclosamide compound has a chemical purity of greater than about 99.0%; and the cocrystal has a particle size range of from about 0.1 μm to about 30 μm, a particle size distribution D(0.9) of from about 2.2 μm to about 3.2 μm, a particle size distribution D(0.5) of from about 1.0 μm to about 4.0 μm, and a particle size distribution D(0.1) of from about 0.3 μm to about 0.9 μm.

In certain of the foregoing embodiments, the co-crystal has a particle size distribution D(0.5) of from about 2.5 μm to about 3.5 μm.

In certain other of the foregoing embodiments, the co-crystal has a particle size distribution D(0.5) of from about 1.0 μm to about 2.0 μm.

Pharmaceutical Compositions and Administration

General

A niclosamide compound, or a pharmaceutically acceptable salt and/or cocrystal thereof; e.g., a compound, such as niclosamide, or a pharmaceutically acceptable salt and/or cocrystal thereof) is administered to a subject in need thereof by any route which makes the compound bioavailable (e.g., locally bioavailable). In certain embodiments, the route is respiratory administration.

In some embodiments, a niclosamide compound, or a pharmaceutically acceptable salt and/or cocrystal thereof, e.g., a compound, such as niclosamide, or a pharmaceutically acceptable salt and/or cocrystal thereof) is administered as a pharmaceutical composition that includes the chemical entity and one or more pharmaceutically acceptable excipients, and optionally one or more other therapeutic agents as described herein.

In some embodiments, the niclosamide compounds can be administered in combination with one or more conventional pharmaceutical excipients. Pharmaceutically acceptable excipients include, but are not limited to, ion exchangers, alumina, aluminum stearate, lecithin, self-emulsifying drug delivery systems (SEDDS) such as d-α-tocopherol polyethylene glycol 1000 succinate, surfactants used in pharmaceutical dosage forms such as Tweens, poloxamers or other similar polymeric delivery matrices, serum proteins, such as human serum albumin, buffer substances such as phosphates, tris, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium-chloride, zinc salts, colloidal silica, magnesium trisilicate, polyvinyl pyrrolidone, cellulose-based substances, polyethylene glycol, sodium carboxymethyl cellulose, polyacrylates, waxes, polyethylene-polyoxypropylene-block polymers, and wool fat. Cyclodextrins such as α-, β, and γ-cyclodextrin, or chemically modified derivatives such as hydroxyalkylcyclodextrins, including 2- and 3-hydroxypropyl-β-cyclodextrins, or other solubilized derivatives can also be used to enhance delivery of compounds described herein. Dosage forms or compositions containing a chemical entity as described herein in the range of 0.005% to 100% with the balance made up from non-toxic excipient may be prepared. The contemplated compositions may contain 0.001%-100% of a chemical entity provided herein, in one embodiment 0.1-95%, in another embodiment 75-85%, in a further embodiment 20-80%. Actual methods of preparing such dosage forms are known, or will be apparent, to those skilled in this art; for example, see *Remington: The Science and Practice of Pharmacy,* 22$^{nd}$ Edition (Pharmaceutical Press, London, U K. 2012).

In some embodiments, the niclosamide compounds described herein or a pharmaceutical composition thereof can be administered to subject in need thereof by any accepted route of administration. Acceptable routes of administration include, but are not limited to, buccal, cutaneous, endocervical, endosinusial, endotracheal, enteral, epidural, interstitial, intra-abdominal, intra-arterial, intrabronchial, intrabursal, intracerebral, intracisternal, intracoronary, intradermal, intraductal, intraduodenal, intradural, intraepidermal, intraesophageal, intragastric, intragingival, intraileal, intralymphatic, intramedullary, intrameningeal, intramuscular, intraovarian, intraperitoneal, intraprostatic, intrapulmonary, intrasinal, intraspinal, intrasynovial, intratesticular, intrathecal, intratubular, intratumor, intrauterine, intravascular, intravenous, nasal, nasogastric, oral, parenteral, percutaneous, peridural, rectal, respiratory (inhalation), subcutaneous, sublingual, submucosal, topical, transdermal, transmucosal, transtracheal, ureteral, urethral and vaginal.

Local Administration

In some embodiments, the niclosamide compounds described herein or a pharmaceutical composition thereof are suitable for local administration, e.g., local administration by way of administering the niclosamide compounds or composition thereof at a particular treatment site, (e.g., the respiratory tract, e.g., the upper respiratory tract (e.g., nose or nasal passage) or lower respiratory tract (e.g., lungs); e.g., the digestive tract, the gastrointestinal ("GI") tract, e.g., colon; e.g., eye, e.g., skin) so as to provide local administration of the chemical entity to the area in need of treatment (e.g., respiratory tract (e.g., nasal passage or the lungs) or the digestive tract (e.g., colon); eye, skin). In certain embodiments, relatively low systemic exposure of the niclosamide compounds occurs during said local administration. Examples of such compositions include, e.g., compositions suitable for administration by inhalation.

In some embodiments, the niclosamide compound described herein or a pharmaceutical composition thereof are suitable for local administration to the respiratory tract, e.g., the upper respiratory tract (e.g., nose or nasal passage) or lower respiratory tract (e.g., lungs). In certain embodiments, upon administration, the local concentration of the niclosamide compound in the respiratory tract is higher (e.g., from about 2 times higher to about 1,000 times higher; from about 2 times higher to about 900 times higher; from about 2 times higher to about 800 times higher; from about 2 times higher to about 700 times higher; from about 2 times higher to about 500 times higher; from about 2 times higher to about 400 times higher; from about 2 times higher to about 300 times higher; from about 2 times higher to about 200 times higher; from about 2 times higher to about 100 times higher; from about 2 times higher to about 50 times higher, from about 5 times higher to about 1,000 times higher; from about 5 times higher to about 900 times higher; from about 5 times higher to about 800 times higher; from about 2 times higher to about 700 times higher; from about 5 times higher to about 500 times higher; from about 5 times higher to about 400 times higher; from about 5 times higher to about 300 times higher; from about 5 times higher to about 200 times higher; from about 5 times higher to about 100 times higher; from about 5 times higher to about 50 times higher; from about 5 times higher to about 25 times higher; from about 5 times higher to about 15 times higher; e.g., about 1,000 times higher, about 900 times higher, about 800 times higher, about 700 times higher, about 600 times higher, about 500 times higher, about 400 times higher, about 300 times higher, about 200 times higher, about 100 times higher, about 50 times higher, about 25 time higher, about 20 times higher, about 15 times higher, about 10 times higher, about 5 times higher) than the concentration of the chemical entity in the plasma compartment. In certain of these embodiments, the chemical entity in the plasma compartment is subject to first pass metabolism.

In some embodiments, the niclosamide compound described herein or a pharmaceutical composition thereof are suitable for local administration to one or more specific locations within the respiratory tract. For example, at least some of the niclosamide compound is present in the upper respiratory tract (e.g., nose and nasal passages, paranasal sinuses, the pharynx, and the portion of the larynx above the vocal folds (cords) (e.g., nose and nasal passages); or at least some of the niclosamide compound is present in the lower respiratory tract (e.g., portion of the larynx below the vocal folds, trachea, bronchi, and lungs (e.g., lungs)). Methods of said local administration can include, without limitation, respiratory administration such as inhalation or intranasal administration.

In some embodiments, the niclosamide compound described herein or a pharmaceutical composition thereof are suitable for local administration to the GI tract, e.g., colon. In certain embodiments, upon administration, the local concentration of the niclosamide compound in the GI tract is higher (e.g., from about 2 times higher to about 1,000 times higher; from about 2 times higher to about 900 times higher; from about 2 times higher to about 800 times higher; from about 2 times higher to about 700 times higher; from about 2 times higher to about 500 times higher; from about 2 times higher to about 400 times higher; from about 2 times higher to about 300 times higher; from about 2 times higher to about 200 times higher; from about 2 times higher to about 100 times higher; from about 2 times higher to about 50 times higher, from about 5 times higher to about 1,000 times higher; from about 5 times higher to about 900 times higher; from about 5 times higher to about 800 times higher; from about 2 times higher to about 700 times higher; from about 5 times higher to about 500 times higher; from about 5 times higher to about 400 times higher; from about 5 times higher to about 300 times higher; from about 5 times higher to about 200 times higher; from about 5 times higher to about 100 times higher; from about 5 times higher to about 50 times higher; from about 5 times higher to about 25 times higher; from about 5 times higher to about 15 times higher; e.g., about 1,000 times higher, about 900 times higher, about 800 times higher, about 700 times higher, about 600 times higher, about 500 times higher, about 400 times higher, about 300 times higher, about 200 times higher, about 100 times higher, about 50 times higher, about 25 time higher, about 20 times higher, about 15 times higher, about 10 times higher, about 5 times higher) than the concentration of the chemical entity in the plasma compartment. In certain of these embodiments, the chemical entity in the plasma compartment is subject to first pass metabolism.

In some embodiments, the niclosamide compound described herein or a pharmaceutical composition thereof are suitable for local administration to one or more specific locations within the digestive or GI tract, e.g., colon. For example, at least some of the niclosamide compound is present in the upper GI tract (e.g., stomach); or at least some of the niclosamide compound is present in the lower GI tract (e.g., the large intestine, e.g., the colon, e.g., the ascending colon and/or transverse colon and/or distal colon; or the small bowel). As a further example, at least some of the niclosamide compound is present in the ascending colon and/or the transverse colon and/or the distal colon and/or the small bowel and/or the stomach. Methods of said local administration can include, without limitation, oral administration and/or rectal administration.

In one aspect, provided herein is a composition comprising a niclosamide compound or co-crystal as described anywhere herein and one or more pharmaceutically acceptable excipients, wherein the composition is suitable for oral administration.

In one aspect, provided herein is a composition comprising a niclosamide compound or co-crystal as described anywhere herein and one or more pharmaceutically acceptable excipients, wherein the composition is suitable for local, topical administration. In certain embodiments, the chemical entities described herein or a pharmaceutical composition thereof are suitable for rectal administration. Rectal compositions include, without limitation, enemas, rectal gels, rectal foams, rectal aerosols, suppositories, jelly suppositories, and enemas (e.g., retention enemas).

Pharmacologically acceptable excipients usable in the rectal composition as a gel, cream, enema, or rectal suppository, include, without limitation, any one or more of cocoa butter glycerides, synthetic polymers such as polyvinylpyrrolidone, PEG (like PEG ointments), glycerine, glycerinated gelatin, hydrogenated vegetable oils, poloxamers, mixtures of polyethylene glycols of various molecular weights and fatty acid esters of polyethylene glycol Vaseline, anhydrous lanolin, shark liver oil, sodium saccharinate, menthol, sweet almond oil, sorbitol, sodium benzoate, anoxid SBN, vanilla essential oil, aerosol, parabens in phenoxyethanol, sodium methyl p-oxybenzoate, sodium propyl p-oxybenzoate, diethylamine, carbomers, carbopol, methyloxybenzoate, macrogol cetostearyl ether, cocoyl caprylocaprate, isopropyl alcohol, propylene glycol, liquid paraffin, xanthan gum, carboxy-metabisulfite, sodium edetate, sodium benzoate, potassium metabisulfite, grapefruit seed extract, methyl sulfonyl methane (MSM), lactic acid, glycine, vitamins, such as vitamin A and E and potassium acetate.

In certain embodiments, suppositories can be prepared by mixing the chemical entities described herein with suitable non-irritating excipients or carriers such as cocoa butter, polyethylene glycol or a suppository wax which are solid at ambient temperature but liquid at body temperature and therefore melt in the rectum and release the active compound. In other embodiments, compositions for rectal administration are in the form of an enema.

In some embodiments, administration of a single dose of the composition to a subject produces a local concentration of the niclosamide compound in the GI tract (e.g., colon) of the subject that is higher than the concentration of the compound in the plasma compartment of the subject.

In some embodiments, administration of a single dose of the composition to a subject produces a local concentration of the niclosamide compound in the GI tract (e.g., colon) of the subject that is at least about 200 times higher than the concentration of the compound in the plasma compartment of the subject.

In some embodiments, administration of a single dose of the composition to a subject produces a local concentration of the niclosamide compound in the GI tract (e.g., colon) of the subject that is at least about 300 times higher than the concentration of the compound in the plasma compartment of the subject.

In some embodiments, administration of a single dose of the composition to a subject produces a local concentration of the niclosamide compound in the GI tract (e.g., colon) of the subject that is at least about 500 times higher than the concentration of the compound in the plasma compartment of the subject.

In some embodiments, administration of a single dose of the composition to a subject produces a local concentration of the niclosamide compound in the GI tract (e.g., colon) of the subject that is at least about 700 times higher than the concentration of the compound in the plasma compartment of the subject.

In some embodiments, the local concentration of the niclosamide compound in the GI tract (e.g., colon) of the subject is higher than a local concentration produced by oral administration of a single dose of a second composition comprising a second niclosamide compound, wherein the second niclosamide compound has a higher particle size than the first niclosamide compound.

In some embodiments, the local concentration of the niclosamide compound in the GI tract (e.g., colon) of the subject is at least about 2 times higher than a local concentration produced by oral administration of a single dose of a second composition comprising a second niclosamide compound, wherein the second niclosamide compound has a higher particle size than the first niclosamide compound.

In some embodiments, the local concentration of the niclosamide compound in the GI tract (e.g., colon) of the subject is at least about 5 times higher than a local concentration produced by oral administration of a single dose of a second composition comprising a second niclosamide compound, wherein the second niclosamide compound has a higher particle size than the first niclosamide compound.

In some embodiments, the local concentration of the niclosamide compound in the GI tract (e.g., colon) of the subject is at least about 10 times higher than a local concentration produced by oral administration of a single dose of a second composition comprising a second niclosamide compound, wherein the second niclosamide compound has a higher particle size than the first niclosamide compound.

In some embodiments, the local concentration of the niclosamide compound in the GI tract (e.g., colon) of the subject is at least about 25 times higher than a local concentration produced by oral administration of a single dose of a second composition comprising a second niclosamide compound, wherein the second niclosamide compound has a higher particle size than the first niclosamide compound.

In some embodiments, the local concentration of the niclosamide compound in the GI tract (e.g., colon) of the subject is at least about 50 times higher than a local concentration produced by oral administration of a single dose of a second composition comprising a second niclosamide compound, wherein the second niclosamide compound has a higher particle size than the first niclosamide compound.

In some embodiments, the local concentration of the niclosamide compound in the GI tract (e.g., colon) of the subject is at least about 100 times higher than a local concentration produced by oral administration of a single dose of a second composition comprising a second niclosamide compound, wherein the second niclosamide compound has a higher particle size than the first niclosamide compound.

In some embodiments, the second niclosamide compound has a particle size distribution D(0.9) of from about 25.0 μm to about 65.0 μm.

In some embodiments, the second niclosamide compound has a particle size distribution D(0.1) of from about 4.0 μm to about 10.0 μm.

In another aspect, provided herein is a dosage form (e.g., a unit dosage form) comprising a composition as described anywhere herein, wherein the dosage form is suitable for oral administration.

In another aspect, provided herein is a dosage form (e.g., a unit dosage form) comprising a composition as described anywhere herein, wherein the dosage form is suitable for rectal administration.

In some embodiments, the dosage form further comprises one or more components that chemically and/or structurally predispose the dosage form for delivery of the compound to the ascending colon.

In some embodiments, the dosage form further comprises one or more components that chemically and/or structurally predispose the dosage form for delivery of the compound to the transverse colon.

In some embodiments, the dosage form further comprises one or more components that chemically and/or structurally predispose the dosage form for delivery of the compound to the distal colon.

In some embodiments, the dosage form further comprises one or more components that chemically and/or structurally predispose the dosage form for delivery of the compound to the small bowel.

In one aspect, provided herein is a composition comprising a niclosamide compound or co-crystal as described anywhere herein and one or more pharmaceutically acceptable excipients, wherein the composition is suitable for respiratory administration (e.g., inhalation).

In some embodiments, administration of a single dose of the composition to a subject produces a local concentration of the niclosamide compound in the lower respiratory tract (e.g., lungs) of the subject that is higher than the concentration of the compound in the upper respiratory tract of the subject.

Inhalation and Intranasal Therapy

In some embodiments, niclosamide or a pharmaceutically acceptable salt thereof can be formulated into any suitable dosage form. Non-limiting examples of such dosage forms include aerosols, dispersions (e.g., aqueous oral dispersions, self-emulsifying dispersions, liposomal dispersions, dispersions with colloidal silica or nanospheres such as hydroxypropylmethylcellulose phthalate (HPMCP) nanospheres), pegylated liposomes, liquids, elixirs, suspensions (e.g., nanosuspensions), aerosols, controlled release formulations, lyophilized formulations, powders, delayed release formulations, extended release formulations, multiparticulate formulations, and mixed immediate release formulations. In some embodiments, niclosamide or a pharmaceutically acceptable salt thereof, can be formulated for administration intranasally and/or by inhalation, e.g., using an inhalation device.

An "inhalation device," as used herein, refers to any device that is capable of administering a drug formulation to the respiratory airways of a subject. Inhalation devices include conventional inhalation devices such as nebulizers, metered dose inhalers (MDIs), dry powder inhalers (DPIs), heat vaporizers, soft mist inhalers, thermal aerosol inhalers, or electrohydrodynamic-based solution misting inhalers. Inhalation devices also include nebulizers. "Nebulizer," as used herein, refers to a device that turns medications, compositions, formulations, suspensions, and mixtures, etc. into a fine aerosol mist for delivery to the lungs. Non-limiting examples of nebulizers include jet nebulizers, mesh nebulizers, and ultrasonic wave nebulizers. Nebulizers, metered dose inhalers, and soft mist inhalers deliver pharmaceuticals by forming an aerosol which includes droplet sizes that can easily be inhaled. The aerosol can be used by a subject within the bounds of an inhalation therapy, whereby the niclosamide or a pharmaceutically-acceptable salt thereof reaches the subject's respiratory tract upon inhalation. In some embodiments, the methods disclosed herein comprise administering to a subject a nominal dose of niclosamide or a pharmaceutically-acceptable salt thereof by an inhalation device, such as a nebulizer.

In some embodiments of the methods disclosed herein, administration of a composition comprising niclosamide or a pharmaceutically acceptable salt thereof, to a subject with an inhalation device, e.g., a nebulizer, a metered dose inhaler, a dry powder inhaler (DPI), a jet nebulizer, an ultrasonic wave nebulizer, a heat vaporizer, a soft mist inhaler, a thermal aerosol inhaler, or an electrohydrodynamic-based solution misting inhaler, is effective for the treatment or prophylaxis of COVID-19 in a subject.

Inhalation devices may be mechanical or electrical, and include, for example, jet nebulizers and ultrasonic nebulizers. Jet nebulizers generally utilize compressors to generate compressed air, which breaks the liquid medication into small breathable droplets, which form an aerosolized (atomized) mist. In some embodiments, when the subject breathes in, a valve at the top opens, which then allows air into the apparatus, thereby increasing the rate of mist generation; when the subject breathes out, the top valve closes, thereby slowing down mist generation while simultaneously permitting the subject to breathe out through the opening of a mouthpiece flap. Some nebulizers may provide the aerosol in a continuous mode (e.g., the eFlow from PARI Pharma Starnberg), by a breath enhanced mode (e.g., the PART LC Plus or Sprint from PARI Starnberg), by breath actuated mode dependent on the breathing pattern of the subject (e.g., the AeroEclipse from Trudell, Canada or the I-Neb from Philips Respironics), or according to given inhalation profile (e.g., the Akita from Activaero, Gmuenden, Germany).

Some conventional inhalation devices are disclosed in U.S. Pat. Nos. 9,566,399, 6,513,727, 6,513,519, 6,176,237, 6,085,741, 6,000,394, 5,957,389, 5,740,966, 5,549,102, 5,461,695, 5,458,136, 5,312,046, 5,309,900, 5,280,784, and 4,496,086, and International Publication Nos. WO 2018/191776 and WO 2018/213834, each of which is hereby incorporated by reference in its entirety. Commercial conventional inhalation devices are available from: PARI (Germany) under the trade names PARI LC Plus®., LC Star®., and PARI-Jet®; A & H Products, Inc. (Tulsa, Okla.) under the trade name AquaTower®; Hudson RCI (Temecula, Calif.) under the trade name AVA-NEB®; Intersurgical, Inc. (Liverpool, N.Y.) under the trade name Cirrus®; Salter Labs (Arvin, Calif.) under the trade name Salter 8900®; Respironics (Murrysville, Pa.) under the trade name Sidestream®; Bunnell (Salt Lake City, Utah) under the trade name Whisper Jet®; Smiths-Medical (Hyth Kent, UK) under the trade name Downdraft®, and DeVilbiss (Somerset, Pa.) under the trade name DeVilbiss®; or Trudell, Canada under the trade name AeroEclipse®.

In some embodiments of the methods disclosed herein, compositions comprising niclosamide or a pharmaceutically acceptable salt thereof are administered with a dry powder inhaler. Compositions administered with dry powder inhalers can include nanoparticles, spray dried materials, engineered porous particles with low mass median diameter but a high geometric diameter, liposomes, stealth (or PEGylated) liposomes, or combinations thereof. In some embodiments, compositions administered by dry powder inhalers administered in the methods disclosed herein comprise nanoparticle clusters that aggregate into micrometer sized particles at neutral or basic pH but dissociate into nanoparticles at the pH encountered in the lung. In some embodiments the nanoparticle clusters comprise fumaryl diketopiperazine. In some embodiments, compositions administered with dry powder inhalers comprise lactose.

In some embodiments, a dry powder inhaler used to administer an inhalation formulation in the methods disclosed herein comprises a pre-metered dose. For example a pre-metered dose inhaler can comprise a capsule pre-filled with a powder (e.g., a Plastiape Monodose inhaler). In some embodiments, a dry powder inhaler used to administer an inhalation formulation in the methods disclosed herein has a device-metered system such as Twisthaler, sold by Schering Plough, which comprises a reservoir to store a powder and a twisting top to dispense each dose. Inhalation formulations for administration with a dry powder inhaler may be prepared by blending niclosamide or a pharmaceutically acceptable salt thereof, with lactose, or spray drying niclosamide or a pharmaceutically acceptable salt thereof, or by pelletizing niclosamide or a pharmaceutically acceptable salt thereof, to form free-flowing spherical agglomerates.

In some embodiments of the methods disclosed herein, compositions comprising niclosamide or a pharmaceutically acceptable salt thereof are administered with a metered dose inhaler. In some embodiments, a composition administered with a metered dose inhaler in the methods disclosed herein comprises one or more of nanoparticles, spray dried materials, engineered porous particles with low mass median diameter but a high geometric diameter, liposomes, and stealth (or PEGylated) liposomes.

In some embodiments of the methods disclosed herein, compositions comprising niclosamide or a pharmaceutically acceptable salt thereof are administered with a thermal aerosol inhaler.

In some embodiments of the methods disclosed herein, compositions comprising niclosamide or a pharmaceutically acceptable salt thereof are administered with an electrohydrodynamic-based solution misting inhaler. In some embodiments, the aerosol in the electrohydrodynamic-based solution-misting inhaler is generated by subjecting a solution of niclosamide or a pharmaceutically acceptable salt thereof, or a liposome or pegylated liposome comprising niclosamide or a pharmaceutically acceptable salt thereof, to electrohydrodynamic forces through electrostatic energy.

Nebulizers are inhalation devices that comprise a microperforated membrane through which a liquid solution is converted through electrical or mechanical means into aerosol droplets suitable for inhalation. Nebulizers can deliver a large fraction of a loaded dose to a subject. In some embodiments, the nebulizer also utilizes one or more actively or passively vibrating microperforated membranes. In some embodiments, the nebulizer contains one or more oscillating membranes. In some embodiments, the nebulizer contains a vibrating mesh or plate with multiple apertures and optionally a vibration generator with an aerosol mixing chamber. In some such embodiments, the mixing chamber functions to collect (or stage) the aerosol from the aerosol generator. In some embodiments, an inhalation valve is also used to allow an inflow of ambient air into the mixing chamber during an inhalation phase and is closed to prevent escape of the aerosol from the mixing chamber during an exhalation phase. In some such embodiments, the exhalation valve is arranged at a mouthpiece which is removably mounted at the mixing chamber and through which the subject inhales the aerosol from the mixing chamber. Still yet, in some embodiments, the nebulizer contains a pulsating membrane. In some embodiments, the nebulizer is continuously operating.

In some embodiments, the nebulizer contains a vibrating micro-perforated membrane of tapered nozzles that generates a plume of droplets without the need for compressed gas. In these embodiments, a solution in the micro-perforated membrane nebulizer is in contact with a membrane, the opposite side of which is open to the air. The membrane is perforated by a large number of nozzle orifices of an atomizing head. An aerosol is created when alternating acoustic pressure in the solution is built up in the vicinity of the membrane causing the fluid on the liquid side of the membrane to be emitted through the nozzles as uniformly sized droplets.

Some embodiments of nebulizers use passive nozzle membranes and a separate piezoelectric transducer that stimulates the membrane. In contrast, some nebulizers employ an active nozzle membrane, which use the acoustic pressure in the nebulizer to generate very fine droplets of solution via the high frequency vibration of the nozzle membrane.

Some nebulizers can contain a resonant system. For example, in such nebulizers, the membrane is driven by a frequency for which the amplitude of the vibrational movement at the center of the membrane is particularly large, resulting in a focused acoustic pressure in the vicinity of the nozzle; the resonant frequency may be about 100 kHz. A flexible mounting is used to keep unwanted loss of vibrational energy to the mechanical surroundings of the atomizing head to a minimum. In some embodiments, the vibrating membrane of the nebulizer may be made stainless steel, or of a nickel-palladium alloy by electroforming.

In some embodiments, a nebulizer may be adapted or adaptable to operate in conjunction with a unit dosage form, such as an ampule or vial, which contains a single dose of a composition comprising niclosamide, or a pharmaceutically-acceptable salt thereof, for the treatment of COVID-19. The unit dosage form comprises a container that contains an inhalation formulation comprising the niclosamide, or a pharmaceutically-acceptable salt thereof. The container is adapted to cooperate with the nebulizer device in such a way as to permit administration of the nominal dose of the inhalation formulation to a subject. In some embodiments, the nebulizer and the unit dosage form are configured so that they are useable together, but not with other devices or dosage forms. In some particular embodiments, the unit dosage form is configured such that it fits into a keyhole-like structure in the nebulizer, but will not operate with other nebulizer devices. In such embodiments, the nebulizer is configured such that it will accept and properly operate with the unit dosage form containing the niclosamide, or a pharmaceutically-acceptable salt thereof, but not with other dosage forms.

Commercial high efficiency nebulizers are available from: PARI (Germany) under the trade name eFlow®; Aerogen, Ltd. (Ireland) under the trade names AeroNeb® Go and AeroNeb® Pro, AeroNeb® Solo, and other nebulizers utilizing the OnQ® nebulizer technology; Respironics (Murrysville, Calif.) under the trade names I-Neb®; Omron (Bannockburn, Ill.) under the trade name Micro-Air®; Activaero (Germany) under the trade name Akita®, and AerovectRx (Atlanta, Ga.) under the trade name AerovectRx®.

In some embodiments, a composition comprising niclosamide, or a pharmaceutically acceptable salt thereof, is formulated as an inhalable nanosuspension (see, e.g., Costabile et al. Mol Pharm. 2015 Aug. 3; 12(8):2604-17.) In some embodiments, an inhalable nanosuspension of niclosamide, or a pharmaceutically acceptable salt thereof, is administered to a subject using a nebulizer.

In some embodiments, devices for intranasal administration of niclosamide, or a pharmaceutically acceptable salt thereof, include one or more features present in any inhalation device described herein. In some embodiments, devices for intranasal administration of niclosamide, or a pharmaceutically acceptable salt thereof, are spray devices. Suitable commercially available nasal spray devices include Accuspray™ (Becton Dickinson). In some embodiments, spray devices for intranasal use are devices for which the performance of the device is not dependent upon the pressure applied by the user. These devices are known as pressure threshold devices. Pressure threshold deviced release liquid from the nozzle only when a threshold pressure is applied. These devices make it easier to achieve a spray with a regular droplet size. Pressure threshold devices suitable for use with the present invention are known in the art and are described for example in WO 91/13281, EP 311863, and EP 516636. Pressure threshold devices are commercially available from Pfeifer GmbH and are also described in Bommer, R. Pharmaceutical Technology Europe, September 1999.

In some embodiments, the intranasal devices can administer niclosamide, or a pharmaceutically acceptable salt thereof, by means of bi-dose delivery. Bi-dose devices contain two sub-doses of a single dose, one sub-dose for administration to each nostril. Generally, the two sub-doses are present in a single chamber and the construction of the device allows for efficient delivery of a single sub-dose at a time. Alternatively, a monodose device may be used for administering the vaccines according to the invention.

In some embodiments, niclosamide, or a pharmaceutically acceptable salt thereof, is formulated as an ointment or gel for intranasal delivery.

In some embodiments, the compositions disclosed herein can include one or pharmaceutical excipients that provide suitable properties for intranasal administration and/or administration by inhalation of niclosamide, or a pharmaceutically acceptable salt thereof. See, e.g., Labiris and Dolovich, *Br J Clin Pharmacol.* 2003 December; 56(6): 600-612. Non-limiting examples of such pharmaceutical excipients can include surfactants, suspending agents, viscosity enhancing agents, wetting agents, and propellants.

"Suspending agents" include compounds such as polyvinylpyrrolidone, e.g., polyvinylpyrrolidone K12, polyvinylpyrrolidone K17, polyvinylpyrrolidone K25, or polyvinylpyrrolidone K30, vinyl pyrrolidone/vinyl acetate copolymer (S630), polyethylene glycol e.g., the polyethylene glycol can have a molecular weight of about 300 to about 6000, or about 3350 to about 4000, or about 7000 to about 5400, sodium carboxymethylcellulose, methylcellulose, hydroxypropylmethylcellulose, hydroxymethylcellulose acetate stearate, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

"Surfactants" include compounds such as sodium lauryl sulfate, sodium docusate, Tween 60 or 80, triacetin, vitamin E TPGS, sorbitan monooleate, polyoxyethylene sorbitan monooleate, polysorbates, poloxamers, bile salts, glyceryl monostearate, copolymers of ethylene oxide and propylene oxide, e.g., Pluronic® (BASF), and the like. Additional examples of surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40.

"Viscosity enhancing agents" include, e.g., methyl cellulose, xanthan gum, carboxymethyl cellulose, hydroxypropyl cellulose, hydroxypropylmethyl cellulose, hydroxypropylmethyl cellulose acetate stearate, hydroxypropylmethyl cellulose phthalate, carbomer, polyvinyl alcohol, alginates, acacia, chitosans, and combinations thereof.

"Wetting agents" include compounds such as oleic acid, glyceryl monostearate, sorbitan monooleate, sorbitan monolaurate, triethanolamine oleate, polyoxyethylene sorbitan monooleate, polyoxyethylene sorbitan monolaurate, sodium docusate, sodium oleate, sodium lauryl sulfate, sodium doccusate, triacetin, Tween 80, vitamin E TPGS, ammonium salts and the like.

Non-limiting examples of propellants include chlorofluorocarbons (CFC) and hydrofluoroalkanes (HFAs).

Compostions and formulations of the disclosure may have a surface tension effective for deposition, penetration or retention of the composition primarily in the peripheral lung regions, including the bronchioles and alveoli Oral Delivery In other embodiments, the chemical entities described herein or a pharmaceutical composition thereof are suitable for local delivery to the digestive or GI tract by way of oral administration (e.g., solid or liquid dosage forms.).

Solid dosage forms for oral administration include capsules, tablets, pills, powders, and granules. In such solid dosage forms, the chemical entity is mixed with one or more pharmaceutically acceptable excipients, such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents. Solid compositions of a similar type may also be employed as fillers in soft and hard-filled gelatin capsules using such excipients as lactose or milk sugar as well as high molecular weight polyethylene glycols and the like.

In one embodiment, the compositions will take the form of a unit dosage form such as a pill or tablet and thus the composition may contain, along with a chemical entity provided herein, a diluent such as lactose, sucrose, dicalcium phosphate, or the like; a lubricant such as magnesium stearate or the like; and a binder such as starch, gum acacia, polyvinylpyrrolidine, gelatin, cellulose, cellulose derivatives or the like. In another solid dosage form, a powder, marume, solution or suspension (e.g., in propylene carbonate, vegetable oils, PEG's, poloxamer 124 or triglycerides) is encapsulated in a capsule (gelatin or cellulose base capsule). Unit dosage forms in which one or more chemical entities provided herein or additional active agents are physically separated are also contemplated; e.g., capsules with granules (or tablets in a capsule) of each drug; two-layer tablets; two-compartment gel caps, etc. Enteric coated or delayed release oral dosage forms are also contemplated.

Other physiologically acceptable compounds include wetting agents, emulsifying agents, dispersing agents or preservatives that are particularly useful for preventing the growth or action of microorganisms. Various preservatives are well known and include, for example, phenol and ascorbic acid.

In certain embodiments the excipients are sterile and generally free of undesirable matter. These compositions can be sterilized by conventional, well-known sterilization techniques. For various oral dosage form excipients such as tablets and capsules sterility is not required. The USP/NF standard is usually sufficient.

In certain embodiments, solid oral dosage forms can further include one or more components that chemically and/or structurally predispose the composition for delivery of the chemical entity to the stomach or the lower GI; e.g., the ascending colon and/or transverse colon and/or distal colon and/or small bowel. Exemplary formulation techniques are described in, e.g., Filipski, K. J., et al., *Current Topics in Medicinal Chemistry,* 2013, 13, 776-802, which is incorporated herein by reference in its entirety.

Examples include upper-GI targeting techniques, e.g., Accordion Pill (Intec Pharma), floating capsules, and materials capable of adhering to mucosal walls.

Other examples include lower-GI targeting techniques. For targeting various regions in the intestinal tract, several enteric/pH-responsive coatings and excipients are available. These materials are typically polymers that are designed to dissolve or erode at specific pH ranges, selected based upon the GI region of desired drug release. These materials also function to protect acid labile drugs from gastric fluid or limit exposure in cases where the active ingredient may be irritating to the upper GI (e.g., hydroxypropyl methylcellulose phthalate series, Coateric (polyvinyl acetate phthalate), cellulose acetate phthalate, hydroxypropyl methylcellulose acetate succinate, Eudragit series (methacrylic acid-methyl methacrylate copolymers), and Marcoat). Other techniques include dosage forms that respond to local flora in the GI tract, Pressure-controlled colon delivery capsule, and Pulsincap.

Liquid dosage forms for oral administration include pharmaceutically acceptable emulsions, microemulsions, solutions, suspensions, syrups and elixirs. In addition to the chemical entities described herein, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents. In certain embodiments, the liquid dosage form is a mouthwash. In certain embodiments, such liquid oral dosage forms are useful for local and topical administration to the digestive or GI tract, e.g., digestive tract, e.g., oral cavity.

Orally administered niclosamide can be delivered to the digestive tract (e.g., the colon) using one or more delivery systems. Non-limiting examples of delivery systems include: prodrugs (e.g., azo-conjugates, pectin prodrugs, or prodrugs formed by conjugation (e.g., through azo-bond) to one or more carrier molecules such as cyclodextrin, glucuronide, dextran, amino acids (e.g., sodium alginate), and HMPC); biodegradable delivery systems (e.g., colon-specific biodegradable delivery systems)(e.g., biodegradable delivery systems using guar gum and derivatives thereof (e.g., AcGGM), azo-aromatic polymers); matrix-based systems (e.g., by embedding niclosamide in polymer matrices such as starch derived polymer matrices (e.g., pH-sensitive and/or biodegradable matrices such as Assam Bora rice starch matrices)); time-released systems (e.g., using pH sensitive polymers); bioadhesive systems (e.g., using polymers such as polycarbophils, polyurethanes, polyethylene oxide, Assam Bora rice starch); multiparticulate systems (e.g., using microspheres (e.g., biodegradable microspheres) such as chitosan microspheres (e.g., coated with Eudragit), guar gum base microspheres, polysaccharide pectins, pectin-4-aminothiophenol (Pec-ATP) conjugates, calcium alginate-carboxymethyl cellulose (CA-CMC), nanoparticles (e.g., with MMT-K10 clay), each of which can be optionally coated with a pH sensitive polymer (e.g., Eudragit)); polysaccharide-based delivery systems (e.g., with xanthan gum, guar gum, pectin (e.g., mixture with an insoluble polymer such as ethyl cellulose), chitosan, HPMC derivatives, chondroitin sulfate, galactomannan, amylose, or combinations of polysaccharides such as combinations of cellulose derivatives (e.g., combinations of non-enteric cellulose esters such as cellulose acetate and enteric cellulose esters such as CAP and HPMCP; e.g., pectin-HPMC, chitosan-HPMC, chitosan-pectin, guar gum-chitosan, and dextran-chitosan)); coatings (e.g., with pH sensitive polymers such as enteric-soluble polymers such as methacrylic-acid based polymers (e.g., Eudragit, Eudragit L, or Eudragit S) or Landolphia owariensis latex (LOL), with acid-soluble polymers such as Eudragit E, with pulsatile coatings, with rupturable film coatings, with permeable or semi-permeable film coatings, and optionally using compression-coating systems wherein the core tablet comprising niclosamide and one or more polymer coatings is further coated with a coating excipient (e.g., almond-gum matrix); pressure-controlled delivery systems; osmotic controlled delivery systems (e.g., OROS-CT); and pulsincap systems. Additional examples are described in Amido, *AAPS PharmSciTech*, Vol. 16, No. 4, August 2015, which is incorporated herein by reference in its entirety.

Non-limiting examples of oral dosage forms suitable for the selective delivery to the digestive tract (e.g., to the colon) include: delayed release tablets; timed release capsules; immediate release tablets; immediate release capsules (e.g., soft gelatin immediate release capsules); multi-matrix tablets; extended release tablets; gastro-resistant prolonged-release tablets; oral colon-targeted pellets; oral solutions; and oral powders. Additional examples are described in Amido, *AAPS PharmSciTech*, Vol. 16, No. 4, August 2015, which is incorporated herein by reference in its entirety.

Further non-limiting examples of dosage forms suitable for selective delivery to the digestive tract (e.g., to the colon) include those described in U.S. Pat. Nos. 9,192,583; 6,224,910; 5,914,132; 9,237,760; 9,023,368; 6,228,396; 10,588,864; *Int. J. Appl. Res. Nat. Prod.*, 2012, 5, 1-16; *Carbohydrate Polymers*, 2013, 92, 367-373; and *J. Controlled Release*, 1996, 38, 75-94, each of which is incorporated herein by reference in its entirety.

Enema Formulations

In some embodiments, enema formulations containing the chemical entities described herein are provided in "ready-to-use" form.

In some embodiments, enema formulations containing the chemical entities described herein are provided in one or more kits or packs. In certain embodiments, the kit or pack includes two or more separately contained/packaged components, e.g. two components, which when mixed together, provide the desired formulation (e.g., as a suspension). In certain of these embodiments, the two component system includes a first component and a second component, in which: (i) the first component (e.g., contained in a sachet) includes the chemical entity (as described anywhere herein) and optionally one or more pharmaceutically acceptable excipients (e.g., together formulated as a solid preparation, e.g., together formulated as a wet granulated solid preparation); and (ii) the second component (e.g., contained in a vial or bottle) includes one or more liquids and optionally one or more other pharmaceutically acceptable excipients together forming a liquid carrier. Prior to use (e.g., immediately prior to use), the contents of (i) and (ii) are combined to form the desired enema formulation, e.g., as a suspension. In other embodiments, each of component (i) and (ii) is provided in its own separate kit or pack.

In some embodiments, each of the one or more liquids is water, or a physiologically acceptable solvent, or a mixture of water and one or more physiologically acceptable solvents. Typical such solvents include, without limitation, glycerol, ethylene glycol, propylene glycol, polyethylene glycol and polypropylene glycol. In certain embodiments, each of the one or more liquids is water. In other embodiments, each of the one or more liquids is an oil, e.g. natural and/or synthetic oils that are commonly used in pharmaceutical preparations.

Further pharmaceutical excipients and carriers that may be used in the pharmaceutical products herein described are listed in various handbooks (e.g. D. E. Bugay and W. P. Findlay (Eds) Pharmaceutical excipients (Marcel Dekker, New York, 1999), E-M Hoepfner, A. Reng and P. C. Schmidt (Eds) Fiedler Encyclopedia of Excipients for Pharmaceuticals, Cosmetics and Related Areas (Edition Cantor, Munich, 2002) and H. P. Fielder (Ed) Lexikon der Hilfsstoffe für Pharmazie, Kosmetik and angrenzende Gebiete (Edition Cantor Aulendorf, 1989)).

In some embodiments, each of the one or more pharmaceutically acceptable excipients can be independently selected from thickeners, viscosity enhancing agents, bulking agents, mucoadhesive agents, penetration enhancers, buffers, preservatives, diluents, binders, lubricants, glidants, disintegrants, fillers, solubilizing agents, pH modifying agents, preservatives, stabilizing agents, anti-oxidants, wetting or emulsifying agents, suspending agents, pigments, colorants, isotonic agents, chelating agents, emulsifiers, and diagnostic agents.

In certain embodiments, each of the one or more pharmaceutically acceptable excipients can be independently selected from thickeners, viscosity enhancing agents, mucoadhesive agents, buffers, preservatives, diluents, binders, lubricants, glidants, disintegrants, and fillers.

In certain embodiments, each of the one or more pharmaceutically acceptable excipients can be independently selected from thickeners, viscosity enhancing agents, bulking agents, mucoadhesive agents, buffers, preservatives, and fillers.

In certain embodiments, each of the one or more pharmaceutically acceptable excipients can be independently selected from diluents, binders, lubricants, glidants, and disintegrants.

Examples of thickeners, viscosity enhancing agents, and mucoadhesive agents include without limitation: gums, e.g.

xanthan gum, guar gum, locust bean gum, tragacanth gums, karaya gum, ghatti gum, cholla gum, psyllium seed gum and gum arabic; poly(carboxylic acid-containing) based polymers, such as poly (acrylic, maleic, itaconic, citraconic, hydroxyethyl methacrylic or methacrylic) acid which have strong hydrogen-bonding groups, or derivatives thereof such as salts and esters; cellulose derivatives, such as methyl cellulose, ethyl cellulose, methylethyl cellulose, hydroxymethyl cellulose, hydroxyethyl cellulose, hydroxypropyl cellulose, hydroxyethyl ethyl cellulose, carboxymethyl cellulose, hydroxypropylmethyl cellulose or cellulose esters or ethers or derivatives or salts thereof; clays such as manomorillonite clays, e.g. Veegun, attapulgite clay; polysaccharides such as dextran, pectin, amylopectin, agar, mannan or polygalactonic acid or starches such as hydroxypropyl starch or carboxymethyl starch; polypeptides such as casein, gluten, gelatin, fibrin glue; chitosan, e.g. lactate or glutamate or carboxymethyl chitin; glycosaminoglycans such as hyaluronic acid; metals or water soluble salts of alginic acid such as sodium alginate or magnesium alginate; schleroglucan; adhesives containing bismuth oxide or aluminium oxide; atherocollagen; polyvinyl polymers such as carboxyvinyl polymers; polyvinylpyrrolidone (povidone); polyvinyl alcohol; polyvinyl acetates, polyvinylmethyl ethers, polyvinyl chlorides, polyvinylidenes, and/or the like; polycarboxylated vinyl polymers such as polyacrylic acid as mentioned above; polysiloxanes; polyethers; polyethylene oxides and glycols; polyalkoxys and polyacrylamides and derivatives and salts thereof. Preferred examples can include cellulose derivatives, such as methyl cellulose, ethyl cellulose, methylethyl cellulose, hydroxymethyl cellulose, hydroxyethyl cellulose, hydroxypropyl cellulose, hydroxyethyl ethyl cellulose, carboxymethyl cellulose, hydroxypropylmethyl cellulose or cellulose esters or ethers or derivatives or salts thereof (e.g., methyl cellulose); and polyvinyl polymers such as polyvinylpyrrolidone (povidone).

Examples of preservatives include without limitation: benzalkonium chloride, benzoxonium chloride, benzethonium chloride, cetrimide, sepazonium chloride, cetylpyridinium chloride, domiphen bromide (Bradosol®), thiomersal, phenylmercuric nitrate, phenylmercuric acetate, phenylmercuric borate, methylparaben, propylparaben, chlorobutanol, benzyl alcohol, phenyl ethyl alcohol, chlorohexidine, polyhexamethylene biguanide, sodium perborate, imidazolidinyl urea, sorbic acid, Purite®), Polyquart®), and sodium perborate tetrahydrate and the like.

In certain embodiments, the preservative is a paraben, or a pharmaceutically acceptable salt thereof. In some embodiments, the paraben is an alkyl substituted 4-hydroxybenzoate, or a pharmaceutically acceptable salt or ester thereof. In certain embodiments, the alkyl is a C1-C4 alkyl. In certain embodiments, the preservative is methyl 4-hydroxybenzoate (methylparaben), or a pharmaceutically acceptable salt or ester thereof, propyl 4-hydroxybenzoate (propylparaben), or a pharmaceutically acceptable salt or ester thereof, or a combination thereof.

Examples of buffers include without limitation: phosphate buffer system (sodium dihydrogen phosphate dehydrate, disodium phosphate dodecahydrate, bibasic sodium phosphate, anhydrous monobasic sodium phosphate), bicarbonate buffer system, and bisulfate buffer system.

Examples of disintegrants include, without limitation: carmellose calcium, low substituted hydroxypropyl cellulose (L-HPC), carmellose, croscarmellose sodium, partially pregelatinized starch, dry starch, carboxymethyl starch sodium, crospovidone, polysorbate 80 (polyoxyethylenesorbitan oleate), starch, sodium starch glycolate, hydroxypropyl cellulose pregelatinized starch, clays, cellulose, alginine, gums or cross linked polymers, such as cross-linked PVP (Polyplasdone XL from GAF Chemical Corp). In certain embodiments, the disintegrant is crospovidone.

Examples of glidants and lubricants (aggregation inhibitors) include without limitation: talc, magnesium stearate, calcium stearate, colloidal silica, stearic acid, aqueous silicon dioxide, synthetic magnesium silicate, fine granulated silicon oxide, starch, sodium laurylsulfate, boric acid, magnesium oxide, waxes, hydrogenated oil, polyethylene glycol, sodium benzoate, stearic acid glycerol behenate, polyethylene glycol, and mineral oil. In certain embodiments, the glidant/lubricant is magnesium stearate, talc, and/or colloidal silica; e.g., magnesium stearate and/or talc.

Examples of diluents, also referred to as "fillers" or "bulking agents" include without limitation: dicalcium phosphate dihydrate, calcium sulfate, lactose (e.g., lactose monohydrate), sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar. In certain embodiments, the diluent is lactose (e.g., lactose monohydrate).

Examples of binders include without limitation: starch, pregelatinized starch, gelatin, sugars (including sucrose, glucose, dxtrose, lactose and sorbitol), polyethylene glycol, waxes, natural and synthetic gums such as acacia tragacanth, sodium alginate cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone (povidone). In certain embodiments, the binder is polyvinylpyrrolidone(povidone).

In some embodiments, enema formulations containing the chemical entities described herein include water and one or more (e.g., all) of the following excipients:

- One or more (e.g., one, two, or three) thickeners, viscosity enhancing agents, binders, and/or mucoadhesive agents (e.g., cellulose or cellulose esters or ethers or derivatives or salts thereof (e.g., methyl cellulose); and polyvinyl polymers such as polyvinylpyrrolidone (povidone);
- One or more (e.g., one or two; e.g., two) preservatives, such as a paraben, e.g., methyl 4-hydroxybenzoate (methylparaben), or a pharmaceutically acceptable salt or ester thereof, propyl 4-hydroxybenzoate (propylparaben), or a pharmaceutically acceptable salt or ester thereof, or a combination thereof;
- One or more (e.g., one or two; e.g., two) buffers, such as phosphate buffer system (e.g., sodium dihydrogen phosphate dehydrate, disodium phosphate dodecahydrate);
- One or more (e.g., one or two, e.g., two) glidants and/or lubricants, such as magnesium stearate and/or talc;
- One or more (e.g., one or two; e.g., one) disintegrants, such as crospovidone; and
- One or more (e.g., one or two; e.g., one) diluents, such as lactose (e.g., lactose monohydrate).

In certain of these embodiments, the chemical entity is a niclosamide compound, or a pharmaceutically acceptable salt and/or hydrate and/or cocrystal thereof.

In certain embodiments, enema formulations containing the chemical entities described herein include water, methyl cellulose, povidone, methylparaben, propylparaben, sodium dihydrogen phosphate dehydrate, disodium phosphate dodecahydrate, crospovidone, lactose monohydrate, magnesium stearate, and talc. In certain of these embodiments, the chemical entity is a niclosamide compound, or a pharmaceutically acceptable salt and/or hydrate and/or cocrystal thereof.

In certain embodiments, enema formulations containing the chemical entities described herein are provided in one or more kits or packs. In certain embodiments, the kit or pack includes two separately contained/packaged components, which when mixed together, provide the desired formulation (e.g., as a suspension). In certain of these embodiments, the two component system includes a first component and a second component, in which: (i) the first component (e.g., contained in a sachet) includes the chemical entity (as described anywhere herein) and one or more pharmaceutically acceptable excipients (e.g., together formulated as a solid preparation, e.g., together formulated as a wet granulated solid preparation); and (ii) the second component (e.g., contained in a vial or bottle) includes one or more liquids and one or more one or more other pharmaceutically acceptable excipients together forming a liquid carrier. In other embodiments, each of component (i) and (ii) is provided in its own separate kit or pack.

In certain of these embodiments, component (i) includes the chemical entity (e.g., a niclosamide compound, or a pharmaceutically acceptable salt and/or hydrate and/or cocrystal thereof) and one or more (e.g., all) of the following excipients:

(a) One or more (e.g., one) binders (e.g., a polyvinyl polymer, such as polyvinylpyrrolidone (povidone);
(b) One or more (e.g., one or two, e.g., two) glidants and/or lubricants, such as magnesium stearate and/or talc;
(c) One or more (e.g., one or two; e.g., one) disintegrants, such as crospovidone; and
(d) One or more (e.g., one or two; e.g., one) diluents, such as lactose (e.g., lactose monohydrate).

In certain embodiments, component (i) includes from about 40 weight percent to about 80 weight percent (e.g., from about 50 weight percent to about 70 weight percent, from about 55 weight percent to about 70 weight percent; from about 60 weight percent to about 65 weight percent; e.g., about 62.1 weight percent) of the chemical entity (e.g., a niclosamide compound, or a pharmaceutically acceptable salt and/or hydrate and/or cocrystal thereof).

In certain embodiments, component (i) includes from about 0.5 weight percent to about 5 weight percent (e.g., from about 1.5 weight percent to about 4.5 weight percent, from about 2 weight percent to about 3.5 weight percent; e.g., about 2.76 weight percent) of the binder (e.g., povidone).

In certain embodiments, component (i) includes from about 0.5 weight percent to about 5 weight percent (e.g., from about 0.5 weight percent to about 3 weight percent, from about 1 weight percent to about 3 weight percent; about 2 weight percent e.g., about 1.9 weight percent) of the disintegrant (e.g., crospovidone).

In certain embodiments, component (i) includes from about 10 weight percent to about 50 weight percent (e.g., from about 20 weight percent to about 40 weight percent, from about 25 weight percent to about 35 weight percent; e.g., about 31.03 weight percent) of the diluent (e.g., lactose, e.g., lactose monohydrate).

In certain embodiments, component (i) includes from about 0.05 weight percent to about 5 weight percent (e.g., from about 0.05 weight percent to about 3 weight percent) of the glidants and/or lubricants.

In certain embodiments (e.g., when component (i) includes one or more lubricants, such as magnesium stearate), component (i) includes from about 0.05 weight percent to about 1 weight percent (e.g., from about 0.05 weight percent to about 1 weight percent; from about 0.1 weight percent to about 1 weight percent; from about 0.1 weight percent to about 0.5 weight percent; e.g., about 0.27 weight percent) of the lubricant (e.g., magnesium stearate).

In certain embodiments (when component (i) includes one or more lubricants, such as talc), component (i) includes from about 0.5 weight percent to about 5 weight percent (e.g., from about 0.5 weight percent to about 3 weight percent, from about 1 weight percent to about 3 weight percent; from about 1.5 weight percent to about 2.5 weight percent; from about 1.8 weight percent to about 2.2 weight percent; about 1.93 weight percent) of the lubricant (e.g., talc).

In certain of these embodiments, each of (a), (b), (c), and (d) above is present.

In certain embodiments, component (i) includes the ingredients and amounts as shown in Table 7.

TABLE 7

| Ingredient | Weight Percent |
|---|---|
| niclosamide compound | 40 weight percent to about 80 weight percent (e.g., from about 50 weight percent to about 70 weight percent, from about 55 weight percent to about 70 weight percent; from about 60 weight percent to about 65 weight percent; e.g., about 62.1 weight percent) |
| Crospovidone (Kollidon CL) | 0.5 weight percent to about 5 weight percent (e.g., from about 0.5 weight percent to about 3 weight percent, from about 1 weight percent to about 3 weight percent; about 1.93 weight percent |
| lactose monohydrate (Pharmatose 200M) | about 10 weight percent to about 50 weight percent (e.g., from about 20 weight percent to about 40 weight percent, from about 25 weight percent to about 35 weight percent; e.g., about 31.03 weight percent |
| Povidone (Kollidon K30) | about 0.5 weight percent to about 5 weight percent (e.g., from about 1.5 weight percent to about 4.5 weight percent, from about 2 weight percent to about 3.5 weight percent; e.g., about 2.76 weight percent |
| talc | 0.5 weight percent to about 5 weight percent (e.g., from about 0.5 weight percent to about 3 weight percent, from about 1 weight percent to about 3 weight percent; from about 1.5 weight percent to about 2.5 weight percent; from about 1.8 weight percent to about 2.2 weight percent; e.g., about 1.93 weight percent |
| Magnesium stearate | about 0.05 weight percent to about 1 weight percent (e.g., from about 0.05 weight percent to about 1 weight percent; from about 0.1 weight percent to about 1 weight percent; from about 0.1 weight percent to about 0.5 weight percent; e.g., about 0.27 weight percent |

In certain embodiments, component (i) includes the ingredients and amounts as shown in Table 8.

TABLE 8

| Ingredient | Weight Percent |
|---|---|
| niclosamide compound | About 62.1 weight percent) |
| Crospovidone (Kollidon CL) | About 1.93 weight percent |
| lactose monohydrate (Pharmatose 200M) | About 31.03 weight percent |

TABLE 8-continued

| Ingredient | Weight Percent |
|---|---|
| Povidone (Kollidon K30) | About 2.76 weight percent |
| talc | About 1.93 weight percent |
| Magnesium stearate | About 0.27 weight percent |

In certain embodiments, component (i) is formulated as a wet granulated solid preparation. In certain of these embodiments an internal phase of ingredients (the chemical entity, disintegrant, and diluent) are combined and mixed in a high-shear granulator. A binder (e.g., povidone) is dissolved in water to form a granulating solution. This solution is added to the Inner Phase mixture resulting in the development of granules. While not wishing to be bound by theory, granule development is believed to be facilitated by the interaction of the polymeric binder with the materials of the internal phase. Once the granulation is formed and dried, an external phase (e.g., one or more lubricants—not an intrinsic component of the dried granulation), is added to the dry granulation. Itis believed that lubrication of the granulation is important to the flowability of the granulation, in particular for packaging. See, e.g., Example 8.

In certain of the foregoing embodiments, component (ii) includes water and one or more (e.g., all) of the following excipients:

(a') One or more (e.g., one, two; e.g., two) thickeners, viscosity enhancing agents, binders, and/or mucoadhesive agents (e.g., cellulose or cellulose esters or ethers or derivatives or salts thereof (e.g., methyl cellulose); and polyvinyl polymers such as polyvinylpyrrolidone (povidone);

(b') One or more (e.g., one or two; e.g., two) preservatives, such as a paraben, e.g., methyl 4-hydroxybenzoate (methylparaben), or a pharmaceutically acceptable salt or ester thereof, propyl 4-hydroxybenzoate (propylparaben), or a pharmaceutically acceptable salt or ester thereof, or a combination thereof; and (c') One or more (e.g., one or two; e.g., two) buffers, such as phosphate buffer system (e.g., sodium dihydrogen phosphate dihydrate, disodium phosphate dodecahydrate);

In certain of the foregoing embodiments, component (ii) includes water and one or more (e.g., all) of the following excipients:

(a") a first thickener, viscosity enhancing agent, binder, and/or mucoadhesive agent (e.g., a cellulose or cellulose ester or ether or derivative or salt thereof (e.g., methyl cellulose));

(a"') a second thickener, viscosity enhancing agent, binder, and/or mucoadhesive agent (e.g., a polyvinyl polymer, such as polyvinylpyrrolidone (povidone));

(b") a first preservative, such as a paraben, e.g., propyl 4-hydroxybenzoate (propylparaben), or a pharmaceutically acceptable salt or ester thereof;

(b") a second preservative, such as a paraben, e.g., methyl 4-hydroxybenzoate (methylparaben), or a pharmaceutically acceptable salt or ester thereof, (c") a first buffer, such as phosphate buffer system (e.g., disodium phosphate dodecahydrate);

(c"') a second buffer, such as phosphate buffer system (e.g., sodium dihydrogen phosphate dehydrate), In certain embodiments, component (ii) includes from about 0.05 weight percent to about 5 weight percent (e.g., from about 0.05 weight percent to about 3 weight percent, from about 0.1 weight percent to about 3 weight percent; e.g., about 1.4 weight percent) of (a").

In certain embodiments, component (ii) includes from about 0.05 weight percent to about 5 weight percent (e.g., from about 0.05 weight percent to about 3 weight percent, from about 0.1 weight percent to about 2 weight percent; e.g., about 1.0 weight percent) of (a"').

In certain embodiments, component (ii) includes from about 0.005 weight percent to about 0.1 weight percent (e.g., from about 0.005 weight percent to about 0.05 weight percent; e.g., about 0.02 weight percent) of (b").

In certain embodiments, component (ii) includes from about 0.05 weight percent to about 1 weight percent (e.g., from about 0.05 weight percent to about 0.5 weight percent; e.g., about 0.20 weight percent) of (b"').

In certain embodiments, component (ii) includes from about 0.05 weight percent to about 1 weight percent (e.g., from about 0.05 weight percent to about 0.5 weight percent; e.g., about 0.15 weight percent) of (c").

In certain embodiments, component (ii) includes from about 0.005 weight percent to about 0.5 weight percent (e.g., from about 0.005 weight percent to about 0.3 weight percent; e.g., about 0.15 weight percent) of (c"').

In certain of these embodiments, each of (a")-(c"') is present.

In certain embodiments, component (ii) includes water (up to 100%) and the ingredients and amounts as shown in Table 9.

TABLE 9

| Ingredient | Weight Percent |
|---|---|
| methyl cellulose (Methocel A15C premium) | 0.05 weight percent to about 5 weight percent (e.g., from about 0.05 weight percent to about 3 weight percent, from about 0.1 weight percent to about 3 weight percent; e.g., about 1.4 weight percent |
| Povidone (Kollidon K30) | 0.05 weight percent to about 5 weight percent (e.g., from about 0.05 weight percent to about 3 weight percent, from about 0.1 weight percent to about 2 weight percent; e.g., about 1.0 weight percent |
| propyl 4-hydroxybenzoate | about 0.005 weight percent to about 0.1 weight percent (e.g., from about 0.005 weight percent to about 0.05 weight percent; e.g., about 0.02 weight percent) |
| methyl 4-hydroxybenzoate | about 0.05 weight percent to about 1 weight percent (e.g., from about 0.05 weight percent to about 0.5 weight percent; e.g., about 0.20 weight percent) |
| disodium phosphate dodecahydrate | about 0.05 weight percent to about 1 weight percent (e.g., from about 0.05 weight percent to about 0.5 weight percent; e.g., about 0.15 weight percent) |
| sodium dihydrogen phospahate dihydrate | about 0.005 weight percent to about 0.5 weight percent (e.g., from about 0.005 weight percent to about 0.3 weight percent; e.g., about 0.15 weight percent) |

In certain embodiments, component (ii) includes water (up to 100%) and the ingredients and amounts as shown in Table 10.

TABLE 10

| Ingredient | Weight Percent |
|---|---|
| methyl cellulose (Methocel A15C premium) | about 1.4 weight percent |
| Povidone (Kollidon K30) | about 1.0 weight percent |
| propyl 4-hydroxybenzoate | about 0.02 weight percent |
| methyl 4-hydroxybenzoate | about 0.20 weight percent |

TABLE 10-continued

| Ingredient | Weight Percent |
|---|---|
| disodium phosphate dodecahydrate | about 0.15 weight percent |
| sodium dihydrogen phospahate dihydrate | about 0.15 weight percent |

Ready-to-use" enemas are generally be provided in a "single-use" sealed disposable container of plastic or glass. Those formed of a polymeric material preferably have sufficient flexibility for ease of use by an unassisted patient. Typical plastic containers can be made of polyethylene. These containers may comprise a tip for direct introduction into the rectum. Such containers may also comprise a tube between the container and the tip. The tip is preferably provided with a protective shield which is removed before use. Optionally the tip has a lubricant to improve patient compliance.

In some embodiments, the enema formulation (e.g., suspension) is poured into a bottle for delivery after it has been prepared in a separate container. In certain embodiments, the bottle is a plastic bottle (e.g., flexible to allow for delivery by squeezing the bottle), which can be a polyethylene bottle (e.g., white in color). In some embodiments, the bottle is a single chamber bottle, which contains the suspension or solution. In other embodiments, the bottle is a multichamber bottle, where each chamber contains a separate mixture or solution. In still other embodiments, the bottle can further include a tip or rectal cannula for direct introduction into the rectum. In some embodiments, the enema formulation can be delivered in the device shown in WO 2017/040864 which is incorporated herein by reference in its entirety. The device includes a plastic bottle, a breakable capsule, and a rectal cannula and single flow pack.

Ocular Delivery

In some embodiments, niclosamide, or a pharmaceutically acceptable salt thereof, or a pharmaceutical composition thereof is suitable for local and topical administration to the eye (e.g., eye drops, ocular ointments, ocular gels, contact lenses, and opthalamic inserts). See, e.g., Dubald et al. Pharmaceutics. 2018; 10(1): 10 and Patel et al. World J Pharmacol. 2013; 2(2): 47-64. In some embodiments, compositions suitable for ocular delivery include in situ gelling systems, liposomes, nanoparticles, niosomes, nanoemulsions, and microemulsions Ocular compositions can include, without limitation, one or more of any of the following: viscogens (e.g., polyvinylalcohol (PVA), hydroxylmethylcellulose, hydroxylethylcellulose carboxymethylcellulose, glycerin, polyvinylpyrrolidone, polyethylene glycol); stabilizers (e.g., pluronic (triblock copolymers), cyclodextrins); preservatives (e.g., benzalkonium chloride, ETDA, SofZia (boric acid, propylene glycol, sorbitol, and zinc chloride; Alcon Laboratories, Inc.), purite (stabilized oxychloro complex; Allergan, Inc.)); permeation enhancers (e.g,. polyoxyethylene glycol ester and ethylenediaminetetra acetic acid sodium salt); and lubricants. In some embodiments, a composition for ocular delivery is isotonic.

In some embodiments, an ocular ointment includes non-aqueous excipients. In some embodiments, an ocular ointment has an oleaginous base, an absorption base, a water-removable base, or a water soluble base. An oleaginous base can be a lipophilic ointment. For example, an oleaginous base can include petrolatum and white ointment. An adsorption base can be used as emollient. For example, an adsorption base can include lanolin, fatty alcohol and petrolatum. A water-soluble base can include only water soluble excipients such as macrogol with high molecular weight. A water removable base includes compositions that are an oil in water emulsion.

In some embodiments, an ocular gel is a hydrogel. For example, a preformed gel or a composition that forms a gel in situ. Hydrogels can include polymers such as methylcellulose, hydroxylethylcellulose, sodium hyaluronate, sodium alginate, povidone, polyvinylalcohol, cellulose acetate and derivatives, carbomer, magrogol, pseudolatex, polymethacrylic acid, alginate sodium, gellan gum (GELRITE®), pluronics, poly(n-isopropyl acrylamide), oly(acrylic acid), polyacrylamide, poloxamer, chitosan, and hydroxyl propyl methyl cellulose.

Other Forms of Delivery

In some embodiments, the chemical entities described herein or a pharmaceutical composition thereof are suitable for local and topical administration to the eye (e.g., eye drops). Ocular compositions can include, without limitation, one or more of any of the following: viscogens (e.g., Carboxymethylcellulose, Glycerin, Polyvinylpyrrolidone, Polyethylene glycol); Stabilizers (e.g., Pluronic (triblock copolymers), Cyclodextrins); Preservatives (e.g., Benzalkonium chloride, ETDA, SofZia (boric acid, propylene glycol, sorbitol, and zinc chloride; Alcon Laboratories, Inc.), Purite (stabilized oxychloro complex; Allergan, Inc.)).

In some embodiments, the chemical entities described herein or a pharmaceutical composition thereof are suitable for local and topical administration to skin (e.g., ointments and creams). Ointments are semisolid preparations that are typically based on petrolatum or other petroleum derivatives. Creams containing the selected active agent are typically viscous liquid or semisolid emulsions, often either oil-in-water or water-in-oil. Cream bases are typically water-washable, and contain an oil phase, an emulsifier and an aqueous phase. The oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation is generally a nonionic, anionic, cationic or amphoteric surfactant. As with other carriers or vehicles, an ointment base should be inert, stable, nonirritating and non-sensitizing.

Dosages

The dosages may be varied depending on the requirement of the patient, the severity of the condition being treating and the particular compound being employed. Determination of the proper dosage for a particular situation can be determined by one skilled in the medical arts. The total daily dosage may be divided and administered in portions throughout the day or by means providing continuous delivery.

In some embodiments, a niclosamide compound is administered is administered at a dosage of from about 0.01 mg/Kg to about 200 mg/Kg (e.g., from about 0.01 mg/Kg to about 150 mg/Kg; from about 0.01 mg/Kg to about 100 mg/Kg; from about 0.01 mg/Kg to about 50 mg/Kg; from about 0.01 mg/Kg to about 10 mg/Kg; from about 0.01 mg/Kg to about 5 mg/Kg; from about 0.1 mg/Kg to about 200 mg/Kg; from about 0.1 mg/Kg to about 150 mg/Kg; from about 0.1 mg/Kg to about 100 mg/Kg; from about 0.1 mg/Kg to about 50 mg/Kg; from about 0.1 mg/Kg to about 10 mg/Kg; from about 0.1 mg/Kg to about 5 mg/Kg).

In certain embodiments, the niclosamide compound is administered at a dosage of from about 15 mg/Kg to about 100 mg/Kg (e.g., from about 15 mg/Kg to about 90 mg/Kg, from about 20 mg/Kg to about 100 mg/Kg; from about 20 mg/Kg to about 90 mg/Kg; from about 20 mg/Kg to about 80 mg/Kg; from about 30 mg/Kg to about 90 mg/Kg; from about 30 mg/Kg to about 80 mg/Kg; from about 35 mg/Kg to about 75 mg/Kg; from about 10 mg/Kg to about 50 mg/Kg; from about 15 mg/Kg to about 45 mg/Kg; e.g., about 35 mg/Kg or about 75 mg/Kg). In other embodiments, the chemical entity is administered at a dosage of from about 0.1 mg/Kg to about 10 mg/Kg (e.g., from about 0.1 mg/Kg to about 5 mg/Kg; from about 1 mg/Kg to about 10 mg/Kg; from about 1 mg/Kg to about 5 mg/Kg).

In some embodiments, formulations include from about 0.5 mg to about 2500 mg (e.g., from about 0.5 mg to about 2000 mg, from about 0.5 mg to about 1000 mg, from about 0.5 mg to about 750 mg, from about 0.5 mg to about 600 mg, from about 0.5 mg to about 500 mg, from about 0.5 mg to about 400 mg, from about 0.5 mg to about 300 mg, from about 0.5 mg to about 200 mg; e.g., from about 5 mg to about 2500 mg, from about 5 mg to about 2000 mg, from about 5 mg to about 1000 mg; from about 5 mg to about 750 mg; from about 5 mg to about 600 mg; from about 5 mg to about 500 mg; from about 5 mg to about 400 mg; from about 5 mg to about 300 mg; from about 5 mg to about 200 mg; e.g., from about 50 mg to about 2000 mg, from about 50 mg to about 1000 mg, from about 50 mg to about 750 mg, from about 50 mg to about 600 mg, from about 50 mg to about 500 mg, from about 50 mg to about 400 mg, from about 50 mg to about 300 mg, from about 50 mg to about 200 mg; e.g., from about 100 mg to about 2500 mg, from about 100 mg to about 2000 mg, from about 100 mg to about 1000 mg, from about 100 mg to about 750 mg, from about 100 mg to about 700 mg, from about 100 mg to about 600 mg, from about 100 mg to about 500 mg, from about 100 mg to about 400 mg, from about 100 mg to about 300 mg, from about 100 mg to about 200 mg; e.g., from about 150 mg to about 2500 mg, from about 150 mg to about 2000 mg, from about 150 mg to about 1000 mg, from about 150 mg to about 750 mg, from about 150 mg to about 700 mg, from about 150 mg to about 600 mg, from about 150 mg to about 500 mg, from about 150 mg to about 400 mg, from about 150 mg to about 300 mg, from about 150 mg to about 200 mg; e.g., from about 150 mg to about 500 mg; e.g., from about 300 mg to about 2500 mg, from about 300 mg to about 2000 mg, from about 300 mg to about 1000 mg, from about 300 mg to about 750 mg, from about 300 mg to about 700 mg, from about 300 mg to about 600 mg; e.g., from about 400 mg to about 2500 mg, from about 400 mg to about 2000 mg, from about 400 mg to about 1000 mg, from about 400 mg to about 750 mg, from about 400 mg to about 700 mg, from about 400 mg to about 600 from about 400 mg to about 500 mg; e.g., 150 mg or 450 mg) of the niclosamide compound.

In certain embodiments, formulations include from about 50 mg to about 250 mg (e.g., from about 100 mg to about 200; e.g., about 150 mg) of the niclosamide compound.

The foregoing dosages can be administered on a daily basis (e.g., as a single dose per day; or as two or more divided doses per day; or a two or more doses; e.g., two doses per day) or non-daily basis (e.g., every other day, every two days, every three days, once weekly, twice weeks, once every two weeks, once a month). In certain embodiments, dosages can be administered for about 1 week, about 2 weeks, about 3 weeks, about 4 weeks, about 5 weeks, about 6 weeks, about 7 weeks, about 8 weeks, about 3 months, about 6 months, about 1 year, or beyond. For example, dosages (e.g., about 2.5 mg/mL or about 7.5 mg/mL) of the chemical entity in liquid carrier can be administered twice a day on a daily basis for about 6 weeks. In certain of these embodiments, the chemical entity is niclosamide, or a pharmaceutically acceptable salt and/or hydrate and/or cocrystal thereof. For example, about 2.5 mg/mL or about 7.5 mg/mL of niclosamide in liquid carrier can be administered twice a day on a daily basis for about 6 weeks. Representative liquid carriers include, e.g., those previously described in conjunction with component (ii).

A number of embodiments of the invention have been described. Nevertheless, it will be understood that various modifications may be made without departing from the spirit and scope of the invention. Accordingly, other embodiments are within the scope of the following claims.

What is claimed is:

1. A method for treating a digestive symptom in a subject diagnosed as having a COVID-19 viral infection and in need of such treatment, the method comprising orally administering an effective amount of niclosamide:

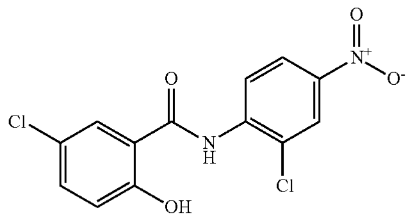 [SMILES: O=C(Nc1ccc([N+](=O)[O-])cc1Cl)c1cc(Cl)ccc1O]

or a pharmaceutically acceptable salt thereof, to the subject;

wherein the effective amount of niclosamide, or a pharmaceutically acceptable salt thereof, decreases an amount of COVID-19-viral RNA load in a fecal sample, an anal swab sample, or a rectal swab sample obtained from the subject by about 45% to about 99% relative to a baseline amount of COVID-19-viral RNA load, wherein the baseline amount of COVID-19 viral RNA load is an amount of COVID-19-related viral RNA that is present in a fecal sample, an anal swab sample, or a rectal swab sample obtained from the subject prior to administration of the niclosamide, or a pharmaceutically acceptable salt thereof.

2. The method of claim 1, wherein the method comprises administering niclosamide.

3. The method of claim 1, wherein at least some of the COVID-19 viral infection is present in the gastrointestinal tract of the subject.

4. The method of claim 3, wherein the effective amount of niclosamide, or a pharmaceutically acceptable salt thereof, decreases a COVID-19 viral load in the gastrointestinal tract of the subject relative to a baseline COVID-19 viral load, wherein the baseline COVID-19 viral load is the COVID-19 viral load in the gastrointestinal tract of the subject prior to administration of the niclosamide, or a pharmaceutically acceptable salt thereof.

5. The method of claim 1, wherein the digestive symptom is selected from the group consisting of lack or loss of appetite, diarrhea, vomiting, abdominal pain, and combinations thereof.

6. The method of claim 1, wherein the digestive symptom is diarrhea.

7. The method of claim 1, wherein the subject does not exhibit an accompanying respiratory symptom.

8. The method of claim 1, wherein the subject exhibits an accompanying respiratory symptom.

9. The method of claim 4, wherein the method comprises measuring viral load with rRT-PCR.

10. The method of claim 1, wherein the subject suffers from, or is predisposed to suffer from colitis.

11. The method of claim 10, wherein the colitis is an autoimmune colitis.

12. The method of claim 10, wherein the colitis is an inflammatory bowel disease.

13. The method of claim 10, wherein the colitis is ulcerative colitis, Crohn's disease, or iatrogenic autoimmune colitis.

14. The method of claim 3, wherein the digestive symptom appears from 2-14 days after the subject's exposure to coronavirus.

15. The method of claim 1, wherein the method further comprises administering a second therapeutic agent.

16. The method of claim 15, wherein the second therapeutic agent is selected from the group consisting of azithromycin, remdesivir, hydroxychloroquine, colchicine, and chloroquine.

17. The method of claim 1, wherein the niclosamide, or a pharmaceutically acceptable salt thereof, is administered by tablet or pill.

18. The method of claim 1, wherein the method comprises orally administering the niclosamide, or a pharmaceutically acceptable salt thereof, as a pharmaceutical composition, wherein the pharmaceutical composition is capable of local delivery to the GI tract.

19. The method of claim 1, wherein the method comprises orally administering the niclosamide, or a pharmaceutically acceptable salt thereof, as a pharmaceutical composition, wherein the pharmaceutical composition is capable of local delivery to the colon or small intestine.

20. The method of claim 1, wherein the subject is a human.

21. The method of claim 1, wherein the decrease occurs within about one week, or about two weeks, or about three weeks, or about four weeks from the start of administration of the niclosamide, or a pharmaceutically acceptable salt thereof.

22. A method for treating a subject having a COVID-19 viral infection and is in need of such treatment, the method comprising orally administering an effective amount of niclosamide:

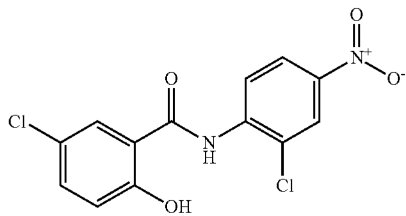 [SMILES: O=C(Nc1ccc([N+](=O)[O-])cc1Cl)c1cc(Cl)ccc1O]

or a pharmaceutically acceptable salt thereof, to the subject so as to treat the COVID-19 viral infection;

wherein the effective amount of niclosamide, or a pharmaceutically acceptable salt thereof, decreases an amount of COVID-19 viral RNA load in a fecal sample, an anal swab sample, or a rectal swab sample obtained from the subject by about 45% to about 99% relative to a baseline amount of COVID-19 viral RNA load, wherein the baseline amount of COVID-19 viral RNA load is an amount of COVID-19 viral RNA that is present in a fecal sample, an anal swab sample, or a rectal swab sample obtained from the subject prior to administration of the niclosamide, or a pharmaceutically acceptable salt thereof.

23. The method of claim 22, wherein the decrease occurs within about one week from the start of administration of the niclosamide, or a pharmaceutically acceptable salt thereof.

24. The method of claim 22, wherein the decrease occurs within about two weeks from the start of administration of the niclosamide, or a pharmaceutically acceptable salt thereof.

25. The method of claim 22, wherein the decrease occurs within about three weeks from the start of administration of the niclosamide, or a pharmaceutically acceptable salt thereof.

26. The method of claim 22, wherein the decrease occurs within about four weeks from the start of administration of the niclosamide, or a pharmaceutically acceptable salt thereof.

* * * * *